(12) United States Patent
Howbert et al.

(10) Patent No.: US 9,718,796 B2
(45) Date of Patent: *Aug. 1, 2017

(54) SUBSTITUTED BENZOAZEPINES AS TOLL-LIKE RECEPTOR MODULATORS

(75) Inventors: James Jeffry Howbert, Redmond, WA (US); Robert Hershberg, Seattle, WA (US); Laurence E. Burgess, Boulder, CO (US); Hong Woon Yang, Boulder, CO (US)

(73) Assignees: VENTIRX PHARMACEUTICALS, INC., Seattle, WA (US); ARRAY BIOPHARMA, INC., Boulder, CO (US)

( * ) Notice: Subject to any disclaimer, the term of this patent is extended or adjusted under 35 U.S.C. 154(b) by 113 days.

This patent is subject to a terminal disclaimer.

(21) Appl. No.: 13/979,632

(22) PCT Filed: Jan. 12, 2012

(86) PCT No.: PCT/US2012/021110
§ 371 (c)(1),
(2), (4) Date: Nov. 18, 2013

(87) PCT Pub. No.: WO2012/097173
PCT Pub. Date: Jul. 19, 2012

(65) Prior Publication Data
US 2014/0066432 A1    Mar. 6, 2014

Related U.S. Application Data

(60) Provisional application No. 61/432,068, filed on Jan. 12, 2011.

(51) Int. Cl.
| | | |
|---|---|---|
| *A61K 31/55* | (2006.01) |
| *C07D 223/16* | (2006.01) |
| *C07D 401/04* | (2006.01) |
| *C07D 401/14* | (2006.01) |
| *C07D 403/06* | (2006.01) |
| *C07D 403/10* | (2006.01) |
| *C07D 413/10* | (2006.01) |
| *C07D 295/192* | (2006.01) |
| *C07D 487/04* | (2006.01) |

(52) U.S. Cl.
CPC .......... *C07D 295/192* (2013.01); *A61K 31/55* (2013.01); *C07D 223/16* (2013.01); *C07D 401/04* (2013.01); *C07D 403/10* (2013.01); *C07D 413/10* (2013.01); *C07D 487/04* (2013.01)

(58) Field of Classification Search
CPC .... A61K 31/55; C07D 223/16; C07D 401/04; C07D 401/14; C07D 403/06; C07D 403/10; C07D 413/10
USPC ................ 514/212.02, 213.01; 540/543, 593
See application file for complete search history.

(56) References Cited

U.S. PATENT DOCUMENTS

| 8,242,106 | B2 | 8/2012 | Howbert et al. |
| 8,314,090 | B2 | 11/2012 | Howbert et al. |
| 8,524,702 | B2 | 9/2013 | Howbert et al. |
| 8,691,809 | B2 | 4/2014 | Howbert et al. |
| 2008/0234251 | A1 | 9/2008 | Doherty et al. |
| 2008/0306050 | A1 | 12/2008 | Doherty et al. |
| 2010/0029585 | A1 | 2/2010 | Howbert et al. |
| 2010/0216989 | A1 | 8/2010 | Howbert et al. |
| 2014/0088085 | A1 | 3/2014 | Burgess et al. |

FOREIGN PATENT DOCUMENTS

| EP | 0825186 A1 | 2/1998 |
| WO | WO 2007/024612 A2 | 3/2007 |
| WO | WO 2007/040840 A2 | 4/2007 |
| WO | WO 2010/054215 A1 | 5/2010 |
| WO | WO 2010/077613 A1 | 7/2010 |
| WO | WO 2010/093436 A2 | 8/2010 |
| WO | WO 2012/097177 A2 | 7/2012 |

*Primary Examiner* — Brenda Coleman
(74) *Attorney, Agent, or Firm* — Marshall, Gerstein & Borun LLP

(57) ABSTRACT

Provided are compositions and methods useful for modulation of signaling through the Toll-like receptors TLR7 and/or TLR8. The compositions and methods have use in treating or preventing disease, including cancer, autoimmune disease, fibrotic disease, cardiovascular disease, infectious disease, inflammatory disorder, graft rejection, or graft-versus-host disease.

19 Claims, 2 Drawing Sheets

SUBSTITUTED BENZOAZEPINES AS TOLL-LIKE RECEPTOR MODULATORS

RELATED APPLICATIONS

This application is a national stage application, filed under 35 U.S.C. §371, of International Application No. PCT/US2012/021110, filed Jan. 12, 2012, which claims priority to, and the benefit of, U.S. provisional application No. 61/432,068, filed Jan. 12, 2011, the contents of each of which are incorporated herein by reference in their entireties.

FIELD OF THE INVENTION

This invention relates to methods and compositions for modulating immune function. More specifically, this invention relates to compositions and methods for modulating TLR7- and/or TLR8-mediated signaling.

BACKGROUND OF THE INVENTION

Stimulation of the immune system, which includes stimulation of either or both innate immunity and adaptive immunity, is a complex phenomenon that can result in either protective or adverse physiologic outcomes for the host. In recent years there has been increased interest in the mechanisms underlying innate immunity, which is believed to initiate and support adaptive immunity. This interest has been fueled in part by the recent discovery of a family of highly conserved pattern recognition receptor proteins known as Toll-like receptors (TLRs) believed to be involved in innate immunity as receptors for pathogen associated molecular patterns (PAMPs). Compositions and methods useful for modulating innate immunity are therefore of great interest, as they may affect therapeutic approaches to conditions involving autoimmunity, inflammation, allergy, asthma, graft rejection, graft versus host disease (GvHD), infection, cancer, and immunodeficiency.

Toll-like receptors (TLRs) are type I transmembrane proteins that allow organisms (including mammals) to detect microbes and initiate an innate immune response (Beutler, B., *Nature* 2004, 430:257-263). They contain homologous cytoplasmic domains and leucine-rich extracellular domains and typically form homodimers that sense extracellular (or internalized) signals and subsequently initiate a signal transduction cascade via adaptor molecules such as MyD88 (myeloid differentiation factor 88). There is such high homology in the cytoplasmic domains of the TLRs that, initially, it was suggested that similar signaling pathways exist for all TLRs (Re, F., Strominger, J. L., *Immunobiology* 2004, 209:191-198). Indeed, all TLRs can activate NF-kB and MAP kinases; however, the cytokine/chemokine release profiles derived from TLR activation appears unique to each TLR. Additionally, the signaling pathway that TLRs stimulate is very similar to the pathway that the cytokine receptor IL-1R induces. This may be due to the homology that these receptors share, i.e., TIR (Toll/IL-1R homology) domains. Once the TIR domain is activated in TLRs and MyD88 is recruited, activation of the IRAK family of serine/threonine kinases results which eventually promotes the degradation of Ik-B and activation of NF-kB (Means T. K., et al. *Life Sci.* 2000, 68:241-258). While it appears that this cascade is designed to allow extracellular stimuli to promote intracellular events, there is evidence that some TLRs migrate to endosomes where signaling can also be initiated. This process may allow for intimate contact with engulfed microbes and fits with the role that these receptors play in the innate immune response (Underhill, D. M., et al., *Nature* 1999, 401:811-815). This process might also allow host nucleic acids, released by damaged tissues (for example, in inflammatory disease) or apoptosis to trigger a response via endosomal presentation. Among mammals, there are 11 TLRs that coordinate this rapid response. A hypothesis put forward years ago (Janeway, C. A., Jr., *Cold Spring Harb. Symp. Quant. Biol.* 1989, 54:1-13) that the innate immune response initiates the adaptive immune response through the pattern of TLR activation caused by microbes has now been substantiated. Thus, the pathogen-associated molecular patterns (PAMPs) presented by a diverse group of infectious organisms results in a innate immune response involving certain cytokines, chemokines and growth factors followed by a precise adaptive immune response tailored to the infectious pathogen via antigen presentation resulting in antibody production and cytotoxic T cell generation.

Gram-negative bacterial lipopolysaccharide (LPS) has long been appreciated as an adjuvant and immune-stimulant and as a pharmacological tool for inducing an inflammatory reaction in mammals similar to septic shock. Using a genetic approach, TLR4 was identified as the receptor for LPS. The discovery that LPS is an agonist of TLR4 illustrates the usefulness of TLR modulation for vaccine and human disease therapy (Aderem, A.; Ulevitch, R. J., *Nature* 2000, 406:782-787). It is now appreciated that various TLR agonists can activate B cells, neutrophils, mast cells, eosinophils, endothelial cells and several types of epithelia in addition to regulating proliferation and apoptosis of certain cell types.

To date, TLR7 and TLR8, which are somewhat similar, have been characterized as receptors for single-stranded RNA found in endosomal compartments and thus thought to be important for the immune response to viral challenge. Imiquimod, an approved topical antiviral/anti-cancer drug, has recently been described as a TLR7 agonist that has demonstrated clinical efficacy in certain skin disorders (Miller R. L., et al., *Int. J. Immunopharm.* 1999, 21:1-14). This small molecule drug has been described as a structural mimetic of ssRNA. TLR8 was first described in 2000 (Du, X., et al., *European Cytokine Network* 2000 (September), 11(3):362-371) and was rapidly ascribed to being involved with the innate immune response to viral infection (Miettinen, M., et al., *Genes and Immunity* 2001 (October), 2(6):349-355).

Recently it was reported that certain imidazoquinoline compounds having antiviral activity are ligands of TLR7 and TLR8 (Hemmi H., et al. (2002) *Nat. Immunol.* 3:196-200; Jurk M., et al. (2002) *Nat. Immunol.* 3:499). Imidazoquinolines are potent synthetic activators of immune cells with antiviral and antitumor properties. Using macrophages from wildtype and MyD88-deficient mice, Hemmi et al. recently reported that two imidazoquinolines, imiquimod and resiquimod (R848), induce tumor necrosis factor (TNF) and interleukin-12 (IL-12) and activate NF-icB only in wildtype cells, consistent with activation through a TLR (Hemmi H., et al. (2002) *Nat. Immunol.* 3:196-200). Macrophages from mice deficient in TLR7 but not other TLRs produced no detectable cytokines in response to these imidazoquinolines. In addition, the imidazoquinolines induced dose-dependent proliferation of splenic B cells and the activation of intracellular signaling cascades in cells from wildtype but not TLR7−/− mice. Luciferase analysis established that expression of human TLR7, but not TLR2 or TLR4, in human embryonic kidney cells results in NF-KB activation in response to resiquimod. The findings of Hemmi et al. thus suggest that these imidazoquinoline compounds are non-natural ligands of TLR7 that can induce signaling through TLR7. Recently it was reported that R848 is also a ligand for human TLR8 (Jurk M., et al. (2002) Nat. Immunol. 3:499).

In view of the great therapeutic potential for compounds that modulate toll-like receptors, and despite the work that has already been done, there is a substantial ongoing need to expand their use and therapeutic benefits.

SUMMARY OF THE INVENTION

The compositions described herein are useful for modulating immune responses in vitro and in vivo. Such compositions will find use in a number of clinical applications, such as in methods for treating or preventing conditions involving unwanted immune activity, including inflammatory and autoimmune disorders.

Specifically, the invention relates to a compound having the formula I:

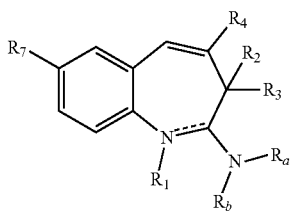

or a salt thereof,
wherein ===== is a double bond or a single bond;
$R_2$ and $R_3$ are independently selected from H and unsubstituted or substituted $C_1$-$C_6$ alkyl, or $R_2$ and $R_3$, together with the carbon atom to which they are attached, form a saturated carbocycle having from 3 to 7 members, or $R_3$ and one of $R_a$ or $R_b$, together with the atoms to which they are attached, form a 5-7 member heterocyclic ring;
$R_7$ is selected from the group consisting of:

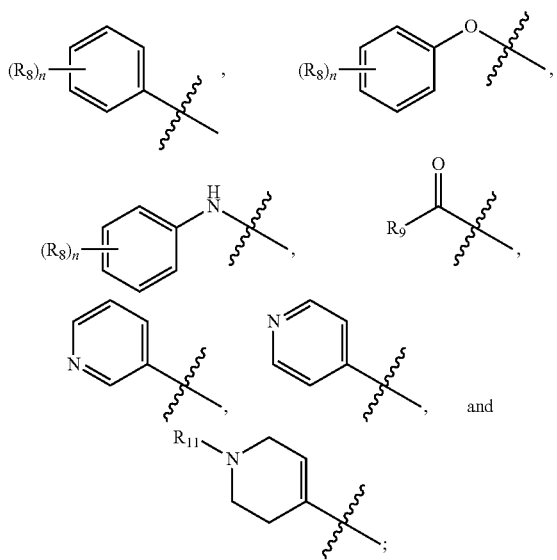

n is 0, 1, 2 or 3;
each $R_8$ is, independently, selected from unsubstituted or substituted $C_1$-$C_6$ alkyl, unsubstituted or substituted $C_1$-$C_6$ alkoxy, halogen, trihalomethyl, unsubstituted or substituted $C_1$-$C_6$ alkoxycarbonyl, nitro, unsubstituted or substituted carbonylamino, unsubstituted or substituted sulfonamide, unsubstituted or substituted heterocycle comprising 1 or 2, 5- or 6-member rings and 1-4 heteroatoms selected from N, O and S, and

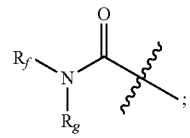

$R_9$ is unsubstituted or substituted $C_1$-$C_6$ alkyl, unsubstituted or substituted $C_1$-$C_6$ alkoxy, or
—$NR_hR_j$;

$R_f$ and $R_g$ are each, independently, H, unsubstituted or substituted $C_1$-$C_6$ alkyl or $R_f$ and $R_g$, together with the nitrogen atom to which they are attached, form a heterocycle comprising 1 or 2, 5- or 6-member rings and optionally 1-3 additional heteroatoms selected from N, O and S;

$R_h$ and $R_j$ are each, independently, H, unsubstituted or substituted $C_1$-$C_6$ alkyl, unsubstituted or substituted $C_6$-$C_{10}$ aryl or $R_h$ and $R_j$, together with the nitrogen atom to which they are attached, form a heterocycle comprising 1 or 2, 5- or 6-member rings and optionally 1-3 additional heteroatoms selected from N, O and S;

$R_{11}$ is H, unsubstituted or substituted $C_1$-$C_6$ alkylcarbonyl, unsubstituted or substituted $C_1$-$C_6$ alkoxycarbonyl, 3-7 member carbocycle substituted carbonyl, or 5-7 member heterocyclyl substituted carbonyl;

$R_4$ is H, halogen, unsubstituted or substituted $C_1$-$C_6$ alkyl, or —C(O)NR$_c$R$_d$, or —C(O)OR$_{10}$;

$R_c$ and $R_d$ are independently selected from H and unsubstituted or substituted $C_1$-$C_6$ alkyl, where the $C_1$-$C_6$ alkyl is optionally substituted with aminocarbonyl or hydroxyl;

$R_{10}$ is selected from H and $C_1$-$C_6$ alkyl, where the alkyl is optionally substituted with one or more —OH;

$R_a$ and $R_b$ are independently selected from H, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ alkoxy, $C_1$-$C_6$ alkoxycarbonyl substituted amino, and $R_e$, wherein the $C_1$-$C_6$ alkyl is optionally substituted with one or more —OR$_{10}$ or $R_e$, or $R_e$ and one of $R_a$ and $R_b$ together with the atoms to which they are attached, form a 5-7 member heterocyclic ring;

$R_e$ is selected from —$NH_2$, —$NH(C_1$-$C_6$ alkyl), and —$N(C_1$-$C_6$ alkyl)$_2$; and $R_1$ is absent when ===== is a double bond, or when ===== is a single bond, $R_1$ is H, or $R_1$ and one of $R_a$ or $R_b$ are connected to form a saturated, partially unsaturated, or unsaturated heterocycle having 5-7 ring members and the other of $R_a$ or $R_b$ may be hydrogen or absent as necessary to accommodate ring unsaturation;

with the proviso that:
when $R_7$ is

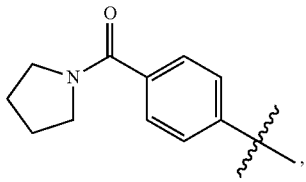

then $R_4$ is not —$COOR_{10}$ where $R_{10}$ is $C_1$-$C_6$ alkyl, or —$CONR_cR_d$ where both $R_c$ and $R_d$ are unsubstituted $C_1$-$C_6$ (lower) alkyl, and $R_a$ and $R_b$ are not both selected from H, unsubstituted $C_1$-$C_6$ alkyl and $R_e$.

In embodiments, the compound having the formula I is a compound of formula (II)

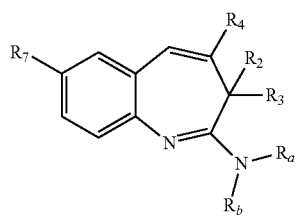

(II)

or a salt thereof, wherein $R_2$ and $R_3$ are independently selected from H and unsubstituted or substituted $C_1$-$C_6$ alkyl, or $R_2$ and $R_3$, together with the carbon atom to which they are attached, form a saturated carbocycle having from 3 to 7 members, or $R_3$ and one of $R_a$ or $R_b$, together with the atoms to which they are attached, form a 5-7 member heterocyclic ring;

$R_7$ is selected from the group consisting of:

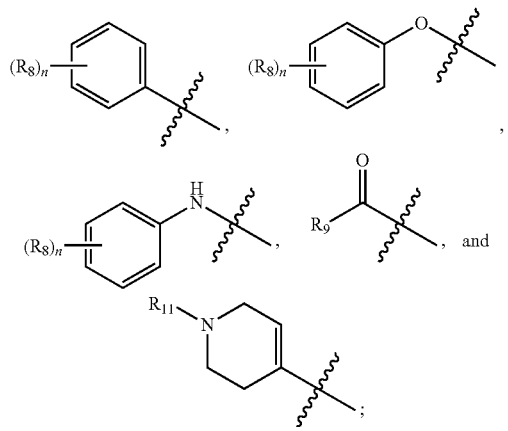

n is 0, 1, 2 or 3;

each $R_8$ is, independently, selected from unsubstituted or substituted $C_1$-$C_6$ alkyl, unsubstituted or substituted $C_1$-$C_6$ alkoxy, halogen, trihalomethyl, unsubstituted or substituted $C_1$-$C_6$ alkoxycarbonyl, unsubstituted or substituted carbonylamino, unsubstituted or substituted sulfonamide, unsubstituted or substituted heterocycle comprising 1 or 2, 5- or 6-member rings and 1-4 heteroatoms selected from N, O and S, and

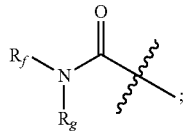

$R_9$ is unsubstituted or substituted $C_1$-$C_6$ alkyl, unsubstituted or substituted $C_1$-$C_6$ alkoxy or —$NR_hR_i$;

$R_f$ and $R_g$ are each, independently, H, unsubstituted or substituted $C_1$-$C_6$ alkyl or $R_f$ and $R_g$, together with the nitrogen atom to which they are attached, form a heterocycle comprising 1 or 2, 5- or 6-member rings and optionally 1-3 additional heteroatoms selected from N, O and S;

$R_h$ and $R_i$ are each, independently, H, unsubstituted or substituted $C_1$-$C_6$ alkyl or $R_h$ and $R_i$, together with the nitrogen atom to which they are attached, form a heterocycle comprising 1 or 2, 5- or 6-member rings and optionally 1-3 additional heteroatoms selected from N, O and S;

$R_{11}$ is H, unsubstituted or substituted $C_1$-$C_6$ alkylcarbonyl, unsubstituted or substituted $C_1$-$C_6$ alkoxycarbonyl, 3-7 member carbocycle substituted carbonyl, or 5-7 member heterocyclyl substituted carbonyl;

$R_4$ is selected from H, —$C(O)NR_cR_d$, —$C(O)OR_{10}$, halogen, and unsubstituted $C_1$-$C_6$ alkyl;

$R_c$ and $R_d$ are independently selected from H and unsubstituted or substituted $C_1$-$C_6$ alkyl, where the $C_1$-$C_6$ alkyl is optionally substituted with aminocarbonyl or hydroxyl;

$R_{10}$ is $C_1$-$C_6$ alkyl optionally substituted with one or more —OH;

$R_a$ and $R_b$ are independently selected from H, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ alkoxy, $C_1$-$C_6$ alkoxycarbonyl substituted amino, and $R_e$, wherein the $C_1$-$C_6$ alkyl is optionally substituted with one or more —OH, —$OR_{10}$ or $R_e$, or $R_3$ and one of $R_a$ or $R_b$ together with the atoms to which they are attached, form a 5-7 member heterocyclic ring;

$R_e$ is selected from —$NH_2$, —$NH(C_1$-$C_6$ alkyl), and —$N(C_1$-$C_6$ alkyl)$_2$;

with the proviso that:
when $R_4$ is —$C(O)OR_{10}$ and $R_7$ is

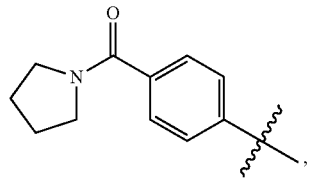

then neither $R_a$ nor $R_b$ is H or unsubstituted or substituted $C_1$-$C_6$ alkyl.

In one embodiment, $R_4$ is not —$C(O)NR_cR_d$.
In one embodiment, $R_4$ is not —$C(O)NR_cR_d$ where $R_c$ and $R_d$ are both unsubstituted or substituted $C_1$-$C_6$ alkyl.
In one embodiment, $R_7$ is

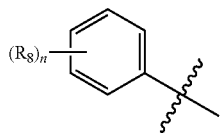

and n is 1, 2 or 3.

In one embodiment, R$_7$ is not 3-methylphenyl.

In one embodiment, R$_7$ is not 3,4-dichlorophenyl.

In one embodiment, R$_7$ is not

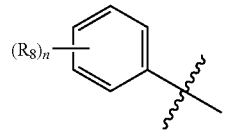

where n is 1 and R$_8$ is cyclopropyl substituted carbonylamino.

In one embodiment, R$_7$ is

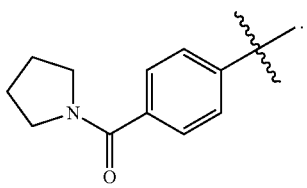 [SMILES: "." ; *c1ccc(C(=O)N2CCCC2)cc1]

In another embodiment, at least one of R$_a$ and R$_b$ is not hydrogen in the compound of formula I or II, or, for example, one of R$_a$ and R$_b$ is alkyl and the other of R$_a$ and R$_b$ is hydrogen. Further, in another embodiment, one or more of R$_a$ and R$_b$ is alkyl substituted with R$_e$. In a different embodiment, both R$_a$ and R$_b$ are alkyl or, one of R$_a$ and R$_b$ is R$_e$ and the other of R$_a$ and R$_b$ is hydrogen.

In a certain embodiment, at least one of R$_2$ and R$_3$ in the compound of formula I or II is not hydrogen, or, for example, R$_2$ and R$_3$ are connected to form a saturated carbocycle, where the saturated carbocycle is cyclopropyl.

In an alternative embodiment, R$_4$ of formula I or II is —C(O)OR$_{10}$, where R$_{10}$ is alkyl or is ethyl. In another embodiment, R$_4$ is —C(O)NR$_c$R$_d$, where both R$_c$ and R$_d$ are alkyl or both are propyl. Moreover, in certain embodiments, at least one of R$_c$ or R$_d$ is alkyl substituted with one —OH. For example, one of R$_c$ and R$_d$ is

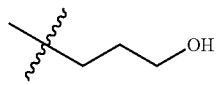 [SMILES: *CCCO]

and the remaining R$_c$ or R$_d$ is propyl.

In one embodiment, R$_4$ is halogen. For example, R$_4$ is Br.

In one embodiment, R$_4$ is unsubstituted C$_1$-C$_6$ alkyl. For example, R$_4$ is methyl. For example, R$_4$ is ethyl.

In embodiments, the compound of formula I is a compound having the formula III:

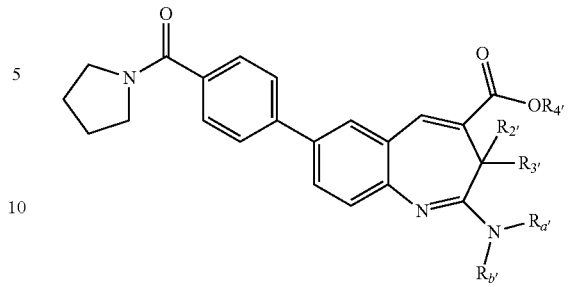

or a salt thereof, wherein R$_{2'}$ and R$_{3'}$ are independently selected from H and unsubstituted or substituted C$_1$-C$_6$ alkyl, or R$_{2'}$ and R$_{3'}$, together with the carbon atom to which they are attached, form a saturated carbocycle having from 3 to 7 members, or R$_{3'}$ and one of R$_{a'}$ or R$_{b'}$, together with the atoms to which they are attached, form a 5-7 member heterocyclic ring;

R$_{4'}$ is C$_1$-C$_6$ alkyl optionally substituted with one or more —OH; and

R$_{a'}$ and R$_{b'}$ are independently selected from H and unsubstituted or substituted C$_1$-C$_6$ alkyl, wherein the alkyl is optionally substituted with one or more —OH, or R$_{3'}$ and one of R$_{a'}$ or R$_{b'}$, together with the atoms to which they are attached, form a 5-7 member heterocyclic ring;

with the proviso that the compound is not

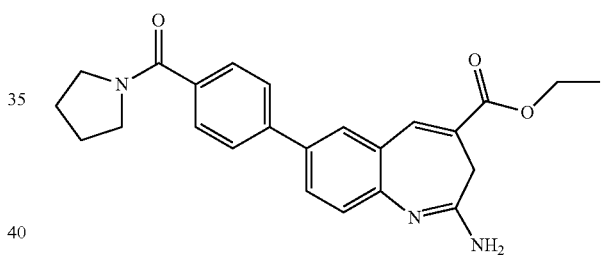

or a salt thereof.

In one embodiment, R$_{2'}$ and R$_{3'}$ are each H.

In one embodiment, R$_{2'}$ or R$_{3'}$ is unsubstituted or substituted C$_1$-C$_6$ alkyl. For example, R$_{2'}$ or R$_{3'}$ is methyl. For example, both R$_{2'}$ and R$_{3'}$ are each methyl.

In one embodiment, R$_{2'}$ and R$_{3'}$, together with the carbon atom to which they are attached, form a saturated carbocycle having from 3 to 7 members. For example, R$_{2'}$ and R$_{3'}$, together with the carbon atom to which they are attached, form a cyclopropyl ring.

In certain embodiments, the salt of the compounds of the invention is a pharmaceutically acceptable salt. For example, the salt of a compound of formula I is a pharmaceutically acceptable salt. For example, the salt of a compound of formula II is a pharmaceutically acceptable salt. For example, the salt of a compound of formula III is a pharmaceutically acceptable salt. Further, the compound is a TLR8 antagonist.

Another aspect of the invention includes a kit for treating a TLR7- and/or TLR8-mediated condition that comprises a first pharmaceutical composition comprising the compounds of the invention describes supra and infra; and optionally instructions for use. Additionally, the kit includes a second pharmaceutical composition, where the second pharmaceutical composition comprises a second compound for treating a TLR7- and/or TLR8-mediated condition. The kit also comprises instructions for the simultaneous, sequential or separate administration of said first and second pharmaceutical compositions to a patient in need thereof.

The invention described herein also relates to a pharmaceutical composition, which comprises a compound or salt thereof as described supra and infra together with a pharmaceutically acceptable diluent or carrier. Additionally, the compound of the invention is used as a medicament for treating a TLR7 and/or TLR8-mediated condition in a human or animal, where the method of treating a TLR7- and/or TLR8-mediated condition includes administering to a patient, in need thereof, an effective amount of a compound described herein. Moreover, in certain embodiments, the compound is used in the manufacture of a medicament for the treatment of an autoimmune condition in a human or animal. In an alternative embodiment, the invention relates to a method of modulating a patient's immune system that includes administering to a patient in need thereof an effective amount of a compound supra and infra.

For example, a compound of the invention is a TLR8 antagonist. A TLR8 antagonist is characterized by the ability to inhibit the activation of a TLR8 receptor with an $IC_{50}$ of 25 µM or less. For example, a TLR8 antagonist inhibits the activation of a TLR8 receptor with an $IC_{50}$ of about 25 µM, 15 µM, 10 µM, 7.5 µM, 5 µM, 2.5 µM, 1.5 µM, 1 µM, 0.5 µM, 0.25 µM, 0.1 µM, 0.05 µM, 0.01 µM, 0.005 µM, 0.001 µM, 0.0005 µM or about 0.0002 µM.

For example, a compound of the invention is a TLR7 antagonist. A TLR7 antagonist is characterized by the ability to inhibit the activation of a TLR7 receptor with an $IC_{50}$ of 25 µM or less. For example, a TLR7 antagonist inhibits the activation of a TLR7 receptor with an $IC_{50}$ of about 25 µM, 15 µM, 10 µM, 7.5 µM, 5 µM, 2.5 µM, 1.5 µM, 1 µM, 0.5 µM, 0.25 µM, 0.1 µM, 0.01 or about 0.001 µM.

For example, a compound of the invention is a TLR7/8 antagonist. A TLR7/8 antagonist is characterized by the ability to inhibit, independently, the activation of both TLR7 and TLR8 receptors with an $IC_{50}$ of 25 µM or less. For example, a TLR7/8 antagonist inhibits the activation of both TLR7 and TLR8 receptors, independently, with an $IC_{50}$ of about 25 µM, 15 µM, 10 µM, 7.5 µM, 5 µM, 2.5 µM, 1.5 µM, 1 µM, 0.5 µM, 0.25 µM, 0.1 µM, 0.01 µM, or about 0.001 µM.

The compounds of the invention may be used in combination with other known therapeutic agents. Accordingly, this invention also relates to pharmaceutical compositions comprising a therapeutically effective amount of a compound of the invention or a salt thereof, in combination with a second therapeutic agent.

This invention further provides methods of modulating TLR7- and/or TLR8-mediated signaling, comprising contacting a cell expressing TLR7 and/or TLR8 with an effective amount of a compound of the invention, or a salt thereof. In one aspect, the method inhibits TLR7- and/or TLR8-mediated immunostimulatory signaling.

This invention further provides methods of modulating TLR7- and/or TLR8-mediated immunostimulation in a subject, comprising administering to a patient having or at risk of developing TLR7- and/or TLR8-mediated immunostimulation a compound of the invention, or a salt thereof, in an amount effective to inhibit TLR7- and/or TLR8-mediated immunostimulation in the subject.

This invention further provides methods of treating or preventing a disease or condition by modulation of TLR7- and/or TLR8-mediated cellular activities, comprising administering to a warm-blooded animal, such as a mammal, for example a human, having or at risk of developing said disease or condition, a compound of the invention, or a salt thereof.

This invention further provides methods of modulating the immune system of a mammal, comprising administering to a mammal a compound of the invention, or a salt thereof, in an amount effective to modulate said immune system.

Further provided is a compound of the invention, or a salt thereof for use as a medicament in the treatment of the diseases or conditions described herein in a mammal, for example, a human, suffering from such disease or condition. Also provided is the use of a compound of the invention, a salt thereof, in the preparation of a medicament for the treatment of the diseases and conditions described herein in a mammal, for example a human, suffering from such disease or condition.

Further provided is a compound of the invention, or a salt thereof for use as a medicament in the prevention of the diseases or conditions described herein in a mammal, for example, a human, exposed to or predisposed to the disease or condition, but the mammal does not yet experience or display symptoms of such disease or condition. Also provided is the use of a compound of the invention, a salt thereof, in the preparation of a medicament for the treatment of the diseases and conditions described herein in a mammal, for example a human, suffering from such disease or condition.

The disease or condition is selected from cancer, autoimmune disease, infectious disease, inflammatory disorder, graft rejection, and graft-verses-host disease.

This invention further provides kits comprising one or more compounds of the invention, or a salt thereof. The kit may further comprise a second compound or formulation comprising a second pharmaceutical agent.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF THE INVENTION

Figure 1:
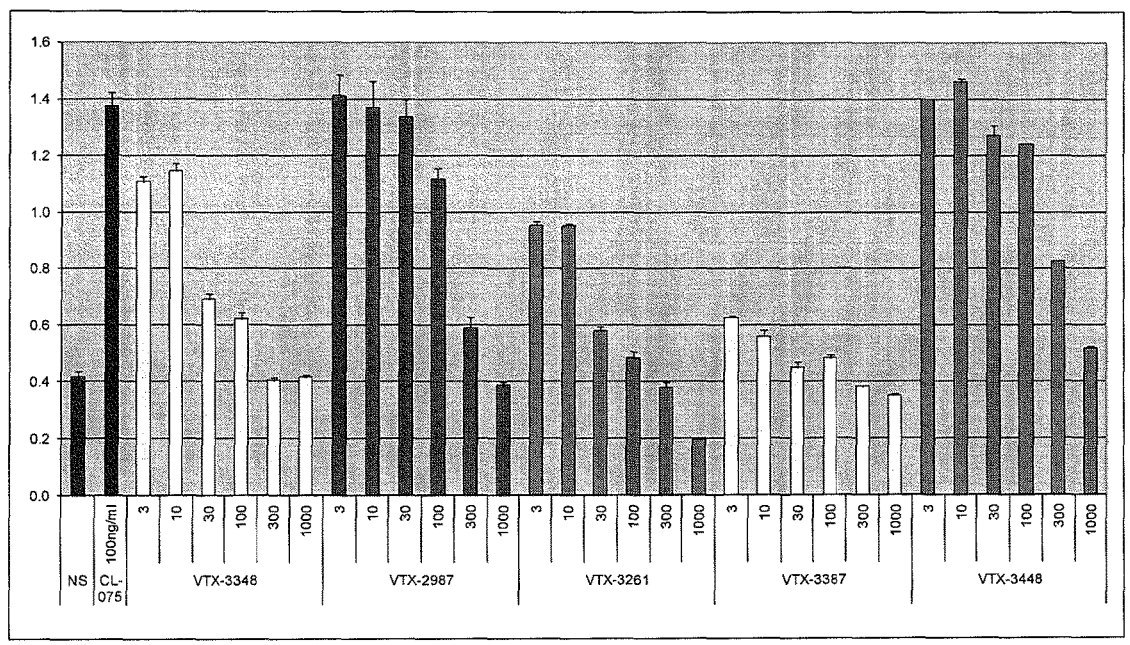
FIG. 1 is a graph depicting the dose-dependent inhibition of IL-8 production in human PBMC stimulated with CL075 following administration of certain compounds described herein.

In certain aspects, the invention provides compositions and methods useful for modulating TLR7- and/or TLR8-mediated signaling. More specifically, one aspect of this invention provides a compound having the formula I:

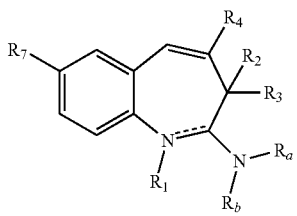

(I)

or a salt thereof, wherein ----- is a double bond or a single bond;

$R_2$ and $R_3$ are independently selected from H and unsubstituted or substituted $C_1$-$C_6$ alkyl, or $R_2$ and $R_3$, together with the carbon atom to which they are attached, form a saturated carbocycle having from 3 to 7 members, or $R_3$ and one of $R_a$ or $R_b$, together with the atoms to which they are attached, form a 5-7 member heterocyclic ring;

$R_7$ is selected from the group consisting of:

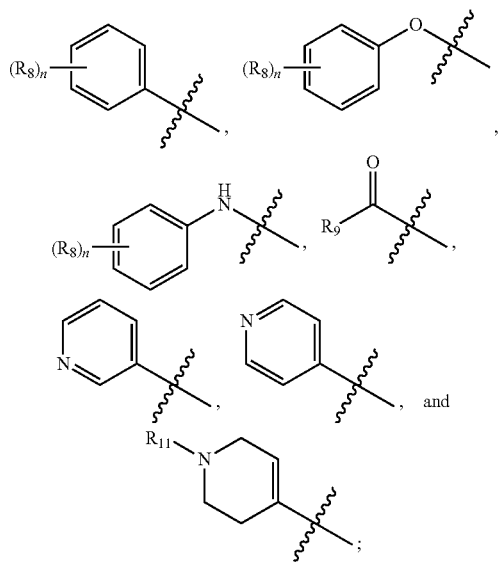

n is 0, 1, 2 or 3;

each $R_8$ is, independently, selected from unsubstituted or substituted $C_1$-$C_6$ alkyl, unsubstituted or substituted $C_1$-$C_6$ alkoxy, halogen, trihalomethyl, unsubstituted or substituted $C_1$-$C_6$ alkoxycarbonyl, nitro, unsubstituted or substituted carbonylamino, unsubstituted or substituted sulfonamide, unsubstituted or substituted heterocycle comprising 1 or 2, 5- or 6-member rings and 1-4 heteroatoms selected from N, O and S, and

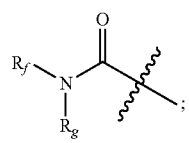

$R_9$ is unsubstituted or substituted $C_1$-$C_6$ alkyl, unsubstituted or substituted $C_1$-$C_6$ alkoxy, or —$NR_hR_j$;

$R_f$ and $R_g$ are each, independently, H, unsubstituted or substituted $C_1$-$C_6$ alkyl or $R_f$ and $R_g$, together with the nitrogen atom to which they are attached, form a heterocycle comprising 1 or 2, 5- or 6-member rings and optionally 1-3 additional heteroatoms selected from N, O and S;

$R_h$ and $R_j$ are each, independently, H, unsubstituted or substituted $C_1$-$C_6$ alkyl, unsubstituted or substituted $C_6$-$C_{10}$ aryl or $R_h$ and $R_j$, together with the nitrogen atom to which they are attached, form a heterocycle comprising 1 or 2, 5- or 6-member rings and optionally 1-3 additional heteroatoms selected from N, O and S;

$R_{11}$ is H, unsubstituted or substituted $C_1$-$C_6$ alkylcarbonyl, unsubstituted or substituted $C_1$-$C_6$ alkoxycarbonyl, 3-7 member carbocycle substituted carbonyl, or 5-7 member heterocyclyl substituted carbonyl;

$R_4$ is H, halogen, unsubstituted $C_1$-$C_6$ alkyl, or —C(O)$NR_cR_d$, or —C(O)$OR_{10}$;

$R_c$ and $R_d$ are independently selected from H and unsubstituted or substituted $C_1$-$C_6$ alkyl, where the $C_1$-$C_6$ alkyl is optionally substituted with aminocarbonyl or hydroxyl;

$R_{10}$ is selected from H and $C_1$-$C_6$ alkyl, where the alkyl is optionally substituted with one or more —OH;

$R_a$ and $R_b$ are independently selected from H, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ alkoxy, $C_1$-$C_6$ alkoxycarbonyl substituted amino, and $R_e$, wherein the $C_1$-$C_6$ alkyl is optionally substituted with one or more —$OR_{10}$ or $R_e$, or $R_e$ and one of $R_a$ and $R_b$ together with the atoms to which they are attached, form a 5-7 member heterocyclic ring;

$R_e$ is selected from —$NH_2$, —$NH(C_1$-$C_6$ alkyl), and —$N(C_1$-$C_6$ alkyl)$_2$; and $R_1$ is absent when ----- is a double bond, or when ----- is a single bond, $R_1$ is H, or $R_1$ and one of $R_a$ or $R_b$ are connected to form a saturated, partially unsaturated, or unsaturated heterocycle having 5-7 ring members and the other of $R_a$ or $R_b$ may be hydrogen or absent as necessary to accommodate ring unsaturation;

with the proviso that:
when $R_7$ is

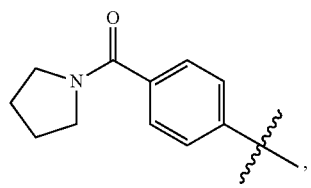 [SMILES: *c1ccc(C(=O)N2CCCC2)cc1 ; ","]

then $R_4$ is not —$COOR_{10}$ where $R_{10}$ is $C_1$-$C_6$ alkyl, or —$CONR_cR_d$ where both $R_c$ and $R_d$ are unsubstituted $C_1$-$C_6$ (lower) alkyl, and $R_a$ and $R_b$ are not both selected from H, unsubstituted $C_1$-$C_6$ alkyl and $R_e$.

In embodiments, the compound of the invention has the formula II:

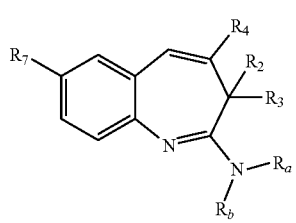

(II)

or a salt thereof, wherein $R_2$ and $R_3$ are independently selected from H and unsubstituted or substituted $C_1$-$C_6$ alkyl, or $R_2$ and $R_3$, together with the carbon atom to which they are attached, form a saturated carbocycle having from 3 to 7 members, or $R_3$ and one of $R_a$ or $R_b$, together with the atoms to which they are attached, form a 5-7 member heterocyclic ring;

$R_7$ is selected from the group consisting of:

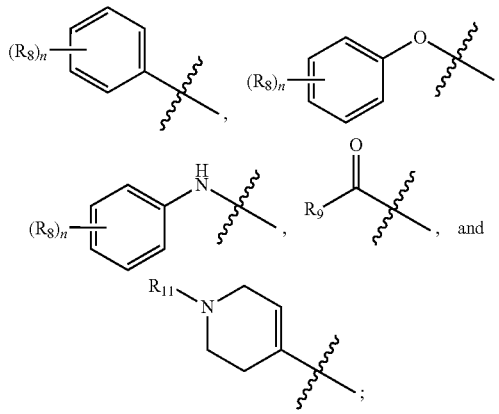

n is 0, 1, 2 or 3;

each $R_8$ is, independently, selected from unsubstituted or substituted $C_1$-$C_6$ alkyl, unsubstituted or substituted $C_1$-$C_6$ alkoxy, halogen, trihalomethyl, unsubstituted or substituted $C_1$-$C_6$ alkoxycarbonyl, unsubstituted or substituted carbonylamino, unsubstituted or substituted sulfonamide, unsubstituted or substituted heterocycle comprising 1 or 2, 5- or 6-member rings and 1-4 heteroatoms selected from N, O and S, and

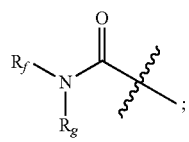

$R_9$ is unsubstituted or substituted $C_1$-$C_6$ alkyl, unsubstituted or substituted $C_1$-$C_6$ alkoxy or —$NR_fR_g$;

$R_f$ and $R_g$ are each, independently, H, unsubstituted or substituted $C_1$-$C_6$ alkyl or $R_f$ and $R_g$, together with the nitrogen atom to which they are attached, form a heterocycle comprising 1 or 2, 5- or 6-member rings and optionally 1-3 additional heteroatoms selected from N, O and S;

$R_{11}$ is H, unsubstituted or substituted $C_1$-$C_6$ alkylcarbonyl, unsubstituted or substituted $C_1$-$C_6$ alkoxycarbonyl, 3-7 member carbocycle substituted carbonyl, or 5-7 member heterocyclyl substituted carbonyl;

$R_4$ is selected from H, —$C(O)NR_cR_d$, —$C(O)OR_{10}$, halogen, and unsubstituted $C_1$-$C_6$ alkyl;

$R_c$ and $R_d$ are independently selected from H and unsubstituted or substituted $C_1$-$C_6$ alkyl, where the $C_1$-$C_6$ alkyl is optionally substituted with aminocarbonyl or hydroxyl;

$R_{10}$ is $C_1$-$C_6$ alkyl optionally substituted with one or more —OH;

$R_a$ and $R_b$ are independently selected from H, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ alkoxy, $C_1$-$C_6$ alkoxycarbonyl substituted amino, and $R_e$, wherein the $C_1$-$C_6$ alkyl is optionally substituted with one or more —OH, —$OR_{10}$ or $R_e$, or $R_3$ and one of $R_a$ or $R_b$ together with the atoms to which they are attached, form a 5-7 member heterocyclic ring;

$R_e$ is selected from —$NH_2$, —$NH(C_1$-$C_6$ alkyl), and —$N(C_1$-$C_6$ alkyl)$_2$;

with the proviso that:

when $R_4$ is —$C(O)OR_{10}$ and $R_7$ is

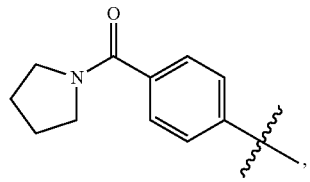

then neither $R_a$ nor $R_b$ is H or unsubstituted or substituted $C_1$-$C_6$ alkyl.

In one embodiment, $R_4$ is not —$C(O)NR_cR_d$.

In one embodiment, $R_4$ is not —$C(O)NR_cR_d$ where $R_c$ and $R_d$ are both unsubstituted or substituted $C_1$-$C_6$ alkyl.

In one embodiment, $R_7$ is

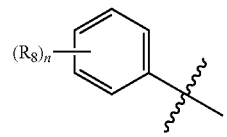

and n is 1, 2 or 3.

In one embodiment, $R_7$ is not 3-methylphenyl.
In one embodiment, $R_7$ is not 3,4-dichlorophenyl.
In one embodiment, $R_7$ is not

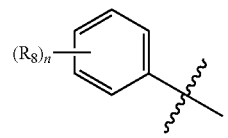

where n is 1 and $R_8$ is cyclopropyl substituted carbonylamino.

In one embodiment, $R_7$ is

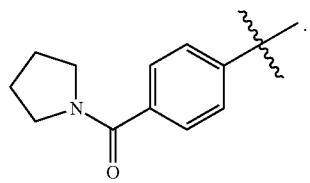 [SMILES: *c1ccc(C(=O)N2CCCC2)cc1]

In another embodiment, at least one of $R_a$ and $R_b$ is not hydrogen in the compound of formula I or II, or, for example, one of $R_a$ and $R_b$ is alkyl and the other of $R_a$ and $R_b$ is hydrogen. Further, in another embodiment, one or more of $R_a$ and $R_b$ is alkyl substituted with $R_e$. In a different embodiment, both $R_a$ and $R_b$ are alkyl or, one of $R_a$ and $R_b$ is $R_e$ and the other of $R_a$ and $R_b$ is hydrogen.

In a certain embodiment, at least one of $R_2$ and $R_3$ in the compound of formula I or II is not hydrogen, or, for example, $R_2$ and $R_3$ are connected to form a saturated carbocycle, where the saturated carbocycle is cyclopropyl.

In an alternative embodiment, $R_4$ of formula I or II is —C(O)O$R_{10}$, where $R_{10}$ is alkyl or is ethyl. In another embodiment, $R_4$ is —C(O)N$R_c R_d$, where both are alkyl or both are propyl. Moreover, in certain embodiments, at least one of $R_c$ or $R_d$ is alkyl substituted with one —OH and at least one of $R_c$ and $R_d$ is

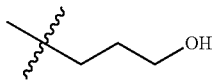 [SMILES: *CCCO]

and the remaining $R_c$ or $R_d$ is propyl.

In one embodiment, $R_4$ is halogen. For example, $R_4$ is Br.

In one embodiment, $R_4$ is unsubstituted $C_1$-$C_6$ alkyl. For example, $R_4$ is methyl. For example, $R_4$ is ethyl.

In embodiments, the compound of the invention has the formula III:

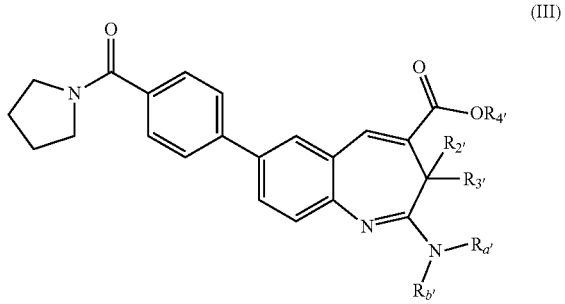

(III)

or a salt thereof, wherein $R_{2'}$ and $R_{3'}$ are independently selected from H and unsubstituted or substituted $C_1$-$C_6$ alkyl, or $R_{2'}$ and $R_{3'}$, together with the carbon atom to which they are attached, form a saturated carbocycle having from 3 to 7 members, or $R_{3'}$ and one of $R_{a'}$ or $R_{b'}$, together with the atoms to which they are attached, form a 5-7 member heterocyclic ring;

$R_{4'}$ is $C_1$-$C_6$ alkyl optionally substituted with one or more —OH; and $R_{a'}$ and $R_{b'}$ are independently selected from H and unsubstituted or substituted $C_1$-$C_6$ alkyl, wherein the alkyl is optionally substituted with one or more —OH, or $R_{3'}$ and one of $R_{a'}$ or $R_{b'}$ together with the atoms to which they are attached, form a 5-7 member heterocyclic ring;

with the proviso that the compound is not

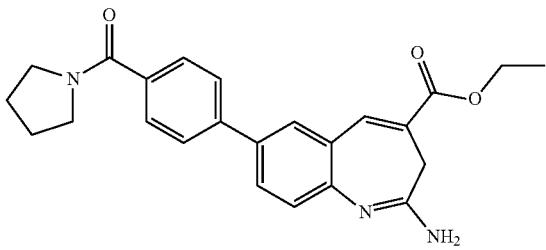 [SMILES: CCOC(=O)C1=Cc2cc(-c3ccc(C(=O)N4CCCC4)cc3)ccc2N=C(N)C1]

or a salt thereof.

In one embodiment, $R_{2'}$ and $R_{3'}$ are each H.

In one embodiment, $R_{2'}$ or $R_{3'}$ is unsubstituted or substituted $C_1$-$C_6$ alkyl. For example, $R_{2'}$ or $R_{3'}$ is methyl. For example, both $R_{2'}$ and $R_{3'}$ are each methyl.

In one embodiment, $R_{2'}$ and $R_{3'}$, together with the carbon atom to which they are attached, form a saturated carbocycle having from 3 to 7 members. For example, $R_{2'}$ and $R_{3'}$, together with the carbon atom to which they are attached, form a cyclopropyl ring.

In certain embodiments, the salt of the compounds of the invention is a pharmaceutically acceptable salt. For example, the salt of a compound of formula I is a pharmaceutically acceptable salt. For example, the salt of a compound of formula II is a pharmaceutically acceptable salt. For example, the salt of a compound of formula III is a pharmaceutically acceptable salt. Further, the compound is a TLR8 antagonist.

Another aspect of the invention includes a kit for treating a TLR7- and/or TLR8-mediated condition that comprises a first pharmaceutical composition comprising the compounds of the invention describes supra and infra; and optionally instructions for use. Additionally, the kit includes a second pharmaceutical composition, where the second pharmaceutical composition comprises a second compound for treating a TLR7- and/or TLR8-mediated condition. The kit also comprises instructions for the simultaneous, sequential or separate administration of said first and second pharmaceutical compositions to a patient in need thereof.

The invention described herein also relates to a pharmaceutical composition, which comprises a compound or salt thereof as described supra and infra together with a pharmaceutically acceptable diluent or carrier. Additionally, the compound of the invention is used as a medicament for treating a TLR7 and/or TLR8-mediated condition in a human or animal, where the method of treating a TLR7- and/or TLR8-mediated condition includes administering to a patient, in need thereof, an effective amount of a compound described herein. Moreover, in certain embodiments, the compound is used in the manufacture of a medicament for the treatment of an autoimmune condition in a human or animal. In an alternative embodiment, the invention relates to a method of modulating a patient's immune system that includes administering to a patient in need thereof an effective amount of a compound supra and infra.

One aspect of the invention relates to a salt of a compound of the invention, wherein the salt is a pharmaceutically acceptable salt.

For example, a compound of the invention is a TLR8 antagonist. A TLR8 antagonist is characterized by the ability to inhibit the activation of a TLR8 receptor with an $IC_{50}$ of 25 µM or less. For example, a TLR8 antagonist inhibits the activation of a TLR8 receptor with an $IC_{50}$ of about 25 µM, 15 µM, 10 µM, 7.5 µM, 5 µM, 2.5 µM, 1.5 µM, 1 µM, 0.5 µM, 0.25 µM, 0.1 µM, 0.05 µM, 0.01 µM, 0.005 µM, 0.001 µM, 0.0005 µM or about 0.0002 µM.

For example, a compound of the invention is a TLR7 antagonist. A TLR7 antagonist is characterized by the ability to inhibit the activation of a TLR7 receptor with an $IC_{50}$ of 25 µM or less. For example, a TLR7 antagonist inhibits the activation of a TLR7 receptor with an $IC_{50}$ of about 25 µM, 15 µM, 10 µM, 7.5 µM, 5 µM, 2.5 µM, 1.5 µM, 1 µM, 0.5 µM, 0.25 µM, 0.1 µM, 0.01 µM, or about 0.001 µM.

For example, a compound of the invention is a TLR7/8 antagonist. A TLR7/8 antagonist is characterized by the ability to inhibit, independently, the activation of both TLR7 and TLR8 receptors with an $IC_{50}$ of 25 µM or less. For example, a TLR7/8 antagonist inhibits the activation of both TLR7 and TLR8 receptors, independently, with an IC$_{50}$ of about 25 μM, 15 μM, 10 μM, 7.5 μM, 5 μM, 2.5 μM, 1.5 μM, 1 μM, 0.5 μM, 0.25 μM, 0.1 μM, 0.01 μM, or about 0.001 μM.

One aspect of the invention relates to a kit for treating a TLR7- and/or TLR8-mediated condition, comprising:
 a) a first pharmaceutical composition comprising a compound of the invention or salt thereof; and
 b) optionally instructions for use.

In one embodiment, the invention relates to the kit further comprising (c) a second pharmaceutical composition, wherein the second pharmaceutical composition comprises a second compound for treating a TLR7- and/or TLR8-mediated condition. In one embodiment, the invention relates to the kit, further comprising instructions for the simultaneous, sequential or separate administration of said first and second pharmaceutical compositions to a patient in need thereof.

One aspect of the invention relates to a pharmaceutical composition, which comprises a compound of the invention or salt thereof, together with a pharmaceutically acceptable diluent or carrier.

One aspect of the invention relates to a compound of the invention for use as a medicament for treating a TLR7- and/or TLR8-mediated condition in a human or animal. In one embodiment, the invention relates to a compound of the invention or salt thereof, in the manufacture of a medicament for the treatment of an abnormal cell growth condition in a human or animal.

One aspect of the invention relates to a method of treating a TLR7- and/or TLR8-mediated condition, comprising administering to a patient in need thereof an effective amount of a compound of the invention or salt thereof.

One aspect of the invention relates to a method of modulating a patient's immune system, comprising administering to a patient in need thereof an effective amount of a compound of the invention or salt thereof.

The invention includes one or more compounds of formula II selected from the compounds listed in Table 1 and salts thereof.

TABLE 1

| Compound No. | R$_7$ | R$_4$ | R$_2$, R$_3$ | R$_a$ | R$_b$ |
|---|---|---|---|---|---|
| 3010 | 4-(pyrrolidin-1-ylcarbonyl)phenyl | COOH | H, H | H | H |
| 3009 | 4-(pyrrolidin-1-ylcarbonyl)phenyl | CONH—i-Pr | H, H | H | H |
| 3058 | 3-(N,N-dimethylcarbamoyl)phenyl | COOEt | H, H | H | H |
| 2937 | 4-(N,N-dimethylcarbamoyl)phenyl | COOEt | H, H | H | H |
| 2882 | phenyl | COOEt | H, H | H | H |
| 3096 | 2-methylphenyl | COOEt | H, H | H | H |
| 3141 | 2-i-Pr-phenyl | COOEt | H, H | H | H |
| 3287 | 3-methylphenyl | COOEt | H, H | H | H |
| 3272 | 4-methylphenyl | COOEt | H, H | H | H |

TABLE 1-continued

| Compound No. | R₇ | R₄ | R₂, R₃ | Rₐ | R_b |
|---|---|---|---|---|---|
| 3162 | 2,6-dimethylphenyl | COOEt | H, H | H | H |
| 3264 | 2-methoxyphenyl | COOEt | H, H | H | H |
| 3267 | 3-methoxyphenyl | COOEt | H, H | H | H |
| 3098 | 4-methoxyphenyl | COOEt | H, H | H | H |
| 3127 | 2-chlorophenyl | COOEt | H, H | H | H |
| 3155 | 2,3-dichlorophenyl | COOEt | H, H | H | H |
| 3102 | 3,4-dichlorophenyl | COOEt | H, H | H | H |
| 3294 | 2-chloro-3-methylphenyl | COOEt | H, H | H | H |
| 3386 | 2-chloro-3-methoxyphenyl | COOEt | H, H | H | H |
| 3126 | 2-trifluoromethylphenyl | COOEt | H, H | H | H |
| 3059 | 3-trifluoromethylphenyl | COOEt | H, H | H | H |
| 3101 | 4-ethoxycarbonylphenyl | COOEt | H, H | H | H |
| 3156 | 4-nitro | COOEt | H, H | H | H |
| 3055 | 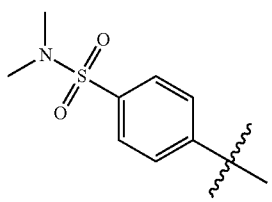 [SMILES: *c1ccc(S(=O)(=O)N(C)C)cc1] | COOEt | H, H | H | H |
| 3119 | 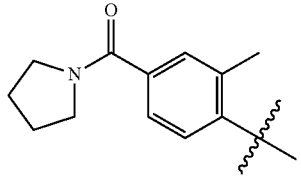 [SMILES: *c1ccc(C(=O)N2CCCC2)cc1C] | COOEt | H, H | H | H |
| 3322 | 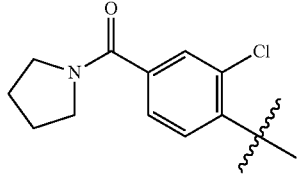 [SMILES: *c1ccc(C(=O)N2CCCC2)cc1Cl] | COOEt | H, H | H | H |
| 3190 | 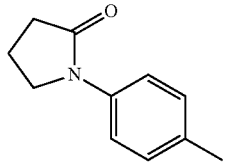 | COOEt | H, H | H | H |
| 3198 | 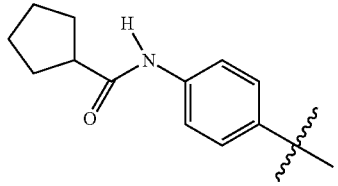 [SMILES: *c1ccc(NC(=O)C2CCCC2)cc1] | COOEt | H, H | H | H |
| 3199 | 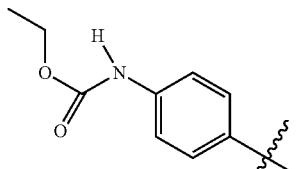 | COOEt | H, H | H | H |

TABLE 1-continued

| Compound No. | R₇ | R₄ | R₂, R₃ | Rₐ | R_b |
|---|---|---|---|---|---|
| 3261 | ethyl (3-chloro-4-yl)carbamate | COOEt | H, H | H | H |
| 3300 | 3-(4-yl)oxazolidin-2-one | COOEt | H, H | H | H |
| 3387 | 3-(3-chloro-4-yl)oxazolidin-2-one | COOEt | H, H | H | H |
| 3290 | 1,1-dimethyl-3-(4-yl)urea | COOEt | H, H | H | H |
| 3343 | (3-methyl-4-yl)(pyrrolidin-1-yl)methanone | 2-(N-propyl-carbamoylmethyl-amido) | H, H | H | H |
| 3342 | (3-chloro-4-yl)(pyrrolidin-1-yl)methanone | 2-(N-propyl-carbamoylmethyl-amido) | H, H | H | H |
| 3336 | ethyl (3-chloro-4-yl)carbamate | 2-(N-propyl-carbamoylmethyl-amido) | H, H | H | H |
| 2946 | phenoxy | COOEt | H, H | H | H |

TABLE 1-continued

| Compound No. | R₇ | R₄ | R₂, R₃ | Rₐ | R_b |
|---|---|---|---|---|---|
| 3128 | 2-methylphenoxy-C(CH₃)- | COOEt | H, H | H | H |
| 3125 | 4-methoxyphenoxy-C(CH₃)- | COOEt | H, H | H | H |
| 3046 | 3-(trifluoromethyl)phenoxy-C(CH₃)- | COOEt | H, H | H | H |
| 3093 | 4-(N,N-dimethylcarbamoyl)phenoxy-C(CH₃)- | COOEt | H, H | H | H |
| 3057 | MeOC(O)-C(CH₃)- | COOEt | H, H | H | H |
| 3197 | i-PrOC(O)-C(CH₃)- | COOEt | H, H | H | H |
| 3094 | pyrrolidin-1-yl-C(O)-C(CH₃)- | COOEt | H, H | H | H |
| 3095 | PhNHC(O)-C(CH₃)- | COOEt | H, H | H | H |

The invention also includes one or more compounds selected from the compounds listed in Table 1A and salts thereof.
TABLE 1A
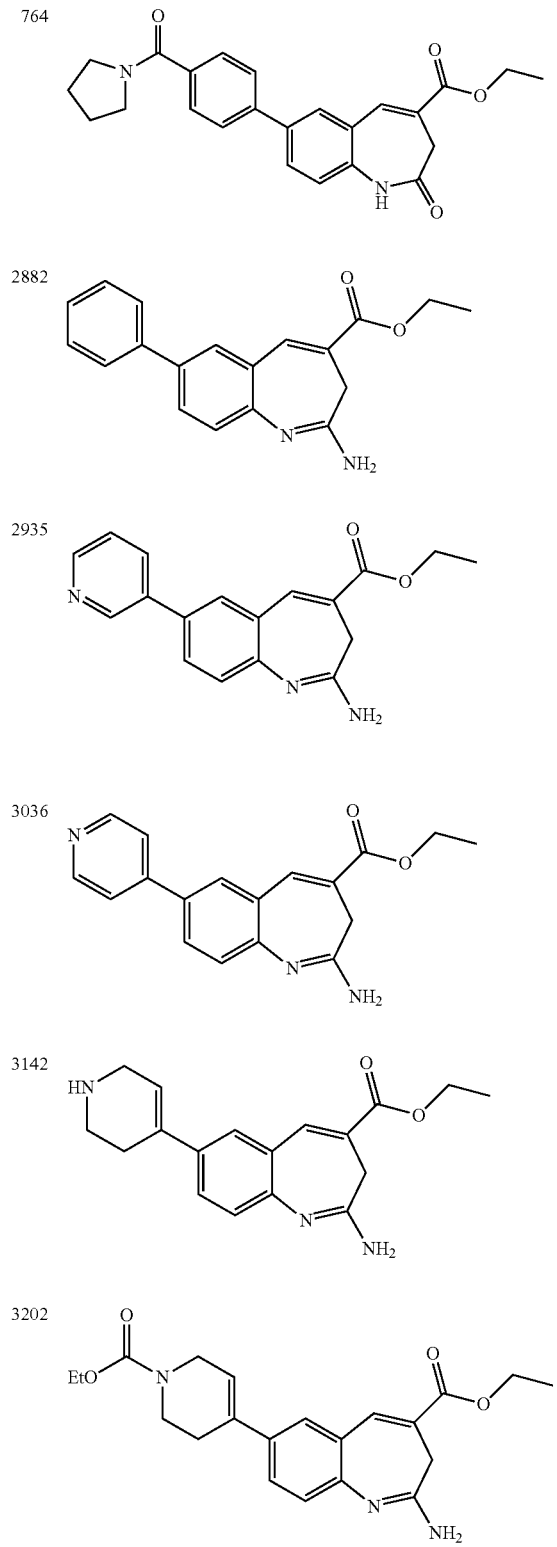
TABLE 1A-continued

TABLE 1A-continued
3062 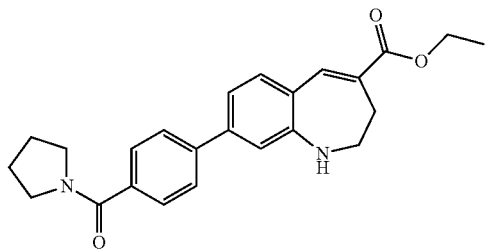 [SMILES: CCOC(=O)C1=Cc2ccc(-c3ccc(C(=O)N4CCCC4)cc3)cc2NCC1]
3228 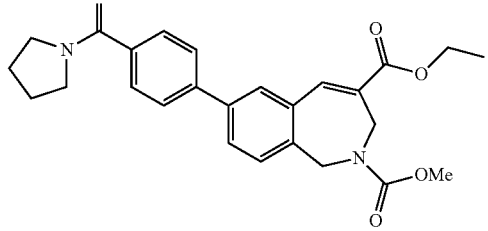
2881 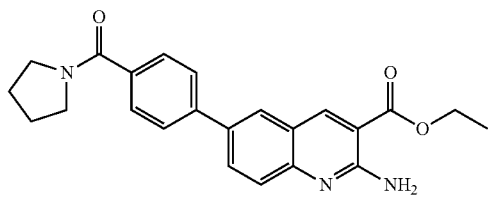 [SMILES: CCOC(=O)c1cc2cc(-c3ccc(C(=O)N4CCCC4)cc3)ccc2nc1N]
2988 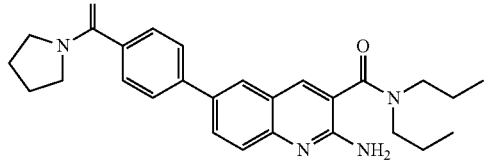
3097 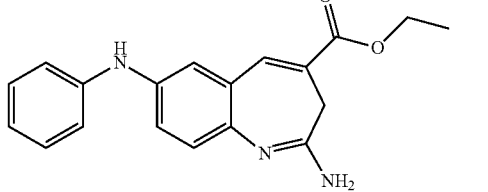
3448 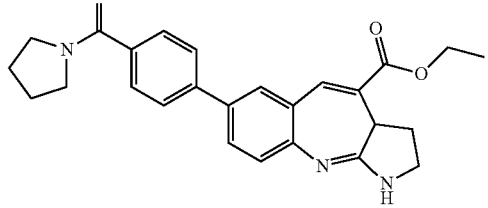
3444 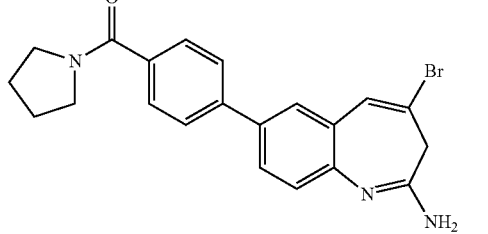
The invention also includes one or more compounds selected from the compounds listed in Table 1B and salts thereof.
TABLE 1B
3173 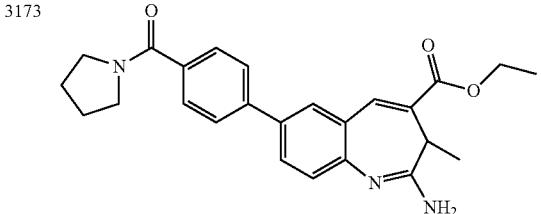
3348 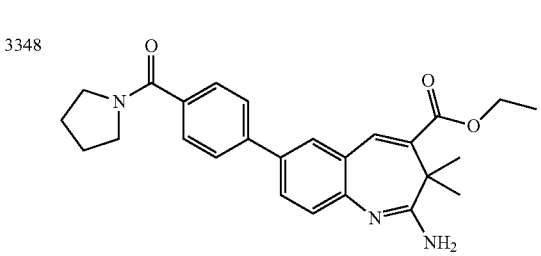
3260 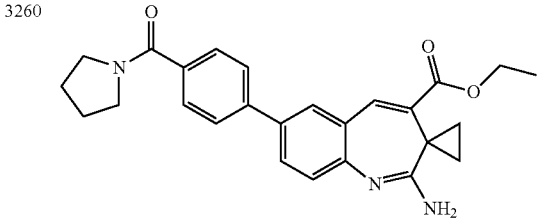
2931 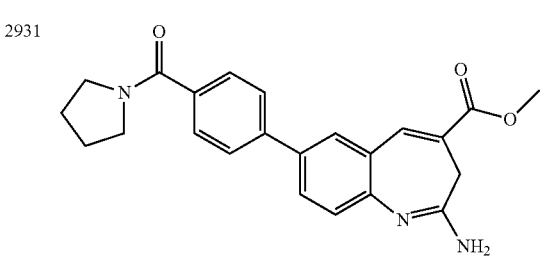
2984 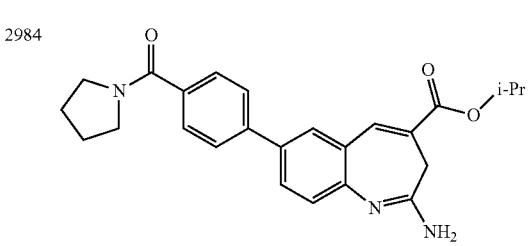
2986 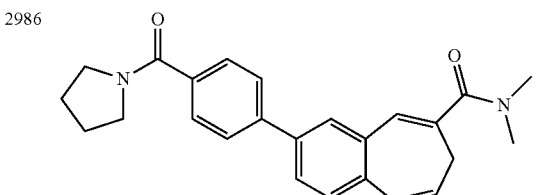

TABLE 1B-continued

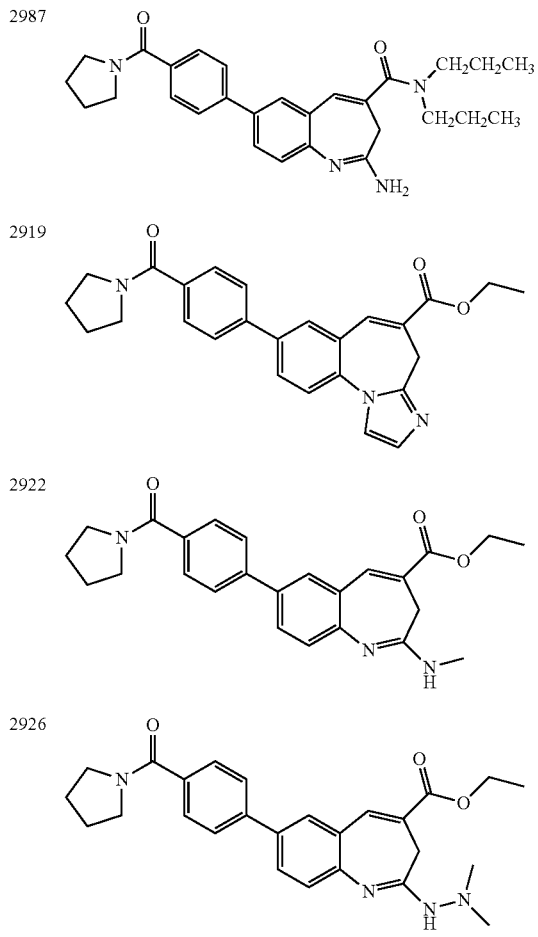

In one aspect, the invention includes a compound, or salt thereof, with an $IC_{50}$ value ≤25 µM for TLR8. In another aspect, the invention includes a compound or salt thereof, with an $IC_{50}$ value ≤15 µM for TLR8. In another aspect, the invention includes a compound or salt thereof, with an $IC_{50}$ value ≤10 µM for TLR8. In another aspect, the invention includes a compound or salt thereof, with an $IC_{50}$ value ≤7.5 µM for TLR8. In another aspect, the invention includes a compound or salt thereof, with an $IC_{50}$ value ≤5 µM for TLR8. In another aspect, the invention includes a compound or salt thereof, with an $IC_{50}$ value ≤2.5 µM for TLR8. In another aspect, the invention includes a compound or salt thereof, with an $IC_{50}$ value ≤1.5 µM for TLR8. In another aspect, the invention includes a compound or salt thereof, with an $IC_{50}$ value ≤1 µM for TLR8. In another aspect, the invention includes a compound or salt thereof, with an $IC_{50}$ value ≤0.5 µM for TLR8. In another aspect, the invention includes a compound or salt thereof, with an $IC_{50}$ value ≤0.25 µM for TLR8. In another aspect, the invention includes a compound or salt thereof, with an $IC_{50}$ value ≤0.1 µM for TLR8. In another aspect, the invention includes a compound or salt thereof, with an $IC_{50}$ value ≤0.01 µM for TLR8. In another aspect, the invention includes a compound or salt thereof, with an $IC_{50}$ value ≤0.001 µM for TLR8.

In one aspect, the invention includes a compound, or salt thereof, with an $IC_{50}$ value ≤25 µM for TLR7. In another aspect, the invention includes a compound or salt thereof, with an $IC_{50}$ value ≤15 µM for TLR7. In another aspect, the invention includes a compound or salt thereof, with an $IC_{50}$ value ≤10 µM for TLR7. In another aspect, the invention includes a compound or salt thereof, with an $IC_{50}$ value ≤7.5 µM for TLR7. In another aspect, the invention includes a compound or salt thereof, with an $IC_{50}$ value ≤5 µM for TLR7. In another aspect, the invention includes a compound or salt thereof, with an $IC_{50}$ value ≤2.5 µM for TLR7. In another aspect, the invention includes a compound or salt thereof, with an $IC_{50}$ value ≤1.5 µM for TLR7. In another aspect, the invention includes a compound or salt thereof, with an $IC_{50}$ value ≤1 µM for TLR7. In another aspect, the invention includes a compound or salt thereof, with an $IC_{50}$ value ≤0.5 µM for TLR7. In another aspect, the invention includes a compound or salt thereof, with an $IC_{50}$ value ≤0.25 µM for TLR7. In another aspect, the invention includes a compound or salt thereof, with an $IC_{50}$ value ≤0.1 µM for TLR7. In another aspect, the invention includes a compound or salt thereof, with an $IC_{50}$ value ≤0.01 µM for TLR7. In another aspect, the invention includes a compound or salt thereof, with an $IC_{50}$ value ≤0.001 µM for TLR7.

In one aspect, the invention does not include a compound or salt thereof, with an $IC_{50}$>25 µM for TLR7. In one aspect, the invention does not include a compound or salt thereof, with an $IC_{50}$>25 µM for TLR8. In one aspect, the invention does not include a compound or salt thereof, with an $IC_{50}$ value >25 µM for TLR7 and for TLR8.

In one embodiment, the TLR7, TLR8, or TLR7/8 antagonist activity of a compound of the invention is measured relative to the activity of a known TLR7, TLR8, or TLR7/8 agonist. See, for example, compounds described in PCT publication WO 2007/024612.

The term "compound of the invention" refers to exemplified compounds and compounds covered under the formulae described herein.

The term "substituted," as used herein, means that any one or more hydrogen atoms on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

A chemical structure showing a dashed line representation for a chemical bond indicates that the bond is optionally present. For example, a dashed line drawn next to a solid single bond indicates that the bond can be either a single bond or a double bond.

The term "alkyl" as used herein refers to a saturated linear or branched-chain monovalent hydrocarbon radical having one to twelve, including one to ten carbon atoms ($C_1$-$C_{10}$), one to six carbon atoms ($C_1$-$C_6$) and one to four carbon atoms ($C_1$-$C_4$), wherein the alkyl radical may be optionally substituted independently with one or more substituents described below. Lower alkyl means an alkyl group having one to six carbon atoms ($C_1$-$C_6$). Examples of alkyl radicals include hydrocarbon moieties such as, but not limited to: methyl(Me, —$CH_3$), ethyl(Et, —$CH_2CH_3$), 1-propyl(n-Pr, n-propyl, —$CH_2CH_2CH_3$), 2-propyl(i-Pr, i-propyl, —$CH(CH_3)_2$), 1-butyl(n-Bu, n-butyl, —$CH_2CH_2CH_2CH_3$), 2-methyl-1-propyl(i-Bu, i-butyl, —$CH_2CH(CH_3)_2$), 2-butyl (s-Bu, s-butyl, —$CH(CH_3)CH_2CH_3$), 2-methyl-2-propyl(t-Bu, t-butyl, —$C(CH_3)_3$), 1-pentyl(n-pentyl, —$CH_2CH_2CH_2CH_2CH_3$), 2-pentyl (—$CH(CH_3)$ $CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)$ $CH(CH_3)_2$), 3-methyl-1-butyl (—$CH_2CH_2CH(CH_3)_2$), 2-methyl-1-butyl (—CH₂CH(CH₃)CH₂CH₃), 1-hexyl (—CH₂CH₂CH₂CH₂CH₂CH₃), 2-hexyl (—CH(CH₃) CH₂CH₂CH₂CH₃), 3-hexyl (—CH(CH₂CH₃) (CH₂CH₂CH₃)), 2-methyl-2-pentyl (—C(CH₃)₂ CH₂CH₂CH₃), 3-methyl-2-pentyl (—CH(CH₃)CH(CH₃) CH₂CH₃), 4-methyl-2-pentyl (—CH(CH₃)CH₂CH(CH₃)₂), 3-methyl-3-pentyl (—C(CH₃)(CH₂CH₃)₂), 2-methyl-3-pentyl (—CH(CH₂CH₃)CH(CH₃)₂), 2,3-dimethyl-2-butyl (—C (CH₃)₂CH(CH₃)₂), 3,3-dimethyl-2-butyl (—CH(CH₃)C (CH₃)₃, 1-heptyl, and 1-octyl.

Moieties replacing a hydrogen atom on a "substituted" radical include, for example, halogen, lower alkyl, lower alkoxy, keto, amino, alkylamino, dialkylamino, trifluoromethyl, aryl, heteroaryl and hydroxyl.

The term "alkenyl" refers to a linear or branched-chain monovalent hydrocarbon radical having two to 10 carbon atoms ($C_2$-$C_{10}$), including two to six carbon atoms ($C_2$-$C_6$) and two to four carbon atoms ($C_2$-$C_4$), and at least one double bond, and includes, but is not limited to, ethenyl, propenyl, 1-but-3-enyl, 1-pent-3-enyl, 1-hex-5-enyl and the like, wherein the alkenyl radical may be optionally substituted independently with one or more substituents described herein, and includes radicals having "cis" and "trans" orientations, or alternatively, "E" and "Z" orientations. The term "alkenyl" includes allyl.

The term "alkynyl" refers to a linear or branched monovalent hydrocarbon radical of two to twelve carbon atoms ($C_2$-$C_{12}$), including two to 10 carbon atoms ($C_2$-$C_{10}$), two to six carbon atoms ($C_2$-$C_6$) and two to four carbon atoms ($C_2$-$C_4$), containing at least one triple bond. Examples include, but are not limited to, ethynyl, propynyl, butynyl, pentyn-2-yl and the like, wherein the alkynyl radical may be optionally substituted independently with one or more substituents described herein.

The term "carbonylamino" refers to —NHCOR or —NHCOOR, in which R is H, alkyl, carbocycle, heterocyclyl, amino, or other moieties described herein.

The terms "carbocycle," "carbocyclyl," or "cycloalkyl" are used interchangeably herein and refer to saturated or partially unsaturated cyclic hydrocarbon radical having from three to twelve carbon atoms ($C_3$-$C_{12}$), including from three to ten carbon atoms ($C_3$-$C_{10}$) and from three to six carbon atoms ($C_3$-$C_6$). The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like. Bicyclic carbocycles have 7 to 12 ring atoms, e.g. arranged as a bicyclo[4,5], [5,5], [5,6] or [6,6] system, or 9 or 10 ring atoms arranged as a bicyclo[5,6] or [6,6] system, or as bridged systems such as bicyclo[2.2.1]heptane, bicyclo [2.2.2]octane, and bicyclo[3.2.2]nonane. The cycloalkyl may be optionally substituted independently at one or more substitutable positions with one or more substituents described herein. Such cycloalkyl groups may be optionally substituted with, for example, one or more groups independently selected from $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl and di($C_1$-$C_6$)alkylamino($C_1$-$C_6$)alkyl.

The terms "heterocycloalkyl," "heterocycle" and "heterocyclyl" are used interchangeably herein and refer to a saturated or partially unsaturated carbocyclic radical of 3 to 8 ring atoms in which at least one ring atom is a heteroatom selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. The term further includes fused ring systems which include a heterocycle fused to an aromatic group. "Heterocycloalkyl" also includes radicals where heterocycle radicals are fused with aromatic or heteroaromatic rings. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo [4.1.0]heptanyl, azabicyclo[2.2.2]hexanyl, 3H-indolyl quinolizinyl and N-pyridyl ureas. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N attached) or imidazol-3-yl (C-attached). An example of a heterocyclic group wherein 2 ring carbon atoms are substituted with oxo (=O) moieties is 1,1-dioxo-thiomorpholinyl. The heterocycle groups herein are unsubstituted or, as specified, substituted in one or more substitutable positions with various groups. For example, such heterocycle groups may be optionally substituted with, for example, one or more groups independently selected from $C_1$-$C_6$ alkyl, $C_1$-$C_6$ alkoxy, halogen, hydroxy, cyano, nitro, amino, mono($C_1$-$C_6$)alkylamino, di($C_1$-$C_6$6)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The term "aryl" refers to a monovalent aromatic carbocyclic radical having a single ring (e.g., phenyl), multiple rings (e.g., biphenyl), or multiple condensed rings in which at least one is aromatic, (e.g., 1,2,3,4-tetrahydronaphthyl, naphthyl, etc.), which is optionally substituted with one or more substituents independently selected from, for example, halogen, lower alkyl, lower alkoxy, trifluoromethyl, aryl, heteroaryl and hydroxy.

The term "heteroaryl" refers to a monovalent aromatic radical of 5-, 6-, or 7-membered rings and includes fused ring systems (at least one of which is aromatic) of 5-10 atoms containing at least one and up to four heteroatoms selected from nitrogen, oxygen, and sulfur. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, isobenzofuran-1(3H)-one, and furopyridinyl. Spiro moieties are also included within the scope of this definition. Heteroaryl groups are optionally substituted with one or more substituents independently selected from, for example, halogen, lower alkyl, lower alkoxy, haloalkyl, aryl, heteroaryl, and hydroxy.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures, pure diastereomers and pure enantiomers of the compounds.

Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. Enantiomers can also be separated by use of a chiral HPLC column. Methods for the determination of stereochemistry and the separation of stereoisomers are well known in the art (see discussion in Chapter 4 of "Advanced Organic Chemistry", 4th edition, J. March, John Wiley and Sons, New York, 1992).

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

A single stereoisomer, e.g. an enantiomer, substantially free of its stereoisomer may be obtained by resolution of the racemic mixture using a method such as formation of diastereomers using optically active resolving agents (Eliel, E. and Wilen, S. Stereochemistry of Organic Compounds, John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Drug Stereochemistry, Analytical Methods and Pharmacology, Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, a-methyl-13-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, for example a menthyl ester such as (-) menthyl chloroformate, in the presence of base, or Mosher ester, a-methoxy-a-(trifluoromethyl)phenyl acetate (Jacob III, (1982) J. Org. Chem. 47:4165), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (Chiral Liquid Chromatography (1989) W. J. Lough, Ed., Chapman and Hall, New York; Okamoto, (1990) J. of Chromatogr. 513:375-378). Enriched or purified enantiomers can be distinguished by methods used to distinguish other chiral molecules with asymmetric carbon atoms, such as optical rotation and circular dichroism.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

In addition to compounds of the invention, the invention also includes pharmaceutically acceptable salts of such compounds.

A "pharmaceutically acceptable salt," unless otherwise indicated, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Examples of pharmaceutically acceptable salts include those salts prepared by reaction of the compounds of the present invention with a mineral or organic acid or an inorganic base, such salts including sulfates, pyrosulfates, bisulfates, sulfites, bi sulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, pheylacetates, phenylpropionates, phenylbutyrates, citrates, lactates, y-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moiety, the compounds of the present invention may include mono, di or tri-salts in a single compound.

If the inventive compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Examples of suitable inorganic salts include those formed with alkali and alkaline earth metals such as lithium, sodium, potassium, barium and calcium. Examples of suitable organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine.

The present invention also provides salts of compounds of the invention which are not necessarily pharmaceutically acceptable salts, but which may be useful as intermediates for preparing and/or purifying compounds of the invention and/or for separating enantiomers of compounds of the invention.

It is noted that some of the preparations of compounds of the invention described herein may require protection of remote functionalities. The need for such protection will vary depending on the nature of the functionality and the conditions used in the preparation methods and can be readily determined by those skilled in the art. Such protection/deprotection methods are well known to those skilled in the art.

The compounds of the invention find use in a variety of applications. For example, in certain aspects the invention provides methods for modulating TLR7- and/or TLR8-mediated signaling. The methods of the invention are useful, for example, when it is desirable to alter TLR7- and/or TLR8-mediated signaling in response to a suitable TLR7 and/or TLR8 ligand or a TLR7 and/or TLR8 signaling agonist.

As used herein, the terms "TLR7 and/or TLR8 ligand," "ligand for TLR7 and/or TLR8," and "TLR7 and/or TLR8 signaling agonist" refer to a molecule, other than a compound of the invention, that interacts directly or indirectly with TLR7 and/or TLR8 and induces TLR7- and/or TLR8-mediated signaling. In certain embodiments, a TLR7 and/or TLR8 ligand is a natural ligand, i.e., a TLR7 and/or TLR8 ligand that is found in nature. In certain embodiments, a TLR7 and/or TLR8 ligand refers to a molecule other than a natural ligand of TLR7 and/or TLR8, e.g., a molecule prepared by human activity.

The term "modulate" as used herein with respect to the TLR7 and/or TLR8 receptors means the mediation of a pharmacodynamic response in a subject by (i) inhibiting the receptor, or (ii) directly or indirectly affecting the normal regulation of the receptor activity.

The term "agonist" refers to a compound that, in combination with a receptor (e.g., a TLR), can produce a cellular response. An agonist may be a ligand that directly binds to the receptor. Alternatively, an agonist may combine with a receptor indirectly by, for example, (a) forming a complex with another molecule that directly binds to the receptor, or (b) otherwise resulting in the modification of another compound so that the other compound directly binds to the receptor. An agonist may be referred to as an agonist of a particular TLR (e.g., a TLR7 and/or TLR8 agonist). The term "partial agonist" refers to a compound that produces a partial but not a full cellular response.

The term "antagonist" as used herein refers to a compound that competes with an agonist or partial agonist for binding to a receptor, thereby blocking the action of an agonist or partial agonist on the receptor. More specifically, an antagonist is a compound that inhibits the activity of a TRL7 or TLR8 agonist at the TLR7 or TLR8 receptor, respectively. "Inhibit" refers to any measurable reduction of biological activity. Thus, as used herein, "inhibit" or "inhibition" may be referred to as a percentage of a normal level of activity.

In one aspect of this invention, a method of treating or preventing a condition or disorder treatable by modulation of TLR7- and/or TLR8-mediated cellular activities in a subject comprises administering to said subject a composition comprising a compound of the invention in an amount effective to treat or prevent the condition or disorder. The term "TLR7- and/or TLR8-mediated" refers to a biological or biochemical activity that results from TLR7- and/or TLR8 function.

Conditions and disorders that can be treated by the methods of this invention include, but are not limited to, cancer, immune complex-associated diseases, autoimmune diseases or disorders, inflammatory disorders, immunodeficiency, graft rejection, graft-versus-host disease, allergies, cardiovascular disease, fibrotic disease, asthma, infection, and sepsis. More specifically, methods useful in the treatment of these conditions will employ compounds of the invention that inhibit TLR7- and/or TLR8-mediated signaling. In some instances the compositions can be used to inhibit TLR7- and/or TLR8-mediated signaling in response to a TLR7 and/or TLR8 ligand or signaling agonist. In other instances the compositions can be used to inhibit TLR7- and/or TLR8-mediated immunostimulation in a subject.

The term "treating" as used herein, unless otherwise indicated, means at least the mitigation of a disease or condition and includes, but is not limited to, modulating and/or inhibiting an existing disease or condition, and/or alleviating the disease or condition to which such term applies, or one or more symptoms of such disease or condition. The term "treatment," as used herein, unless otherwise indicated, refers to the act of treating as "treating" is defined immediately above. Therapeutic treatment refers to treatment initiated after observation of symptoms and/or a suspected exposure to a causative agent of the disease or condition. Generally, therapeutic treatment may reduce the severity and/or duration of symptoms associated with the disease or condition.

As used herein, "preventing" means causing the clinical symptoms of a disease or condition not to develop i.e., inhibiting the onset of a disease or condition in a subject that may be exposed to or predisposed to the disease or condition, but does not yet experience or display symptoms of the disease or condition. Prophylactic treatment means that a compound of the invention is administered to a subject prior to observation of symptoms and/or a suspected exposure to a causative agent of the condition (e.g., a pathogen or carcinogen). Generally, prophylactic treatment may reduce (a) the likelihood that a subject that receives the treatment develops the condition and/or (b) the duration and/or severity of symptoms in the event the subject develops the condition.

As used herein, the terms "autoimmune disease," "autoimmune disorder" and "autoimmunity" refer to immunologically mediated acute or chronic injury to a tissue or organ derived from the host. The terms encompass both cellular and antibody-mediated autoimmune phenomena, as well as organ-specific and organ-nonspecific autoimmunity. Autoimmune diseases include insulin-dependent diabetes mellitus, rheumatoid arthritis, systemic lupus erythematosus, multiple sclerosis, atherosclerosis, and inflammatory bowel disease. Autoimmune diseases also include, without limitation, ankylosing spondylitis, autoimmune hemolytic anemia, Bechet's syndrome, Goodpasture's syndrome, Graves' disease, Guillain Barre syndrome, Hashimoto's thyroiditis, idiopathic thrombocytopenia, myasthenia gravis, pernicious anemia, polyarteritis nodosa, polymyositis/dermatomyositis, primary biliary sclerosis, psoriasis, sarcoidosis, sclerosing cholangitis, Sjogren's syndrome, systemic sclerosis (scleroderma and CREST syndrome), Takayasu's arteritis, temporal arteritis, and Wegener's granulomatosis. Autoimmune diseases also include certain immune complex-associated diseases.

As used here in, the term "fibrotic disease" refers to diseases or disorders involving excessive and persistent formation of scar tissue associated with organ failure in a variety of chronic diseases affecting the lungs, kidneys, eyes, heart, liver, and skin. Although tissue remodeling and scarring is part of the normal wound healing process, repeated injury or insult can lead to persistent and excessive scarring and, ultimately, organ failure.

Fibrotic conditions include diffuse fibrotic lung disease, chronic kidney disease, including diabetic kidney disease; liver fibrosis (e.g., chronic liver disease (CLD) caused by continuous and repeated insults to the liver from causes such as are viral hepatitis B and C, alcoholic cirrhosis or non-alcoholic fatty liver disease (NAFLD), or primary sclerosing cholangitis (PSC), a rare disease characterized by fibrosing inflammatory destruction of the bile ducts inside and outside the liver, leading to bile stasis, liver fibrosis, and ultimately to cirrhosis, and end-stage liver disease); lung fibrosis (e.g., idiopathic pulmonary fibrosis (IPF)); and systemic sclerosis (a degenerative disorder in which excessive fibrosis occurs in multiple organ systems, including the skin, blood vessels, heart, lungs, and kidneys).

Other examples include cystic fibrosis of the pancreas and lungs; injection fibrosis, which can occur as a complication of intramuscular injections, especially in children; endomyocardial fibrosis; mediastinal fibrosis, myelofibrosis; retroperitoneal fibrosis; progressive massive fibrosis, a complication of coal workers' pneumoconiosis; nephrogenic systemic fibrosis; and complication of certain types of surgical implants (e.g. occurrence in attempts at creating an artificial pancreas for the treatment of diabetes mellitus.

As used herein, the term "cardiovascular disease" refers to diseases or disorders of the cardiovascular system involving an imflammatory component, and/or the accumulation of plaque, including without limitation coronary artery disease, cerebrovascular disease, peripheral arterial disease, atherosclerosis, and arteriosclerosis.

As used herein, the terms "cancer" and, "tumor" refer to a condition in which abnormally replicating cells of host origin are present in a detectable amount in a subject. The cancer can be a malignant or non-malignant cancer. Cancers or tumors include, but are not limited to, biliary tract cancer; brain cancer; breast cancer; cervical cancer; choriocarcinoma; colon cancer; endometrial cancer; esophageal cancer; gastric (stomach) cancer; intraepithelial neoplasms; leukemias; lymphomas; liver cancer; lung cancer (e.g., small cell and non-small cell); melanoma; neuroblastomas; oral cancer; ovarian cancer; pancreatic cancer; prostate cancer; rectal cancer; renal (kidney) cancer; sarcomas; skin cancer; testicular cancer; thyroid cancer; as well as other carcinomas and sarcomas. Cancers can be primary or metastatic.

As used herein, the terms "inflammatory disease" and inflammatory disorder" refer to a condition characterized by inflammation e.g., a localized protective reaction of tissue to irritation, injury, or infection, characterized by pain, redness, swelling, and sometimes loss of function. Inflammatory diseases or disorders include e.g., allergy, asthma, and allergic rash.

As used herein, the term "immune complex-associated disease" refers to any disease characterized by the production and/or tissue deposition of immune complexes (i.e., any conjugate including an antibody and an antigen specifically bound by the antibody), including, but not limited to systemic lupus erythematosus (SLE) and related connective tissue diseases, rheumatoid arthritis, hepatitis C- and hepatitis B-related immune complex disease (e.g., cryoglobulinemia), Bechet's syndrome, autoimmune glomerulonephritides, and vasculopathy associated with the presence of LDL/anti-LDL immune complexes.

As used herein, "immunodeficiency" refers to a disease or disorder in which the subject's immune system is not functioning in normal capacity or in which it would be useful to boost a subject's immune response, for example to eliminate a tumor or cancer (e.g., tumors of the brain, lung (e.g., small cell and non-small cell), ovary, breast, prostate, colon, as well as other carcinomas and sarcomas) or an infection in a subject. The immunodeficiency can be acquired or it can be congenital.

As used herein, "graft rejection" refers to immunologically mediated hyperacute, acute, or chronic injury to a tissue or organ derived from a source other than the host. The term thus encompasses both cellular and antibody-mediated rejection, as well as rejection of both allografts and xenografts.

"Graft-versus-host disease" (GvHD) is a reaction of donated bone marrow against a patient's own tissue. GVHD is seen most often in cases where the blood marrow donor is unrelated to the patient or when the donor is related to the patient but not a perfect match. There are two forms of GVHD: an early form called acute GVHD that occurs soon after the transplant when the white cells are on the rise and a late form called chronic GVHD.

$T_{H2}$-mediated, atopic diseases include, but are not limited to, atopic dermatitis or eczema, eosinophilia, asthma, allergy, allergic rhinitis, and Ommen's syndrome.

As used herein, "allergy" refers to acquired hypersensitivity to a substance (allergen). Allergic conditions include eczema, allergic rhinitis or coryza, hay fever, asthma, urticaria (hives) and food allergies, and other atopic conditions As used herein, "asthma" refers to a disorder of the respiratory system characterized by inflammation, narrowing of the airways and increased reactivity of the airways to inhaled agents. Asthma is frequently, although not exclusively associated with atopic or allergic symptoms. For example, asthma can be precipitated by exposure to an allergen, exposure to cold air, respiratory infection, and exertion.

As used herein, the terms "infection" and, equivalently, "infectious disease" refer to a condition in which an infectious organism or agent is present in a detectable amount in the blood or in a normally sterile tissue or normally sterile compartment of a subject. Infectious organisms and agents include viruses, bacteria, fungi, and parasites. The terms encompass both acute and chronic infections, as well as sepsis.

As used herein, the term "sepsis" refers to the presence of bacteria (bacteremia) or other infectious organisms or their toxins in the blood (septicemia) or in other tissue of the body.

Further provided is a compound of the invention, or a salt thereof, for use as a medicament in the treatment of the diseases or conditions described above in a mammal, for example, a human, suffering from such disease or condition. Also provided is the use of a compound of the invention, or a salt thereof, in the preparation of a medicament for the treatment of the diseases and conditions described above in a mammal, for example a human, suffering from such disorder.

This invention also encompasses pharmaceutical compositions containing a compound of the invention and methods of treating or preventing conditions and disorders by modulation of TLR7- and/or TLR8-mediated cellular activities by administering a pharmaceutical composition comprising a compound of the invention, or a salt thereof, to a patient in need thereof.

In order to use a compound of the invention or a salt thereof for the therapeutic treatment (including prophylactic treatment) of mammals including humans, it is normally formulated in accordance with standard pharmaceutical practice as a pharmaceutical composition.

According to this aspect of the invention there is provided a pharmaceutical composition that comprises a compound of the invention, or a salt thereof, as defined hereinbefore in association with a pharmaceutically acceptable diluent or carrier.

To prepare the pharmaceutical compositions according to this invention, a therapeutically or prophylactically effective amount of a compound of the invention or a salt thereof (alone or together with an additional therapeutic agent as disclosed herein) is intimately admixed, for example, with a pharmaceutically acceptable carrier according to conventional pharmaceutical compounding techniques to produce a dose. A carrier may take a wide variety of forms depending on the form of preparation desired for administration, e.g., oral or parenteral. Examples of suitable carriers include any and all solvents, dispersion media, adjuvants, coatings, antibacterial and antifungal agents, isotonic and absorption delaying agents, sweeteners, stabilizers (to promote long term storage), emulsifiers, binding agents, thickening agents, salts, preservatives, solvents, dispersion media, coatings, antibacterial and antifungal agents, isotonic and absorption delaying agents, flavoring agents, and miscellaneous materials such as buffers and absorbents that may be needed in order to prepare a particular therapeutic composition. The use of such media and agents with pharmaceutically active substances is well known in the art. Except insofar as any conventional media or agent is incompatible with a compound of the invention, its use in the therapeutic compositions and preparations is contemplated. Supplementary active ingredients can also be incorporated into the compositions and preparations as described herein.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above.

Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. For parenteral formulations, the carrier will usually comprise sterile water, aqueous sodium chloride solution, 1,3-butanediol, or any other suitable non toxic parenterally acceptable diluent or solvent. Other ingredients including those that aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 micron or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

Compositions for transdermal administration may be in the form of those transdermal skin patches that are well known to those of ordinary skill in the art. Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Compositions may be administered in the form of a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's Pharmaceutical Sciences, Ed. By Arthur Osol, p. 1445 (1980)). Of course, the ordinary artisan can readily determine a suitable saline content and pH for an innocuous aqueous carrier for nasal administration.

Other, non-limiting examples of intranasal dosage forms containing the composition include nasal gels, creams, pastes or ointments with a viscosity of, e.g., from about 10 to about 3000 cps, or from about 2500 to 6500 cps, or greater, which may provide a more sustained contact with the nasal mucosal surfaces. Such carrier viscous formulations may be based upon, simply by way of example, polymeric carriers such as alkylcelluloses and/or other biocompatible carriers of high viscosity well known to the art (see e.g., Remington's, cited supra). The carrier containing the composition may also be soaked into a fabric material, such as gauze, that can be applied to the nasal mucosal surfaces to allow for active substances in the isolated fraction to penetrate to the mucosa.

Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation.

Further, for nasal administration of solutions or suspensions of the composition, various devices are available in the art for the generation of drops, droplets and sprays. For example, solutions comprising the isolated fraction can be administered into the nasal passages by means of a simple dropper (or pipet) that includes a glass, plastic or metal dispensing tube from which the contents are expelled drop by drop by means of air pressure provided by a manually powered pump, e.g., a flexible rubber bulb, attached to one end. Fine droplets and sprays can be provided by a manual or electrically powered intranasal pump dispenser or squeeze bottle as well known to the art, e.g., that is designed to blow a mixture of air and fine droplets into the nasal passages.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. However, an effective dosage is in the range of about 0.001 to about 100 mg per kg body weight per day, for example, about 0.05 to about 35 mg/kg/day, in single or divided doses. For a 70 kg human, a dosage is about 0.0005 to 2.5 g/day. For example a dosage is about 0.0005 to about 1 g/day. In some instances, dosage levels below the lower limit of the aforesaid range may be more than adequate, while in other cases still larger doses may be employed without causing any harmful side effect, provided that such larger doses are first divided into several small doses for administration throughout the day.

For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

The size of the dose for therapeutic or prophylactic purposes of a compound of the invention will naturally vary according to the nature and severity of the conditions, the age and sex of the animal or patient and the route of administration, according to well known principles of medicine. It will be understood that the specific dosage level and frequency of dosage for any particular subject may be varied and will depend upon a variety of factors including the activity of the specific compound of the invention, the species, age, body weight, general health, sex and diet of the subject, the mode and time of administration, rate of excretion, drug combination, and severity of the particular condition, but can nevertheless be routinely determined by one skilled in the art.

A compound of the invention or salt thereof, is in some aspects administered to a subject in combination (e.g., in the same formulation or in separate formulations) with another therapeutic agent ("combination therapy"). The compound of the invention is administered in admixture with another therapeutic agent or is administered in a separate formulation. When administered in separate formulations, a compound of the invention and another therapeutic agent is administered substantially simultaneously or sequentially. In one aspect, a compound of the invention is administered to a subject in combination with another therapeutic agent for treating a condition or disease. In one aspect, a compound of the invention is administered to a subject in combination with another therapeutic agent for preventing a condition or disease. In one aspect, a compound of the invention is administered to a subject in combination with a vaccine for preventing a condition or disease. In one aspect, a compound of the invention is administered to a subject in combination with an infectious disease vaccine. In one aspect, a compound of the invention is administered to a subject in combination with a cancer vaccine.

A compound of the invention may also be helpful in individuals having compromised immune function. For example, a compound of the invention may be used for treating or preventing the opportunistic infections and tumors that occur after suppression of cell mediated immunity in, for example, transplant patients, cancer patients and HIV patients.

Such combination treatment may involve, in addition to a compound of the invention, conventional surgery or radiotherapy or chemotherapy. Such chemotherapy may include one or more of the following categories of anti-tumor agents: (i) antiproliferative/anti-neoplastic drugs and combinations thereof; (ii) cytostatic agents; (iii) agents which inhibit cancer cell invasion; (iv) inhibitors of growth factor function; (v) antiangiogenic agents; (vi) vascular damaging agents; (vii) antisense therapies; (viii) gene therapy approaches; (ix) interferon; and (x) immunotherapy approaches.

Therapeutic agents for treating or preventing respiratory diseases which may be administered in combination with a compound of the invention in a subject method include, but are not limited to beta adrenergics which include bronchodilators including albuterol, isoproterenol sulfate, metaproterenol sulfate, terbutaline sulfate, pirbuterol acetate and sahneterol formotorol; steroids including beclomethasone dipropionate, flunisolide, fluticasone, budesonide and triamcinolone acetonide. Anti-inflammatory drugs used in connection with the treatment or preventing of respiratory diseases include steroids such as beclomethasone dipropionate, triamcinolone acetonide, flunisolide and fluticasone. Other anti-inflammatory drugs include cromoglycates such as cromolyn sodium. Other respiratory drugs which would qualify as bronchodilators include anticholenergics including ipratropium bromide. Antihistamines include, but are not limited to, diphenhydramine, carbinox amine, clemastine, dimenhydrinate, pryilamine, tripelennamine, chlorpheniramine, brompheniramine, hydroxyzine, cyclizine, meclizine, chlorcyclizine, promethazine, doxylamine, loratadine, and terfenadine. Particular antihistamines include rhinolast (Astelin®), claratyne (Claritin®), claratyne D (Claritin D®), telfast (Allegra®), Zyrtec®, and beconase.

In some embodiments, a compound of the invention is administered as a combination therapy with interferon-gamma (IFN-gamma), a corticosteroid such as prednisone, prednisolone, methyl prednisolone, hydrocortisone, cortisone, dexamethasone, betamethasone, etc., or a combination thereof, for the treatment or preventing of interstitial lung disease, e.g., idiopathic pulmonary fibrosis.

In some embodiments, a compound of the invention is administered in combination therapy with a known therapeutic agent used in the treatment of cystic fibrosis ("CF"). Therapeutic agents used in the treatment of CF include, but are not limited to, antibiotics; anti-inflammatory agents; DNAse (e.g., recombinant human DNAse; pulmozyme; dornase alfa); mucolytic agents (e.g., N-acetylcysteine; Mucomyst™; Mucosil™); decongestants; bronchodilators (e.g., theophylline; ipatropium bromide); and the like.

In some embodiments, a compound of the invention is administered prophylatically for the prevention of cardiovascular disease e.g., atherosclerosis.

In another embodiment of the invention, an article of manufacture, or "kit", containing materials useful for the treatment or prevention of the diseases described above is provided.

In one embodiment, the kit comprises a container comprising a composition of the invention, or pharmaceutically acceptable salt thereof. In one embodiment, the invention provides a kit for treating or preventing a TLR7- and/or TLR8-mediated disorder. In another embodiment, the invention provides a kit for a condition or disorder treatable by selective modulation of the immune system in a subject. The kit may further comprise a label or package insert on or associated with the container. Suitable containers include, for example, bottles, vials, syringes, blister pack, etc. The container may be formed from a variety of materials such as glass or plastic. The container holds a compound of the invention or a pharmaceutical formulation thereof in an amount effective for treating or preventing the condition, and may have a sterile access port (for example, the container may be an intravenous solution bag or a vial having a stopper pierceable by a hypodermic injection needle). The label or package insert indicates that the composition is used for treating or preventing the condition of choice. In one embodiment, the label or package inserts indicates that the composition comprising a compound of the invention can be used, for example, to treat or prevent a disorder treatable by modulation of TLR7- and/or TLR8-mediated cellular activities. The label or package insert may also indicate that the composition can be used to treat or prevent other disorders. Alternatively, or additionally, the kit may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of the invention and, if present, the second pharmaceutical formulation. For example, if the kit comprises a first composition comprising a compound of the invention and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of the invention, such as tablets or capsules. Such a kit includes, for example, a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, the kit may comprise (a) a first container with a compound of the invention contained therein; and optionally (b) a second container with a second pharmaceutical formulation contained therein, wherein the second pharmaceutical formulation comprises a second compound which may be effective in treating or preventing a condition or disorder by selective modulation of TLR7- and/or TLR8-mediated cellular activities. Alternatively, or additionally, the kit may further comprise a third container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a pharmaceutical formulation of a compound of the invention and a second formulation comprising a second therapeutic agent, the kit may comprise a container for containing the separate formulations, such as a divided bottle or a divided foil packet; however, the separate compositions may also be contained within a single, undivided container. Typically, the kit comprises directions for the administration of the separate components. The kit form is particularly advantageous when the separate components are administered in different dosage forms (e.g., oral and parenteral), are administered at different dosage intervals, or when titration of the individual components of the combination is desired by the prescribing physician.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of the present invention can be prepared in a variety of ways using commercially available starting materials, compounds known in the literature, or from readily prepared inteimmediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* $5^{th}$ edition, John Wiley & Sons: New York, 2001; and Greene, T. W., Wuts, P. G. M., *Protective Groups in Organic Synthesis,* $3^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of this invention with each of the formulae described herein may be prepared according to the following procedures from commercially available starting materials or starting materials which can be prepared using literature procedures. These procedures show the preparation of representative compounds of this invention.

Characterization of Compounds of the Invention

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

In order to illustrate the invention, the following examples are included. However, it is to be understood that these examples do not limit the invention and are only meant to suggest a method of practicing the invention.

Example 1 Synthetic Procedures

Abbreviations Used:
RT: room temperature
SM: starting material
LC: liquid chromatography
LCMS: liquid chromatography-mass spectrometry
HPLC: high performance liquid chromatography
TLC: thin layer chromatography
NMR: nuclear magnetic resonance
DCM: dichloromethane
MeOH: methanol
EtOH: ethanol
EtOAc: ethyl acetate
TFA: trifluoroacetic acid
MTBE: methyl tert-butyl ether
AcOH: acetic acid
HOBt: 1-hydroxybenzotriazole Synthesis of Compound 3173

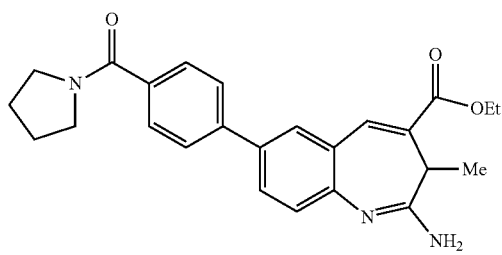 [SMILES: CCOC(=O)C1=Cc2cc(-c3ccc(C(=O)N4CCCC4)cc3)ccc2N=C(N)C1C]

Ethyl 2-amino-3-methyl-7-[4-(pyrrolidin-1-ylcarbonyl)phenyl]-3H-1-benzazepine-4-carboxylate Ethyl 2-amino-7-bromo-3-methyl-3H-1-benzazepine-4-carboxylate (0.351 g, 0.988 mmol), 4-(pyrrolidin-1-ylcarbonyl)phenylboronic acid (0.325 g, 1.48 mmol), cesium carbonate (0.48 g, 1.5 mmol), water (1.4 mL), ethanol (0.36 mL), and toluene (3.51 mL) were combined at room temperature and degassed by bubbling $N_2$ through the slurrry for 20 min. Tetrakis(triphenylphosphine)palladium(0) (0.018 g, 0.016 mmol) was added and degassing continued for 5 min. The mixture was heated to 80° C. overnight. LC shows some reaction but mostly SM present. The mixture was treated with an additional 50 mg of catalyst and heating continued overnight. LCMS now showed complete reaction. The crude product was isolated with EtOAc after pouring into water. The crude was chromatographed on silica gel with 1000:125:10 DCM:MeOH:ammonia. This gave about 400 mg of crude oil which was taken up in EtOAc to crystallize the product. LC showed not pure enough, so it was recrystallized from EtOAc by taking the solids up in DCM and evaporating off the DCM. This resulted in slow crystallization to give 74 mg of product. Material still not quite pure enough by LC (96%). A second crop of 12 mg was collected which was 95% pure. These two crops were combined and dissolved in EtOAc-DCM and the DCM removed by evaporation. The solution was allowed to stand at RT to crystallize the product. HPLC showed >97% purity. The product was placed under high vacuum at 60° C. overnight to drive off EtOAc. Final yield of desired product was 75 mg (18% yield).

Synthesis of Compound 3348

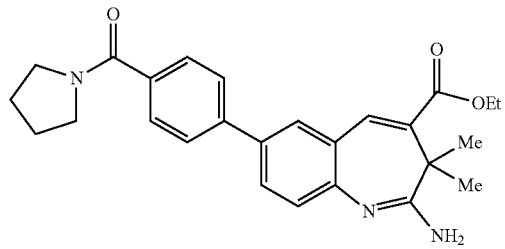 [SMILES: CCOC(=O)C1=Cc2cc(-c3ccc(C(=O)N4CCCC4)cc3)ccc2N=C(N)C1(C)C]

Ethyl 2-amino-3,3-dimethyl-7-[4-(pyrrolidin-1-ylcarbonyl)phenyl]-3H-1-benzazepine-4-carboxylate Ethyl 2-amino-7-bromo-3,3-dimethyl-3H-1-benzazepine-4-carboxylate (0.326 g, 0.967 mmol), 4(pyrrolidin-1-ylcarbonyl)phenylboronic acid (0.339 g, 1.55 mmol), toluene (3.6 mL), ethanol (0.362 mL), water (1.41 mL), and cesium carbonate (0.945 g) were combined and degassed with $N_2$. Tetrakis(triphenylphosphine)palladium(0) (0.08 g, 0.07 mmol) was added and degassing continued for 5 min. The mixture was heated to 80° C. for 4 h. LCMS showed no more bromide and a peak with nearly the same retention time as SM. The mixture was cooled, poured into water and extracted with EtOAc. The organic layer was concentrated and the crude chromatographed on silica gel with 1000:50:2 DCM:MeOH:ammonia. 360 mg of product was isolated but was not pure enough. The material was rechromatographed and the cleanest fractions pooled and crystallized from DCM-heptane to give a white solid. This was dried over the weekend at 50° C. under vacuum, after which DCM was essentially gone by NMR. Final yield of desired product was 320 mg (76.7%).

Synthesis of Compound 3260

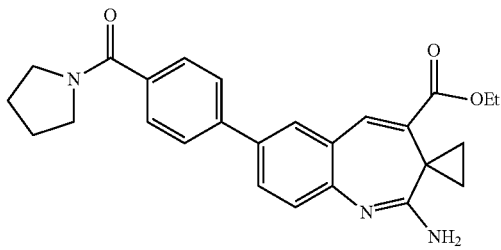 [SMILES: CCOC(=O)C1=Cc2cc(-c3ccc(C(=O)N4CCCC4)cc3)ccc2N=C(N)C12CC2]

Ethyl 2-amino-7-[4-(pyrrolidin-1-ylcarbonyl)phenyl]spiro[1-benzazepine-3,1'-cyclopropane]-4-carboxylate Ethyl 2-amino-7-bromospiro[1-benzazepine-3,1'-cyclopropane]-4-carboxylate (0.130 g, 0.388 mmol), [4-(pyrrolidin-1-ylcarbonyl)phenyl]boronic acid (0.127 g, 0.582 mmol), toluene (5 mL), water (0.699 mL), ethanol (0.70 mL), and cesium carbonate (0.190 g, 0.582 mmol) were combined and degassed by bubbling $N_2$ through the mixture for 10 min. Tetrakis(triphenylphosphine)palladium(0) (0.018 g, 0.016 mmol) was added and degassing continued for a couple of min. The mixture was then heated to 80° C. overnight. LCMS shows the presence of product and the disappearance of SM. The mixture was poured into water and extracted with EtOAc. The organic was washed twice with a little water, dried over $MgSO_4$, filtered, and concentrated to a viscous oil. The product was chromatographed on silica with 1000:25:2.5 DCM:MeOH:ammonia. The crude was then filtered through a 0.45µ filter and the product triturated with MeOH. Filtration gave a pale yellow solid, with 100% purity by HPLC. Final yield of desired product was 59 mg (35%).

Synthesis of Compound 2931

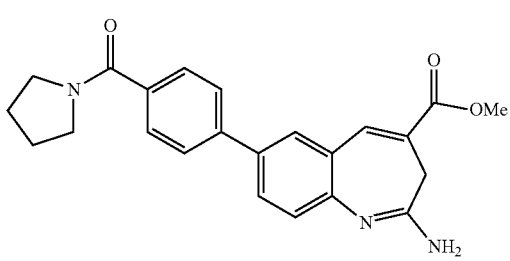 [SMILES: COC(=O)C1=Cc2cc(-c3ccc(C(=O)N4CCCC4)cc3)ccc2N=C(N)C1]

Methyl 2-amino-7-[4-(pyrrolidin-1-ylcarbonyl)phenyl]-3H-1-benzazepine-4-carboxylate Ethyl 2-amino-7-[4-(pyrrolidin-1-ylcarbonyl)phenyl]-3H-1-benzazepine-4-carboxylate (0.200 g, 0.496 mmol) was dissolved in MeOH (10.0 mL) and triethylamine (0.3 mL, 2 mmol) and heated to 80° C. overnight. LCMS showed complete conversion. The MeOH was evaporated to give a crystalline product. Product was triturated with MeOH and vacuum dried at 70° C. overnight. Final yield of desired product was 148 mg (76.7%).

Synthesis of Compound 2984

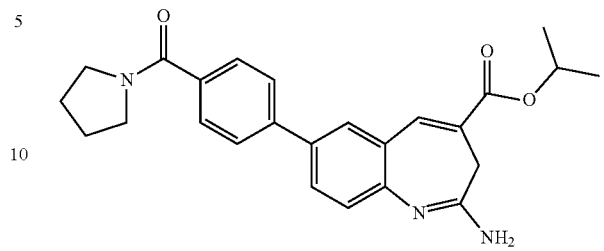

Isopropyl 2-amino-7-[4-(pyrrolidin-1-ylcarbonyl)phenyl]-3H-1-benzazepine-4-carboxylate Isopropyl 2-[bis(tert-butoxycarbonyl)amino]-7-[4-(pyrrolidin-1-ylcarbonyl)phenyl]-3H-1-benzazepine-4-carboxylate (420 mg, 0.41 mmol) was dissolved in DCM (8.0 mL), treated with trifluoroacetic acid (1.0 mL, 14 mmol), and stirred at room temperature overnight. The starting material was fully deprotected. The mixture contained the desired product in about 70% purity by LC. The crude was isolated by direct concentration and overnight high vacuum evaporation of residual TFA. The crude was then purified on a silica gel column eluting with (3-10%) $NH_4OH$ in methanol with DCM. From the initial purification a 150 mg sample was isolated with 93% purity. This material failed to improve upon crystallization from ethyl acetate. It was then repurified with 100% ethyl acetate on a silica gel column and fractions were assayed by HPLC rather than TLC. This allowed combination of only the pure fractions. Final yield of high purity desired product was 38 mg (22%, purity 100%).

Synthesis of Compound 3009

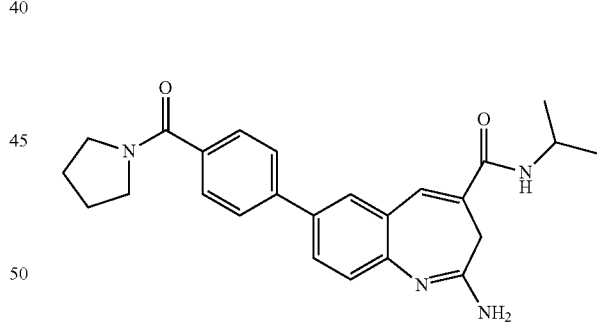

2-Amino-N-isopropyl-7-[4-(pyrrolidin-1-ylcarbonyl)phenyl]-3H-1-benzazepine-4-carboxamide Di-tert-butyl {4-(isopropylcarbamoyl)-7-[4-(pyrrolidin-1-ylcarbonyl)phenyl]-3H-1-benzazepin-2-yl}imidodicarbonate (390 mg, 0.63 mmol) was dissolved in DCM (4 mL), treated with trifluoroacetic acid (0.8 mL, 10 mmol), and stirred at room temperature overnight. Starting material was consumed and the desired product had formed very cleanly (95% by LC). The crude was isolated by concentration to a residue. The residue was dissolved in DCM/MeOH/$NH_4OH$ and washed with water. The product isolated was then triturated with DCM to give a clean white solid (140 mg) with good spectral data except that it appeared to be the TFA salt by NMR. The sample was then taken up in DCM with 10% methanol and stirred with aq. NaHCO$_3$ (2× volume of organic) for 10 minutes. This neutralization was repeated 3 additional times. The combined aqueous was back extracted twice with DCM and the combined organic was dried over anhy. Na$_2$SO$_4$, filtered, and concentrated to an off white powder. Spectral data on this material supported it being the free base and highly pure (100%). Final yield of desired product was 60 mg (20%).

Synthesis of Compound 2986

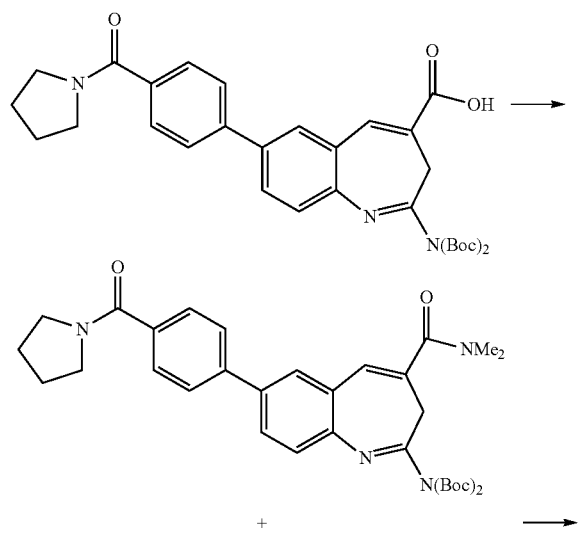

2-Amino-N,N-dimethyl-7-[4-(pyrrolidin-1-ylcarbonyl)phenyl]-3H-1-benzazepine-4-carboxamide Step 1.

2-[Bis(tert-butoxycarbonyl)amino]-7-[4-(pyrrolidin-1-yl-carbonyl)phenyl]-3H-1-benzazepine-4-carboxylic acid (230 mg, 0.40 mmol) was dissolved in DCM (17 mL) and treated with N-(3-dimethylaminopropyl)-N'-ethylcarbodiimide hydrochloride (191 mg, 0.999 mmol), 1-hydroxybenzotriazole (64.8 mg, 0.479 mmol), N,N-diisopropylethylamine (278 uL, 1.60 mmol), and 4-dimethylaminopyridine (12.2 mg, 0.100 mmol). After 30 minutes at room temperature, 3 M dimethylamine in ethanol (146 uL, 0.440 mmol) was added and the mixture stirred at room temperature overnight. The starting material was consumed and a mixture of di- and mono-Boc amidated products was present (about 70% total of crude in a 1.5:1 ratio). The product mixture (230 mg) was isolated by washing with 1N HCl, water, sat. NaHCO$_3$, and drying over anhy. Na$_2$SO$_4$, and used directly in the next step.

Step 2.

The mixture of di- and mono-BOC amidated intermediates from the previous step (230 mg, c. 0.27 mmol) was dissolved in DCM (8.0 mL), treated with trifluoroacetic acid (1.0 mL, 14 mmol), and stirred at room temperature overnight, after which the deprotection was complete. Crude product was isolated by direct concentration of the reaction and then further TFA removal under high vacuum. The crude was purified by column chromatography, eluting with 5-10% methanol containing NH$_4$OH in DCM. The center cut of pure fractions were combined and evaporated. After overnight at 80° C. under high vacuum, material still contained nearly 9 wt % DCM. The mixed fractions (150 mg) were repurified by analogous column; after overnight under high vacuum at 80° C. material still contained residual solvents (EtOAc, MeOH, DCM) at nearly 7 wt %. Both materials were combined and dissolved (MeOH and DCM) and the solution was partially concentrated to produce a slurry. The resultant solids were collected and dried under high vacuum, first overnight at 60° C., then overnight at 75° C., and finally overnight at 95° C. The residual solvent content was reduced to 2.8 wt %, and chemical purity by HPLC was 100 area %. Final yield of desired product was 87 mg (78%).

Synthesis of Compound 2987

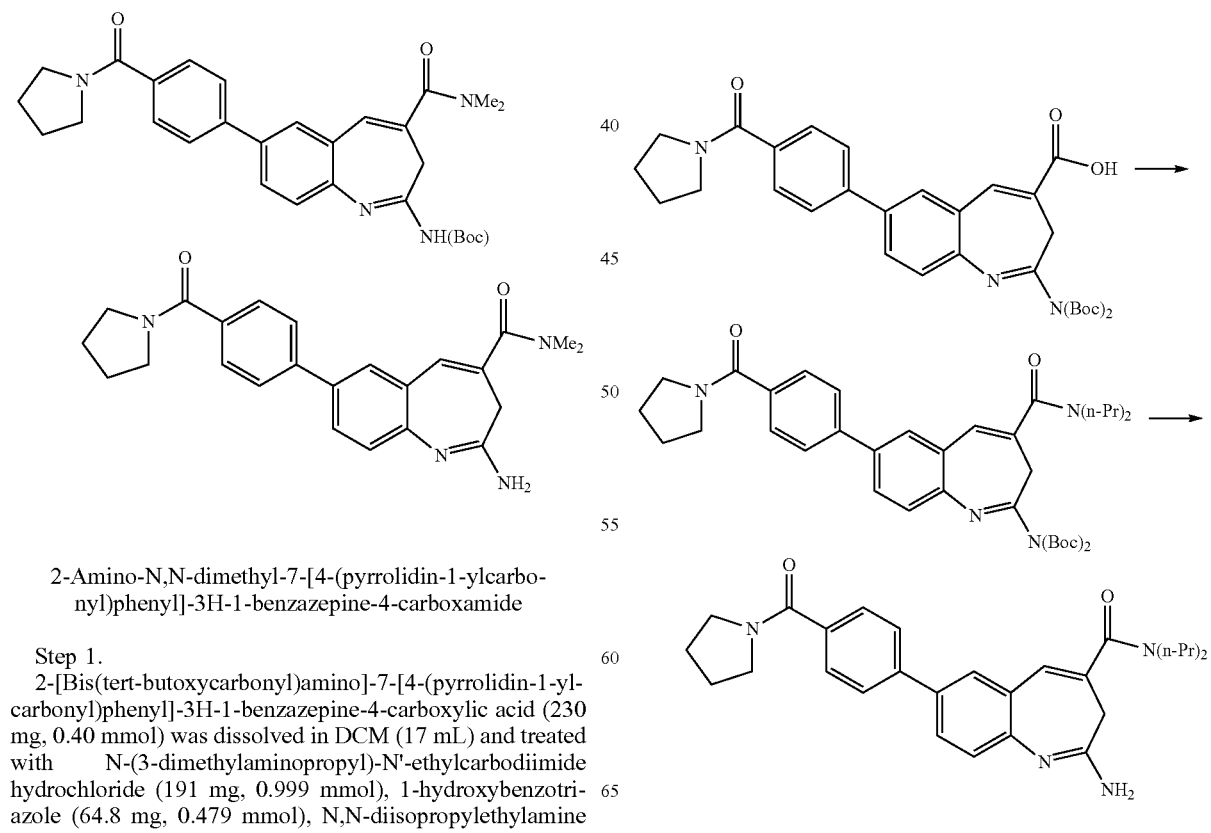

2-Amino-N,N-dipropyl-7-[4-(pyrrolidin-1-ylcarbonyl)phenyl]-3H-1-benzazepine-4-carboxamide Step 1.

2-[Bis(tert-butoxycarbonyl)amino]-7-[4-(pyrrolidin-1-ylcarbonyl)phenyl]-3H-1-benzazepine-4-carboxylic acid (330 mg, 0.57 mmol) was dissolved in DCM (25 mL) and treated with N(3-dimethylaminopropyl)-N'-ethylcarbodiimide hydrochloride (275 mg, 1.43 mmol), 1-hydroxybenzotriazole (93.0 mg, 0.688 mmol), N,N-diisopropylethylamine (399 uL, 2.29 mmol) and 4-dimethylaminopyridine (17.5 mg, 0.143 mmol). After 30 minutes at room temperature, dipropylamine (94.3 uL, 0.688 mmol) was added and the mixture stirred at room temperature overnight. The reaction was worked up by washing with 1N HCl, water, saturated aq. NaHCO₃ and the organic layer dried over anhy. Na₂SO₄. The crude product obtained after evaporation (di-tert-butyl {4-(dipropylcarbamoyl)-7-[4-(pyrrolidin-1-ylcarbonyl)phenyl]-3H-1-benzazepin-2-yl}imidodicarbonate; 410 mg; yield=81%; purity=75%) was used directly in the next step.

Step 2.

Di-tert-butyl {4-(dipropylcarbamoyl)-7-[4-(pyrrolidin-1-ylcarbonyl)phenyl]-3H-1-benzazepin-2-yl}imidodicarbonate (410 mg, 0.47 mmol) from the previous step was dissolved in DCM (8 mL) and treated with TFA (1 mL, 10 mmol). The solution was stirred overnight at room temperature, after which the reaction was complete, with LCMS showing about 75 area % of the desired product. The crude was combined with the crude from a smaller run of Step 1 (c. 100 mg scale) and purified on a silica gel column eluting with MeOH/NH₄OH/DCM to isolated the desired product (188 mg, purity 88 area % by HPLC). This was crystallized from EtOAc to improve the purity to 93-94 area % (170 mg). A second crystallization failed to improve the purity further, so the material was purified on a second silica gel column, collecting only the center fractions. After evaporation and heating at 95° C. under high vacuum overnight, the residual EtOAc was reduced to 3 wt %, and chemical purity was 100%. Final yield of desired product was 70 mg (30%).

Synthesis of Compound 3058

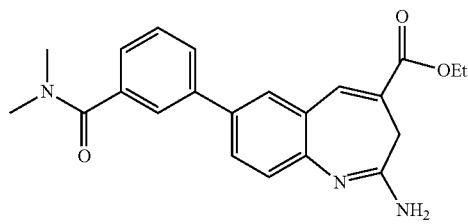 [SMILES: CCOC(=O)C1=Cc2cc(-c3cccc(C(=O)N(C)C)c3)ccc2N=C(N)C1]

Ethyl 2-amino-7-[3-(dimethylcarbamoyl)phenyl]-3H-1-benzazepine-4-carboxylate

Ethyl 2-amino-7-bromo-3H-1-benzazepine-4-carboxylate (543 mg, 1.76 mmol), [3-(dimethylcarbamoyl)phenyl]boronic acid (364 mg, 1.88 mmol), and cesium carbonate (862 mg, 2.64 mmol) were combined in toluene (10 mL), EtOH (1 mL), and water (3 mL). This slurry was degassed with a nitrogen purge, treated with tetrakis(triphenylphosphine)palladium(0) (44 mg, 0.038 mmol), and after a final degassing, heated in an oil bath held at 75-80° C. for 10 hours, then cooled overnight. The starting material was consumed and the desired product was the major component by HPLC at 80 area % (254 nm). The crude was isolated by diluting with water and extracting with EtOAc. The organic was washed with water, dried over Na₂SO₄, filtered, and concentrated to low volume to give a slurry. The slurry was filtered and rinsed with EtOAc. The product cake was dried under nitrogen press and then high vacuum to give 392 mg (59%) of desired product with high purity.

Synthesis of Compound 2937

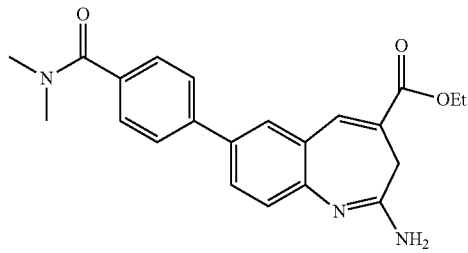 [SMILES: CCOC(=O)C1=Cc2cc(-c3ccc(C(=O)N(C)C)cc3)ccc2N=C(N)C1]

Ethyl 2-amino-7-[4-(dimethylcarbamoyl)phenyl]-3H-1-benzazepine-4-carboxylate

Ethyl 2-amino-7-bromo-3H-1-benzazepine-4-carboxylate (180 mg, 0.58 mmol) and [4-(dimethylcarbamoyl)phenyl]boronic acid (168 mg, 0.873 mmol) were slurried in toluene (4 mL) and EtOH (0.4 mL) and degassed with nitrogen. To this was added tetrakis(triphenylphosphine)palladium(0) (13.4 mg, 0.0116 mmol) and degassing continued. After about 5 minutes of further degassing a solution of cesium carbonate, prepared by dissolving cesium carbonate (284 mg, 0.873 mmol) in water (1 mL) was added. A final degassing was followed by heating in an oil bath held at 80° C. overnight. The crude product was isolated and purified by column chromatography, eluting with MeOH containing NH₄OH in DCM (2-6%) to isolate 77 mg (34%) of desired product with 98% purity.

Synthesis of Compound 3096

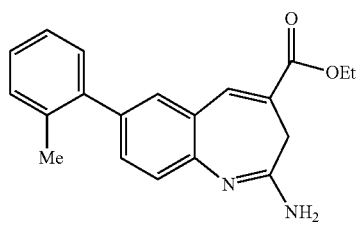 [SMILES: CCOC(=O)C1=Cc2cc(-c3ccccc3C)ccc2N=C(N)C1]

Ethyl 2-amino-7-(2-methylphenyl)-3H-1-benzazepine-4-carboxylate

Ethyl 2-amino-7-bromo-3H-1-benzazepine-4-carboxylate (255 mg, 0.825 mmol), 2-methylphenylboronic acid (118 mg, 0.866 mmol), and cesium carbonate (403 mg, 1.24 mmol) were slurried in toluene (7 mL), EtOH (0.7 mL), and water (0.7 mL), and degassed with nitrogen. The mixture was treated with tetrakis(triphenylphosphine)palladium(0)

(19.1 mg, 0.0165 mmol) and then heated in an oil bath held at 75° C. overnight. The reaction was complete in the morning. The crude was isolated using EtOAc extractions and aq. NaHCO₃ washes. The crude was adsorbed onto silica gel and purified on a silica gel column eluting with 10% MeOH in DCM to recover the desired product in a yield of 76 mg (29%).

Synthesis of Compound 3141

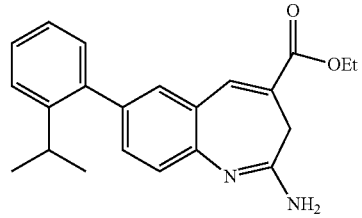 [SMILES: CCOC(=O)C1=Cc2cc(-c3ccccc3C(C)C)ccc2N=C(N)C1]

Ethyl 2-amino-7-(2-isopropylphenyl)-3H-1-benzazepine-4-carboxylate

Ethyl-2-amino-7-bromo-3H-1-benzazepine-4-carboxylate (630 mg, 2.0 mmol), (2-isopropylphenyl)boronic acid (435 mg, 2.65 mmol), and cesium carbonate (996 mg, 3.06 mmol) were slurried in EtOH (1.3 mL), toluene (10 mL), and water (5.0 mL) and degassed by passing N₂ through the mixture for 20 min. Tetrakis(triphenylphosphine)palladium (0) (0.177 g, 0.153 mmol) was added and degassing continued for 5 min. The mixture was heated to 80° C. overnight and then cooled. The crude product was isolated using EtOAc and purified by chromatography on silica gel with DCM-MeOH-ammonia (1500:75:0.75). This gave a foam upon concentration. After holding under vacuum overnight it still contained EtOAc. The material was taken up in DCM and concentrated to remove EtOAc. Final yield of desired product was 390 mg (55%).

Synthesis of Compound 3272

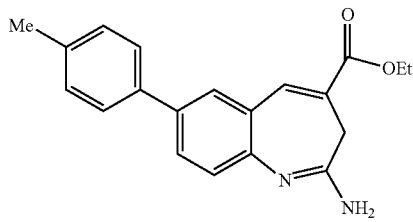 [SMILES: CCOC(=O)C1=Cc2cc(-c3ccc(C)cc3)ccc2N=C(N)C1]

Ethyl 2-amino-7-(4-methylphenyl)-3H-1-benzazepine-4-carboxylate

Ethyl 2-amino-7-bromo-3H-1-benzazepine-4-carboxylate (0.400 g, 1.29 mmol), 4-tolylboronic acid (0.264 g, 1.94 mmol), ethanol (0.665 mL), water (2.33 mL), and cesium carbonate (0.632 g, 1.94 mmol) were combined and degassed with N₂. Tetrakis(triphenylphosphine)palladium (0) (0.0448 g, 0.0388 mmol) was then added and the mixture degassed for another few minutes. The mixture was heated to 80° C. overnight. The solution was cooled, poured into water, and the product extracted with EtOAc. The organic layer was washed twice with water and then concentrated. The crude product was triturated with ether but this failed to remove a non-polar impurity. The product was chromatographed on silica with 1000:50:2 DCM:MeOH:ammonia to give a yellow solid. This was triturated with MeOH, collected by filtration, and vacuum dried at 50° C. Final yield of desired product was 215 mg (52% yield). MS (ESI+) consistent for $C_{20}H_{20}N_2O_2$ (M+H)⁺: m/z 321.2.

Synthesis of Compound 3264

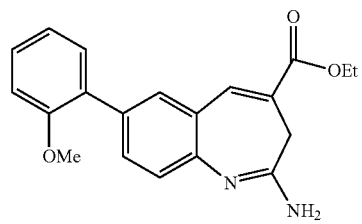 [SMILES: CCOC(=O)C1=Cc2cc(-c3ccccc3OC)ccc2N=C(N)C1]

Ethyl 2-amino-7-(2-methoxyphenyl)-3H-1-benzazepine-4-carboxylate

Ethyl-2-amino-7-bromo-3H-1-benzazepine-4-carboxylate (0.400 g, 1.29 mmol), 2-methoxyphenylboronic acid (0.295 g, 1.94 mmol), ethanol (0.665 mL), water (2.33 mL), and cesium carbonate (0.632 g, 1.94 mmol) were combined and degassed with N₂. Tetrakis(triphenylphosphine)palladium(0) (0.0448 g, 0.0388 mmol) was then added and the mixture degassed for another few minutes. The mixture was heated to 80° C. overnight. HPLC showed clean conversion. The product was extracted into EtOAc, concentrated, and chromatographed on silica with 1000:50:2 DCM:MeOH: ammonia. The isolated material was crystallized from MeOH, collected by filtration, and dried under vacuum at 50° C. overnight. Final yield of desired product was 218 mg (50%). MS (ESI+) consistent for $C_{20}H_{20}N_2O_3$ (M+H)⁺: m/z 337.3.

Synthesis of Compound 3267

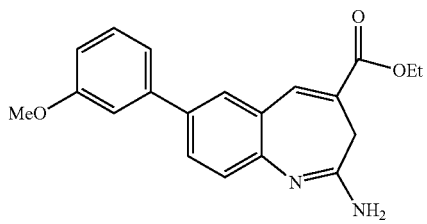 [SMILES: CCOC(=O)C1=Cc2cc(-c3cccc(OC)c3)ccc2N=C(N)C1]

Ethyl 2-amino-7-(3-methoxyphenyl)-3H-1-benzazepine-4-carboxylate

Ethyl 2-amino-7-bromo-3H-1-benzazepine-4-carboxylate (0.400 g, 1.29 mmol), 3-methoxyphenylboronic acid (0.295 g, 1.94 mmol), toluene (8.27 mL), ethanol (0.665 mL), water (2.33 mL) and cesium carbonate (0.632 g, 1.94 mmol) were combined and degassed with N₂ bubbling. Tetrakis(triphenylphosphine)palladium(0) (0.0448 g, 0.0388 mmol) was then added and degassing continued for a minute. The slurry was then heated to 80° C. overnight. Solids came out of the solution when cooled. These were removed by filtration. HPLC showed a less polar impurity. Trituration with MeOH failed to remove this as did crystallization from MeOH-DCM. Product was chromatographed on silica with 1000:50:2 DCM:MeOH:ammonia. This separated the nonpolar impurity according to TLC. White solids were obtained from MeOH. Filtration and drying afforded the product, which was vacuum dried at 50° C. for 3 hr. Final yield of desired product was 199 mg (46%). MS (ESI+) consistent for $C_{20}H_{20}N_2O_3$ (M+H)$^+$: m/z 337.3.

Synthesis of Compound 3098

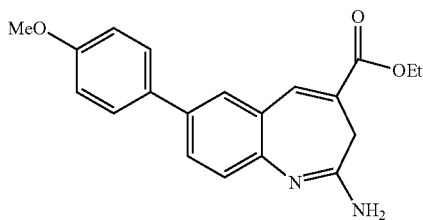 [SMILES: CCOC(=O)C1=Cc2cc(-c3ccc(OC)cc3)ccc2N=C(N)C1]

Ethyl 2-amino-7-(4-methoxyphenyl)-3H-1-benzazepine-4-carboxylate

Ethyl 2-amino-7-bromo-3H-1-benzazepine-4-carboxylate (255 mg, 0.825 mmol), 4-methoxyphenyl boronic acid (132 mg, 0.866 mmol), and cesium carbonate (403 mg, 1.24 mmol) were combined with toluene (7 mL), ethanol (0.7 mL) and water (0.7 mL). The mixture was degassed, treated with tetrakis(triphenylphosphine)palladium(0) (19.1 mg, 0.0165 mmol) and heated at 75° C. overnight. The desired product was the major product. Crude product was isolated using ethyl acetate and washing with aq. NaHCO$_3$. The product was isolated in very good purity using a silica gel column, but NMR indicated it was the acetate salt. The material was dissolved in DCM and washed 3 times with aq. NaHCO$_3$ to give the product as the free base. Final yield of desired product was 50 mg (20%). MS (ESI+) consistent for $C_{20}H_{20}N_2O_3$ (M+H)$^+$: m/z 337.1.

Synthesis of 3127

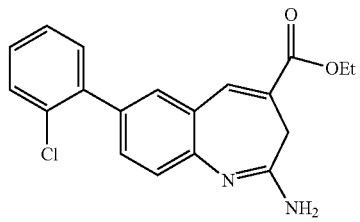

Ethyl 2-amino-7-(2-chlorophenyl)-3H-1-benzazepine-4-carboxylate

2-Chlorophenylboronic acid (211 mg, 1.35 mmol), ethyl 2-amino-7-bromo-3H-1-benzazepine-4-carboxylate (319 mg, 1.03 mmol), toluene (6 mL), ethanol (0.6 mL), cesium carbonate (553 mg, 1.70 mmol), and water (1 mL) were combined and the slurry was degassed with nitrogen. Tetrakis(triphenylphosphine)palladium(0) (60 mg, 0.052 mmol) was added, the mixture degassed again, then heated in an oil bath at 80° C. Crude product was isolated after diluting with ethyl acetate and washing with aq. NaHCO$_3$. Purification by crystallization did not work; material was a foam and contained an impurity. Column purification was successful, using first MeOH in DCM (5%), then switching to MeOH containing 10% aq. NH$_4$OH. Final yield of desired product was 148 mg (42%). MS (ESI+) consistent for $C_{19}H_{17}ClN_2O_2$ (M+H)$^+$: m/z 341.0.

Synthesis of Compound 3155

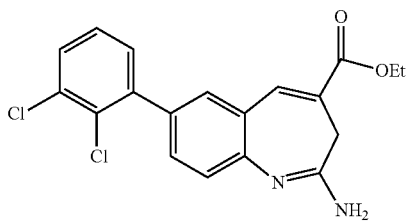 [SMILES: CCOC(=O)C1=Cc2cc(-c3cccc(Cl)c3Cl)ccc2N=C(N)C1]

Ethyl 2-amino-7-(2,3-dichlorophenyl)-3H-1-benzazepine-4-carboxylate (2,3-Dichlorophenyl)boronic acid (764 mg, 4.00 mmol), ethyl 2-amino-7-bromo-3H-1-benzazepine-4-carboxylate (399 mg, 1.29 mmol), toluene (15.0 mL), ethanol (1.5 mL), cesium carbonate (1.74 g, 5.34 mmol), and water (3.0 mL) were combined and the slurry was degassed with nitrogen. Tetrakis(triphenylphosphine)palladium(0) (147 mg, 0.127 mmol) was added, the mixture degassed again, then heated in an oil bath at 72° C. overnight. In the morning ethyl 2-amino-7-bromo-3H-1-benzazepine-4-carboxylate was consumed and the reaction was complete. The crude product was isolated using ethyl acetate and aq. NaHCO$_3$ washes. The crude product was dissolved in ethyl acetate and cooled to give a crop of crystals with sufficient purity. Final yield of desired product was 180 mg (37%). MS (ESI+) consistent for $C_{19}H_{16}Cl_2N_2O_2$ (M+H)$^+$: m/z 375.0.

Synthesis of Compound 3294

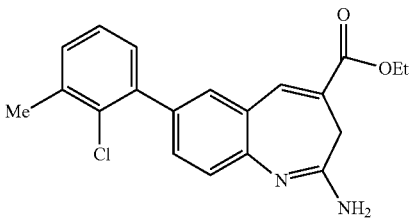 [SMILES: CCOC(=O)C1=Cc2cc(-c3cccc(C)c3Cl)ccc2N=C(N)C1]

Ethyl 2-amino-7-(2-chloro-3-methylphenyl)-3H-1-benzazepine-4-carboxylate (2-Chloro-3-methylphenyl)-4,4,5,5-tetramethyl-1,3,2-dioxaborolane (0.551 g, 2.18 mmol), ethyl 2-amino-7-bromo-3H-1-benzazepine-4-carboxylate (0.450 g, 1.46 mmol), toluene (10.0 mL), water (2.5 mL), ethanol (0.70 mL) and cesium carbonate (1.42 g, 4.37 mmol) were combined and degassed with a $N_2$ purge. Tetrakis(triphenylphosphine)palladium(0) (0.0841 g, 0.0728 mmol) was then added and the mixture heated to 80° C. overnight. The mixture was cooled, poured into water, and extracted with EtOAc. The crude product was chromatographed on silica with 1000:50:2 DCM:MeOH:ammonia. The isolated yelllow solid was triturated in MeOH and filtered. The product was recrystallized by dissolving in MeOH-DCM and then blowing off the DCM to give a heavy solid. This was filtered and dried at 60° C. for 2 hr. Final yield of desired product was 284 mg (55%). MS (ESI+) consistent for $C_{20}H_{19}ClN_2O_2$ $(M+H)^+$: m/z 355.2.

Synthesis of Compound 3386

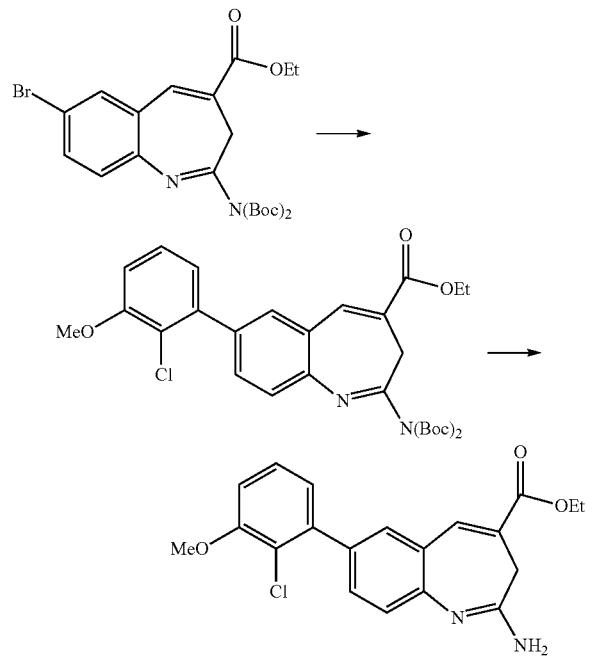

Ethyl 2-amino-7-(2-chloro-3-methoxyphenyl)-3H-1-benzazepine-4-carboxylate

Step 1.

Ethyl 2-[bis(tert-butoxycarbonyl)amino]-7-bromo-3H-1-benzazepine-4-carboxylate (354 mg, 0.695 mmol), (2-chloro-3-methoxyphenyl)boronic acid (154 mg, 0.826 mmol), and cesium carbonate (359 mg, 1.10 mmol) were dissolved in toluene (4 mL), ethanol (0.4 mL), and water (1 mL). The mixture was degassed, treated with tetrakis(triphenylphosphine)palladium(0) (36 mg, 0.031 mmol), and heated in a sand bath held at 85° C. for 2 hours, after which the reaction was nearly complete. The mixture was treated with additional (2-chloro-3-methoxyphenyl)boronic acid and tetrakis(triphenylphosphine)palladium(0) and degassed. The mixture was heated for another hour and the reaction was then complete. The crude product was isolated using ethyl acetate and aq. $NaCHO_3$, and purified on silica gel eluting with 20-40% EtOAc in hexanes. The intermediate product obtained after evaporation (ethyl 2-[bis(tert-butoxycarbonyl)amino]-7-(2-chloro-3-methoxyphenyl)-3H-1-benzazepine-4-carboxylate; 360 mg; yield=82%; purity=91%) was used directly in the next step.

Step 2.

Ethyl 2-[bis(tert-butoxylcarbonyl)amino]-7-(2-chloro-3-methoxyphenyl)-3H-1-benzazepine-4-carboxylate (360 mg, 0.57 mmol) from the previous step was dissolved in DCM (4.0 mL) and treated with TFA (2.0 mL, 26 mmol). After 1 hour at room temperature the reaction was complete. The volatiles were removed and the oily residue treated with 5 mL ether to give a slurry. The slurry was filtered, transferring with 2.5 mL ether, and the cake rinsed with 2.5 mL ether. After drying the product (as the TFA salt) was converted to the free base using aq. $NaHCO_3$/DCM. Final yield of desired product was 120 mg (56% for this step). MS (ESI+) consistent for $C_{20}H_{19}ClN_2O_3$ $(M+H)^+$: m/z 371.1.

Synthesis of Compound 3126

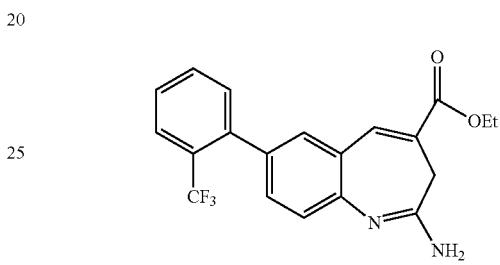

Ethyl 2-amino-7-[2-(trifluoromethyl)phenyl]-3H-1-benzazepine-4-carboxylate

2-Trifluoromethylphenylboronic acid (233 mg, 1.23 mmol), ethyl-2-amino-7-bromo-3H-1-benzazepine-4-carboxylate (269 mg, 0.870 mmol), toluene (5 mL), ethanol (0.5 mL), cesium carbonate (479 mg, 1.47 mmol), and water (1 mL) were combined and the slurry was degassed with nitrogen. Tetrakis(triphenylphosphine)palladium(0) (50 mg, 0.044 mmol) was added, the mixture degassed again, and heated in an oil bath held at 80° C. overnight. The yellow slurry became a yellow solution. Assays indicate complete, reasonably clean conversion to the desired product. The reaction was filtered through a pad of magnesol, rinsing with EtOAc. The organic layer was washed with water and sat. aq. NaCl solution and dried over anhydrous $Na_2SO_4$. After concentration a crude yellow solid was isolated. The solid was dissolved in nearly refluxing EtOAc, then the solution cooled, first to room temperature, then at −10 to 0° C. The filtered slurry was washed with cold EtOAc and dried to isolate 91 mg of the desired product (yield=28%; purity=100%). A second crop of 100 mg (yield=30%; purity=98%) was isolated from the filtrate after concentration and trituration with MTBE. Combined yield of two crops of desired material was 191 mg (58%). MS (ESI+) consistent for $C_{20}H_{17}F_3N_2O_2$ $(M+H)^+$: m/z 375.0.

Synthesis of Compound 3059

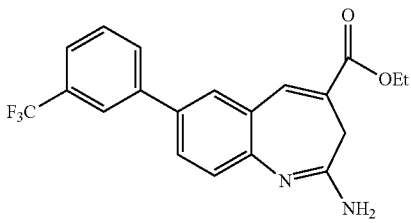 [SMILES: CCOC(=O)C1=Cc2cc(-c3cccc(C(F)(F)F)c3)ccc2N=C(N)C1]

Ethyl 2-amino-7-[3-(trifluoromethyl)phenyl]-3H-1-benzazepine-4-carboxylate

3-Trifluoromethylphenylboronic acid (553 mg, 2.91 mmol), ethyl 2-amino-7-bromo-3H-1-benzazepine-4-carboxylate (600 mg, 2 mmol), and cesium carbonate (948 mg, 2.91 mmol) were slurried in toluene (10 mL), ethanol (1 mL), and water (4 mL) and degassed with $N_2$ blown through the solution for 20 min. Tetrakis(triphenylphosphine)palladium(0) (44.8 mg, 0.0388 mmol) was then added and the $N_2$ purge continued for 5 min. The mixture was heated to 80° C. overnight. The solution was cooled and poured into water and extracted twice with EtOAc. The combined organic phases were washed with water, dried over $MgSO_4$, and then passed through a plug of magnesol and concentrated to a solid. The product was recrystallized three times from EtOAc and then once from MeOH. Final yield of desired product was 213 mg (30%). MS (ESI+) consistent for $C_{20}H_{17}F_3N_2O_2$ $(M+H)^+$: m/z 375.0.

Synthesis of Compound 3101

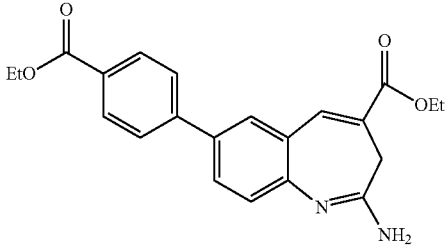 [SMILES: CCOC(=O)C1=Cc2cc(-c3ccc(C(=O)OCC)cc3)ccc2N=C(N)C1]

Ethyl 2-amino-7-[4-(ethoxycarbonyl)phenyl]-3H-1-benzazepine-4-carboxylate

Ethyl 2-amino-7-bromo-3H-1-benzazepine-4-carboxylate (255 mg, 0.825 mmol), 4-(ethoxycarbonyl)phenylboronic acid (168 mg, 0.866 mmol), cesium carbonate (403 mg, 1.24 mmol), toluene (7 mL), and ethanol (0.7 mL) were combined, degassed, and treated with tetrakis(triphenylphosphine)palladium(0) (19.1 mg, 0.0165 mmol). The slurry was heated in an oil bath held at 75° C. overnight. In the morning essentially no reaction had occurred. The mixture was still a slurry so it was obvious that solubility was a limitation. A small amount of water was added and the mixture was again heated. After 4-5 hours the mixture was a solution and assay by HPLC indicated good conversion to the desired product. Crude product was isolated after diluting with EtOAc and washing with aq. $NaHCO_3$ and drying over $Na_2SO_4$. Product was purified on a silica gel column after adsorbing onto silica gel. Elution was afforded with 5-10% MeOH in DCM. The column purified material contained about 15% of an early peak which had the mass of the starting boronic acid. The product was taken up in DCM, treated with aq. $NaHCO_3$, and stirred overnight, but the early peak was only reduced to about 5%. At this point crystallization from EtOAc removed the impurity cleanly. Final yield of desired product was 150 mg (48%). MS (ESI+) consistent for $C_{22}H_{22}N_2O_4$ $(M+H)^+$: m/z 379.1.

Synthesis of Compound 3055

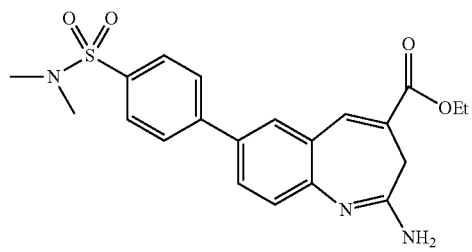 [SMILES: CCOC(=O)C1=Cc2cc(-c3ccc(S(=O)(=O)N(C)C)cc3)ccc2N=C(N)C1]

Ethyl 2-amino-7-{4-[(dimethylamino)sulfonyl]phenyl}-3H-1-benzazepine-4-carboxylate Ethyl 2-amino-7-bromo-3H-1-benzazepine-4-carboxylate (644 mg, 2.08 mmol), 4-[(dimethylamino)sulfonyl]phenylboronic acid (716 mg, 3.12 mmol), and cesium carbonate (1020 mg, 3.12 mmol) were slurried in ethanol (1.1 mL), toluene (10 mL), and water (4 mL) and degassed by passing $N_2$ through the mixture for 20 min. Tetrakis(triphenylphosphine)palladium(0) (48.1 mg, 0.0417 mmol) was then added and degassing continued for 5 min. The mixture was heated to 75° C. overnight and then cooled. The solids which precipitated from the mixture were filtered and washed with water and EtOAc. The crude solids were taken up in EtOAc and heated to try and recrystallize the product but were not soluble so the mixture was concentrated and taken up in EtOH and heated. Still not soluble so triturated in hot EtOH, cooled and the slurry filtered and washed with MTBE to remove EtOH. After vacuum drying the final yield of desired product was 540 mg (63%). MS (ESI+) consistent for $C_{21}H_{23}N_3O_4S$ $(M+H)^+$: m/z 414.0, and MS (ESI-) consistent for $C_{21}H_{23}N_3O_4S$ $(M-H)^-$: m/z 412.1.

Synthesis of Compound 3119

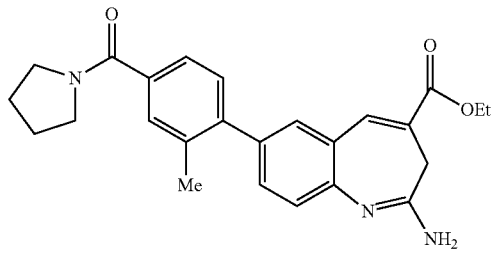 [SMILES: CCOC(=O)C1=Cc2cc(-c3ccc(C(=O)N4CCCC4)cc3C)ccc2N=C(N)C1]

Ethyl 2-amino-7-[2-methyl-4-(pyrrolidin-1-ylcarbonyl)phenyl]-3H-1-benzazepine-4-carboxylate 1-[3-Methyl-4-(4,4,5,5-tetramethyl-1,3,2-dioxaborolan-2-yl)benzoyl]pyrrolidine (720 mg, 2.3 mmol), ethyl 2-amino-7-bromo-3H-1-benzazepine-4-carboxylate (538 mg, 1.74 mmol), toluene (20 mL), ethanol (2 mL), cesium carbonate (999 mg, 3.07 mmol), and water (4 mL) were combined and the slurry was degassed with $N_2$. Tetrakis(triphenylphosphine)palladium(0) (110 mg, 0.0956 mmol) was added, the mixture degassed again, and heated in an oil bath held at 80° C. After 3 hours the reaction was a solution. After 4 hours the reaction was assayed and, although a small amount of the bromide remained, the boronate reagent was consumed. The reaction was cooled and held overnight until workup. The crude was isolated with a standard aq. $NaHCO_3$/EtOAc workup as a semi-solid with about 85% purity. Attempts to crystallize from EtOAc gave material that was only 94-97% pure and retained EtOAc. The best solvent found for recrystallization was MeOH, although recovery was not great. Final yield of desired product was 110 mg (15%), with 98.3% purity by LC and containing 0.3 wt % MeOH. MS (ESI+) consistent for $C_{25}H_{27}N_3O_3$ (M+H)$^+$: m/z 418.2.

Synthesis of Compound 3190

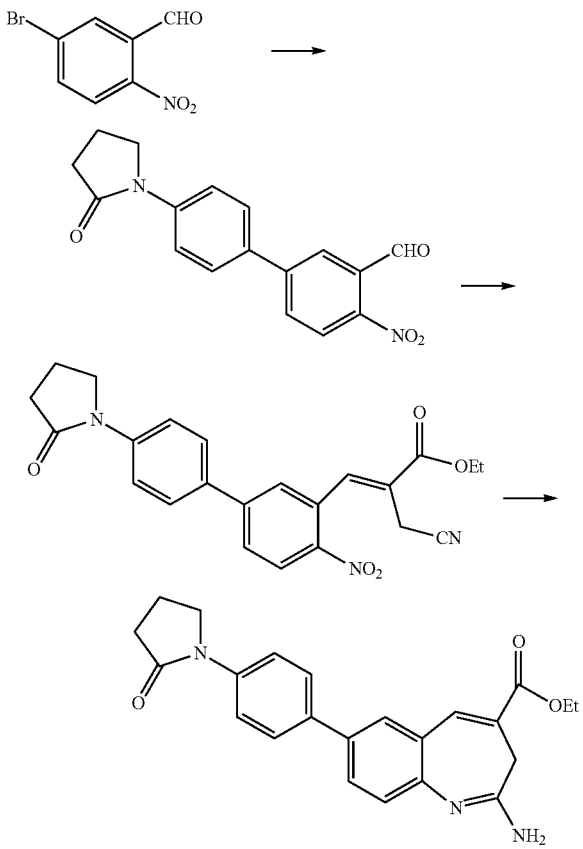

Ethyl 2-amino-7-[4-(2-oxopyrrolidin-1-yl)phenyl]-3H-1-benzazepine-4-carboxylate Step 1.

5-Bromo-2-nitrobenzaldehyde (1.0 g, 4.3 mmol), 1-[4-(4,4,5,5-tetramethyl-1,3,2-dioxaborolan-2-yl)phenyl]pyrrolidin-2-one (1.40 g, 4.87 mmol), cesium carbonate (2.12 g, 6.52 mmol), toluene (9.9 mL), water (3.3 mL), and ethanol (0.99 mL) were combined in a flask and degassed by bubbling $N_2$ through the mixture. Tetrakis(triphenylphosphine)palladium(0) (30 mg, 0.03 mmol) was added and the mixture heated to 75° C. overnight. HPLC showed formation of a new product. The mixture was cooled to RT and poured into water and extracted three times with EtOAc. Concentration of the combined EtOAc layers gave only a trace of an orange solid. The aqueous layer was acidified with HCl and filtered with the aid of DCM to remove some solids. This resulted in the slow leaching of an orange material. Concentration of the DCM extract left an orange solid. By NMR the solid appeared to be product along with some boronate. The crude was crystallized from EtOAc-DCM by evaporation of the DCM, producing a crystalline orange solid. NMR showed this to be desired product, 4-nitro-4'-(2-oxopyrrolidin-1-yl)biphenyl-3-carbaldehyde (1.18 g, 87%).

Step 2.

4-Nitro-4'-(2-oxopyrrolidin-1-yl)biphenyl-3-carbaldehyde (0.800 g, 2.58 mmol) and ethyl 3-cyano-2-(triphenylphosphoranylidene)propanoate (1.10 g, 2.84 mmol) were combined in toluene (15 mL) and heated to 80° C. for 2 hours, after which the orange color had disappeared. The solution was allowed to cool to RT at which point some solids crystallized from the reaction. These were removed by filtration and proved to be 625 mg of desired product by NMR. The mother liquor was chromatographed on silica with 75% EtOAc-heptane to afford an additional 410 mg of product. The combined crops of the desired product, ethyl (2E)-2-(cyanomethyl)-3-[4-nitro-4'-(2-oxopyrrolidin-1-yl)biphenyl-3-yl]acrylate, (1.03 g, 95%) were used directly in the following step.

Step 3.

Ethyl (2E)-2-(cyanomethyl)-3-[4-nitro-4'-(2-oxopyrrolidin-1-yl)biphenyl-3-yl]acrylate (1.04 g, 2.48 mmol) was taken up in ethanol (15 mL) and AcOH (3.0 mL) and treated with iron (0.415 g, 7.44 mmol) and heated to 80° C. The reaction was complete within 2 hr. Ethylenediaminetetraacetic acid, disodium salt dihydrate (2.77 g, 7.44 mmol) and 15 mL of water was added to the cooled reaction mixture, resulting in nearly all of the iron salts going into solution. The solution went from brown to yellow in color. The product was extracted with two portions of EtOAc. The combined organic layers were washed twice with sat. $NaHCO_3$ and once with water. The solution was dried over $MgSO_4$, filtered, and concentrated to an oil. NMR of the orange material showed it was still the uncyclized, aniline form. The crude material was taken up in AcOH and heated to 80° C. to drive the cyclization. At 1 hour a sample showed about 80% conversion. After heating over the weekend the reaction showed clean product by HPLC. The majority of the AcOH was removed under reduced pressure. Attempts to dissolve the product with EtOAc and sat. $NaHCO_3$ failed. The EtOAc was removed and replaced with DCM (~300 mL). After stirring for a few minutes the slurry dissolved and the mixture became clear. The DCM layer was separated, dried over $MgSO_4$, filtered, and concentrated to give a solid. The solid was redissolved in DCM and then partially concentrated to crystallize the product. This was filtered, washed with EtOAc, and dried. NMR showed about 1 wt %

EtOAc. Final yield of desired product was 540 mg (56%). MS (ESI+) consistent for $C_{23}H_{23}N_3O_3$ (M+H)$^+$: m/z 390.1.

Synthesis of Compound 3199

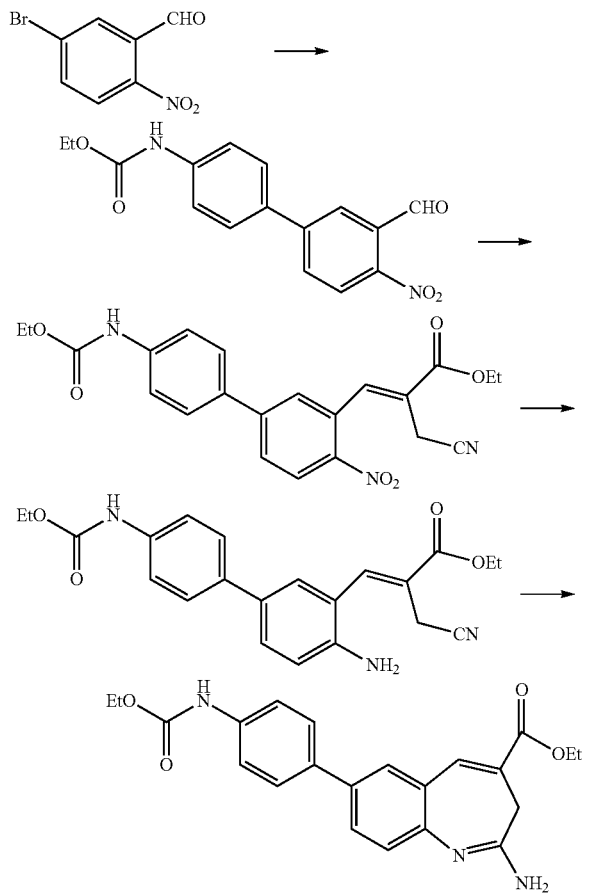

Ethyl 2-amino-7-{4-[(ethoxycarbonyl)amino]phenyl}-3H-1-benzazepine-4-carboxylate Step 1.
5-Bromo-2-nitrobenzaldehyde (0.512 g, 2.22 mmol), ethyl[4-(4,4,5,5-tetramethyl-1,3,2-dioxaborolan-2-yl)phenyl]carbamate (0.780 g, 2.68 mmol), cesium carbonate (1.09 g, 3.34 mmol), toluene (20 mL), ethanol (2 mL), and water (4 mL) were combined and degassed. Tetrakis(triphenylphosphine)palladium(0) (51.0 mg, 0.0441 mmol) was added and the mixture heated in an oil bath at 75° C. for 20 hours. The crude was extracted into EtOAc and washed with aq. NaHCO$_3$, water, and brine, and dried over anhydrous Na$_2$SO$_4$. The crude product, ethyl (3'-formyl-4'-nitrobiphenyl-4-yl)carbamate, was used directly in the next step.

Step 2.
Ethyl (3'-formyl-4'-nitrobiphenyl-4-yl)carbamate (690 mg, 2.2 mmol) and ethyl 3-cyano-2-(triphenylphosphoranylidene)propanoate (1.02 g, 2.63 mmol) were slurried in Toluene (7 mL) and heated at 100° C. After 45 minutes the starting material was consumed. The toluene was removed and the residue held under high vacuum. After a brief period no solids had formed and the sample was prepared for column purification by dissolving in minimal DCM. Before loading the column solids were noted in the flask. Sonication of the DCM solution gave a thick slurry. The slurry was diluted with ether, further sonicated, then the solids collected by filtration. This gave 770 mg of the desired product, ethyl (2E)-2-(cyanomethyl)-3-{4'-[ethoxycarbonyl)amino]-4-nitrobiphenyl-3-yl}acrylate (yield 80%; purity 96%), which was used directly in the next step.

Step 3.
Ethyl (2E)-2-(cyanomethyl)-3-{4'-[(ethoxycarbonyl)amino)-4-nitrobiphenyl-3-yl}acrylate (770 mg, 1.8 mmol) was slurried in ethanol (20 mL) and AcOH (2 mL). This was treated with iron (0.33 g, 5.9 mmol) and heated at 80° C. After 2 hours the starting material was consumed and the desired product was the major product. Some of the cyclized material and a minor amount of triphenylphosphine oxide were present. Product was isolated via DCM extraction after stirring the reaction mixture with an aqueous solution of disodium EDTA. Crude yield of the desired product, ethyl (2E)-3-{4-amino-4'-[(ethoxycarbonyl)amino]biphenyl-3-yl}-2-(cyanomethyl)acrylate, was 690 mg (96%). This material was used without purification in the next step.

Step 4.
Ethyl (2E)-3-{4-amino-4'-[(ethoxycarbonyl)amino]biphenyl-3-yl}-2-(cyanomethyl)acrylate (0.690 g, 1.75 mmol) was dissolved in AcOH (12 mL) and heated at 80° C. for 2 hours, after which the starting material was consumed. The AcOH was removed under vacuum and the solids triturated with MTBE and filtered to recover the desired product as the acetate salt. The salt was dissolved in DCM and then stirred with aq. NaHCO$_3$ for 5 minutes. The phases were separated and the organic layer washed 2 additional times with aq. NaHCO$_3$. After drying over anhydrous Na$_2$SO$_4$ the organic layer was concentrated to a low volume, the resulting slurry collected, and the product cake washed with ether. Final yield of the desired product was 490 mg (71%). MS (ESI+) consistent for $C_{22}H_{23}N_3O_4$ (M+H)$^+$: m/z 394.2.

Synthesis of Compound 3261

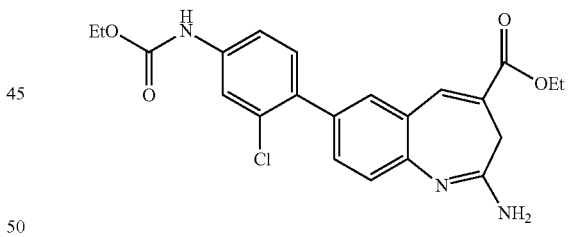

Ethyl 2-amino-7-{2-chloro-4-[(ethoxycarbonyl)amino]phenyl}-3H-1-benzazepine-4-carboxylate Ethyl 2-amino-7-bromo-3H-1-benzazepine-4-carboxylate (282 mg, 0.911 mmol), ethyl[3-chloro-4(4,4,5,5-tetramethyl-1,3,2-dioxaborolan-2-yl)phenyl]carbamate (445 mg, 1.37 mmol), and cesium carbonate (445 mg, 1.37 mmol) were slurried in ethanol (0.47 mL), toluene (6 mL), and water (2 mL), and degassed by passing N$_2$ through the mixture for 20 min. Tetrakis(triphenylphosphine)palladium (0) (21.0 mg, 0.0182 mmol) was then added and degassing continued for 5 min. The mixture was heated to 80° C. overnight. Some starting material remained so heating was continued for 4 more hours. The reaction mixture was cooled, poured into water and the product extracted with EtOAc. Some starting material crystallized out and was removed by filtration. The filtrate was chromatographed on silica with 1000:50:2.5 DCM:MeOH:ammonia. An early fraction proved to be starting material. Product eluted in a later, more polar fraction. This was crystallized from MeOH and dried in vacuo at 50° C. to remove residual solvent. Final yield of desired product was 57 mg (15%). MS (ESI+) consistent for $C_{22}H_{22}ClN_3O_4$ (M+H)$^+$: m/z 428.2, and MS (ESI−) consistent for $C_{22}H_{22}ClN_3O_4$ (M−H)$^-$: m/z 426.2.

Synthesis of Compound 3300

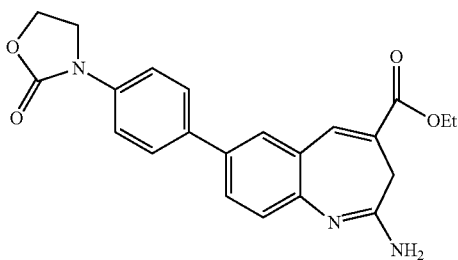 [SMILES: CCOC(=O)C1=Cc2cc(-c3ccc(N4CCOC4=O)cc3)ccc2N=C(N)C1]

Ethyl 2-amino-7-[4-(2-oxo-1,3-oxazolidin-3-yl)phenyl]-3H-1-benzazepine-4-carboxylate 3-[4-(4,4,5,5-Tetramethyl-1,3,2-dioxaborolan-2-yl)phenyl]-1,3-oxazolidin-2-one (0.631 g, 2.18 mmol), ethyl 2-amino-7-bromo-3H-1-benzazepine-4-carboxylate (0.450 g, 1.46 mmol), toluene (10.0 mL), water (2.5 mL), ethanol (0.70 mL), and cesium carbonate (1.42 g, 4.37 mmol) were combined and degassed by bubbling $N_2$ through the mixture. Tetrakis(triphenylphosphine)palladium(0) (0.0841 g, 0.0728 mmol) was then added and degassing continued. The mixture was heated to 80° C. overnight. The next day LC showed no reaction. Dioxane (4 mL) was added to improve solubility along with an additional 80 mg of Tetrakis(triphenylphosphine)palladium(0). After heating again at 80° C. overnight, the mixture had turned black. HPLC showed the oxazolidinone boronate was diminished. LCMS showed product, which had a retention time similar to SM. The mixture was cooled and poured into water and extracted with EtOAc and then with DCM. Emulsions made extraction difficult. An attempt was made to chromatograph the product but it appeared the product was so insoluble that it sat on top of the column. The column was flushed with 500:50:2 DCM:MeOH:ammonia. The recovered product was slurried in MeOH in an attempt to purify it by trituration. HPLC showed this failed. Trituration with DCM also failed. An attempt to crystallize the product from DCM also failed (material would not dissolve). The DCM slurry was treated with a small amount of AcOH to make the salt. A solution resulted and then the salt crashed out. This was cooled and the solid collected by filtration. Purity of the solid was almost 97%. The solid was dissolved in DCM and treated with 50% sat. NaHCO$_3$ for 1 hr. The phases were separated, the organic layer dried over MgSO$_4$, and filtered. Concentration of the filtrate afforded a yellow solid which triturated in MeOH. HPLC showed product purity had improved to >97%. After drying in vacuum at 70° C., final yield of desired product was 135 mg (24%). The product was highly insoluble. MS (ESI+) consistent for $C_{22}H_{21}N_3O_4$ (M+H)$^+$: m/z 392.1.

Synthesis of Compound 3387

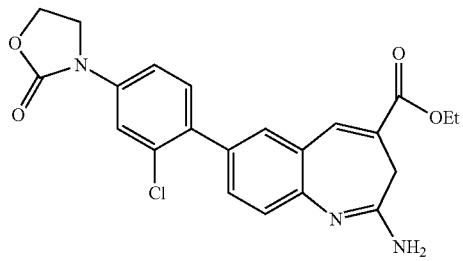 [SMILES: CCOC(=O)C1=Cc2cc(-c3ccc(N4CCOC4=O)cc3Cl)ccc2N=C(N)C1]

Ethyl 2-amino-7-[2-chloro-4-(2-oxo-1,3-oxazolidin-3-yl)phenyl]-3H-1-benzazepine-4-carboxylate Ethyl 2-amino-7-bromo-3H-1-benzazepine-4-carboxylate (440 mg, 1.4 mmol), 3-[3-chloro-4-(4,4,5,5-tetramethyl-1,3,2-dioxaborolan-2-yl)phenyl]-1,3-oxazolidin-2-one (691 mg, 2.13 mmol), and cesium carbonate (696 mg, 2.13 mmol) were slurried in ethanol (0.73 mL), toluene (9 mL), and water (3 mL) and degassed by passing $N_2$ through the mixture for 20 min. Tetrakis(triphenylphosphine)palladium (0) (32.9 mg, 0.0285 mmol) was then added and degassing continued for 5 min. The mixture was heated to 80° C. overnight. Some SM still remained. Heating was continued for 4 more hours and then the reaction mixture was cooled, poured into water, and the product extracted with hot EtOAc. The EtOAc solution was concentrated to a solid. This was triturated with MeOH and filtered to give an off white solid, 95% pure. The solids were again triturated with hot MeOH, cooled, and filtered to give 410 mg (68%) of the desired product, with excellent purity by NMR. MS (ESI+) consistent for $C_{22}H_{20}ClN_3O_4$ (M+H)$^+$: m/z 426.1.

Synthesis of Compound 3290

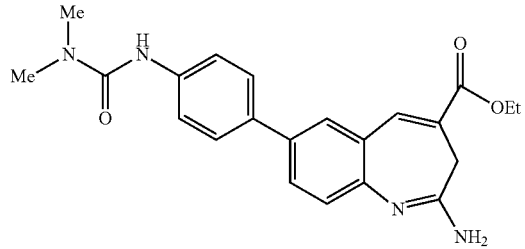 [SMILES: CCOC(=O)C1=Cc2cc(-c3ccc(NC(=O)N(C)C)cc3)ccc2N=C(N)C1]

Ethyl 2-amino-7-{4-[(dimethylcarbamoyl)amino]phenyl}-3H-1-benzazepine-4-carboxylate Ethyl 2-amino-7-bromo-3H-1-benzazepine-4-carboxylate (279 mg, 0.901 mmol), 1,1-dimethyl-3-[4-(4,4,5,5-tetramethyl-1,3,2-dioxaborolan-2-yl)phenyl]urea (320 mg, 1.1 mmol), potassium phosphate (1.91 g, 9.01 mmol), and [1,1'-bis(diphenylphosphino)ferrocene]dichloropalladium (II), complex with dichloromethane (1:1) (81.0 mg, 0.0991 mmol) were combined and the flask was backfilled three times with nitrogen. To this was added 1,4-dioxane (6.1 mL) and water (3.3 mL). The mixture was degassed until the potassium phosphate dissolved, giving a dark biphasic mixture. The mixture was then placed into a preheated oil bath at 100° C. After 30 minutes the reaction was complete and appeared, other than the dark color, to be quite clean. The crude was isolated by extracting with excess DCM and washing with water. The crude product was purified on a silica gel column, eluting first with 10% methanol in DCM, then with 5% methanol (containing 10% 0.7 M $NH_3$) in DCM. The product was isolated. A sample of this material was purified in 5 injections on a Prepstar LC instrument to recover 55 mg (16%) of the desired product. MS (ESI+) consistent for $C_{22}H_{24}N_4O_3$ $(M+H)^+$: m/z 393.1.

Synthesis of Compound 3336

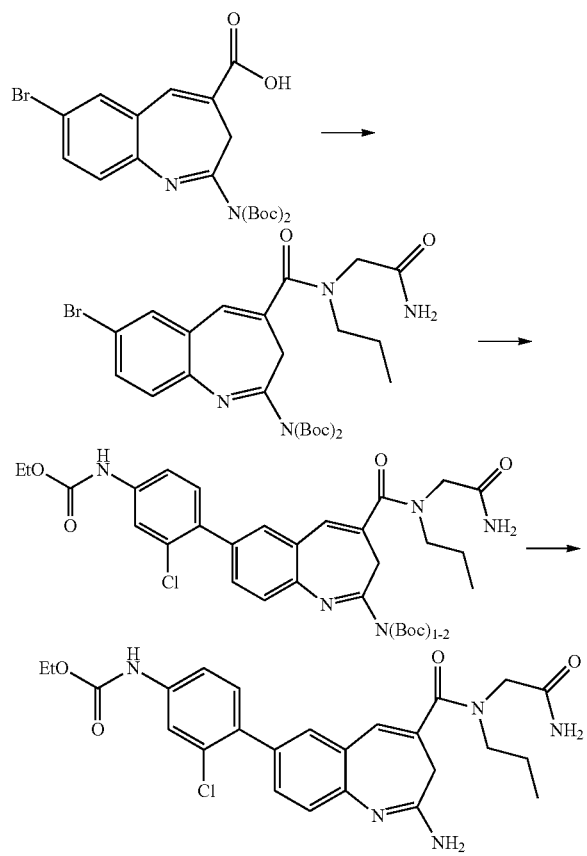

Ethyl (4-{2-amino-4-[(2-amino-2-oxoethyl)(propyl) carbamoyl)-3H-1-benzazepin-7-yl}-3-chlorophenyl) carbamate Step 1.
2-[Bis(tert-butoxycarbonyl)amino]-7-bromo-3H-1-benzazepine-4-carboxylic acid (1.21 g, 2.51 mmol) and N-(2-amino-2-oxoethyl)propan-1-aminium chloride (403 mg, 2.64 mmol) in DCM (20 mL) were treated with N,N-diisopropylethylamine (1.09 mL, 6.28 mmol) followed by HOBt (357 mg, 2.64 mmol) and the mixture stirred for 15 minutes, at which time the HOBt had dissolved. To this was added N-(3-dimethylaminopropyl)-N'-ethylcarbodiimide hydrochloride (723 mg, 3.77 mmol) and stirring continued at RT. After 6 hours the desired product had formed. The reaction was worked up by dilution with sat. aq. $NaHCO_3$.

The organic layer was separated, dried, filtered, and concentrated to give crude product, which was purified on a silica gel column eluting with 10-25% acetone in DCM, to give 790 mg (54%) of di-tert-butyl {4-[(2-amino-2-oxoethyl)(propyl)carbamoyl]-7-bromo-3H-1-benzazepin-2-yl}imidodicarbonate.

Step 2.
Di-tert-butyl {4-[(2-amino-2-oxoethyl)(propyl)carbamoyl]-7-bromo-3H-1-benzazepin-2-yl}imidodicarbonate (320 mg, 0.55 mmol), ethyl[3-chloro-4-(4,4,5,5-tetramethyl-1,3,2-dioxaborolan-2-yl)phenyl]carbamate (205 mg, 0.630 mmol), and cesium carbonate (270 mg, 0.83 mmol) were combined and slurried in toluene (6 mL), ethanol (0.6 mL), and water (2 mL). The mixture was degassed with $N_2$ and then treated with tetrakis(triphenylphosphine)palladium (0) (32 mg, 0.028 mmol). The mixture was again degassed and then heated in an oil bath held at 80° C. After about 3 hours some desired product was forming but starting material remained. The reaction was treated with additional ethyl[3-chloro-4-(4,4,5,5-tetramethyl-1,3,2-dioxaborolan-2-yl)phenyl]carbamate (55 mg; total of 1.4 equiv.) and tetrakis(triphenylphosphine)palladium(0) (68 mg; total of 0.16 equiv.) and after degassing the mixture was heated in an oil bath held at 80° C. overnight. The starting materials were consumed and one major product had formed. The crude was isolated by extracting with EtOAc and washing with water. The product was purified on a silica gel column eluting with 30% acetone in DCM to isolate 200 mg (60%) of ethyl (4-{4-[(2-amino-2-oxoethyl) (propyl)carbamoyl]-2-[(tert-butoxycarbonyl)amino]-3H-1-benzazepin-7-yl}-3-chlorophenyl)carbamate. The material was used as is in the next step.

Step 3.
Ethyl (4-{4-[(2-amino-2-oxoethyl)(propyl)carbamoyl]-2-[(tert-butoxycarbonyl)amino]-3H-1-benzazepin-7-yl}-3-chlorophenyl)carbamate (200 mg, 0.3 mmol) was dissolved in DCM (2 mL) and treated with TFA (0.6 mL, 8 mmol). The mixture was stirred at RT and after 2-3 hours the BOC group(s) had been removed. The volatiles were removed and the resultant oil triturated twice with ether to give a solid. The solid was then treated with aq. $NaHCO_3$ in a mixture of MeOH/DCM to give 55 mg (30%) of the free base of desired final product. MS (ESI+) consistent for $C_{25}H_{28}ClN_5O_4$ $(M+H)^+$: m/z 498.1, and MS (ESI—) consistent for $C_{25}H_{28}ClN_5O_4$ $(M-H)^-$: m/z 496.1.

Synthesis of Compound 3342

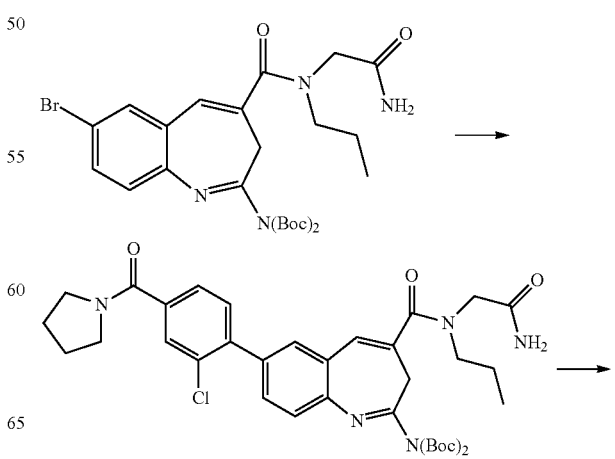

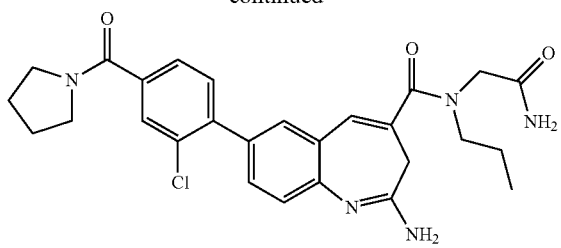

2-Amino-N-(2-amino-2-oxoethyl)-7-[2-chloro-4-(pyrrolidin-1-ylcarbonyl)phenyl]-N-propyl-3H-1-benzazepine-4-carboxamide Step 1.

Di-tert-butyl {4-[(2-amino-2-oxoethyl)(propyl)carbamoyl]-7-bromo-3H-1-benzazepin-2-yl}imidodicarbonate (444 mg, 0.766 mmol), 1-[3-chloro-4-(4,4,5,5-tetramethyl-1,3,2-dioxaborolan-2-yl)benzoyl]pyrrolidine (312 mg, 0.930 mmol), and cesium carbonate (393 mg, 1.21 mmol) were combined and slurried in toluene (8 mL), ethanol (0.9 mL), and water (3 mL). The mixture was degassed with $N_2$ and then treated with tetrakis(triphenylphosphine)palladium (0) (92 mg, 0.080 mmol). After further degassing, the mixture was heated in an oil bath held at 80° C. overnight. The reaction gave one new product with the desired mass. Crude was isolated using EtOAc and aq. $NaHCO_3$, then purified on a silica gel column eluting with 40-60% acetone in DCM to recover 350 mg (64%) of di-tert-butyl {4-[(2-amino-2-oxoethyl)(propyl)carbamoyl]-7-[2-chloro-4-(pyrrolidin-1-ylcarbonyl)phenyl]-3H-1-benzazepin-2-yl}imidodicarbonate.

Step 2.

Di-tert-butyl {4-[(2-amino-2-oxoethyl)(propyl)carbamoyl]-7-[2-chloro-4-(pyrrolidin-1-ylcarbonyl)phenyl]-3H-1-benzazepin-2-yl}imidodicarbonate (350 mg, 0.49 mmol) was dissolved in DCM (10 mL) and treated with TFA (3 mL). The reaction was complete after about 5 hours. The volatiles were removed and the compound taken up in a mixture of acetone/DCM (about 10% acetone). The solution was stirred with three consecutive portions of aq. $NaHCO_3$ and then the organic layer dried over anhydrous $Na_2SO_4$. Filtering and concentration gave a final yield of 240 mg (96%) of the desired product. MS (ESI+) consistent for $C_{27}H_{30}ClN_5O_3$ (M+H)$^+$: m/z 508.2, and MS (ESI−) consistent for $C_{27}H_{30}ClN_5O_3$ (M−H)$^-$: m/z 506.2.

Synthesis of Compound 3343

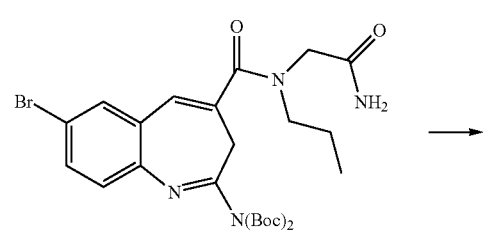

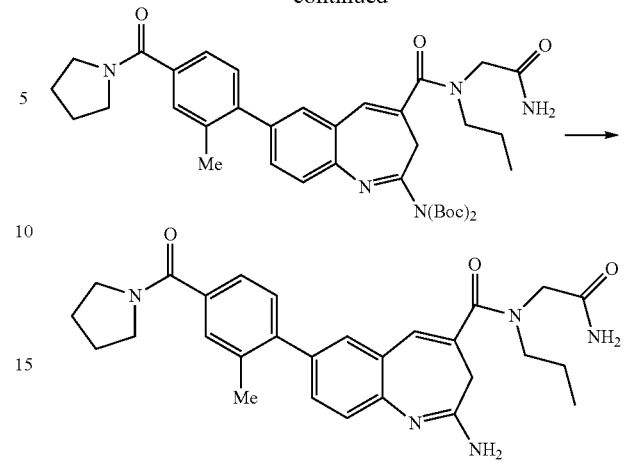

2-Amino-N-(2-amino-2-oxoethyl)-7-[2-methyl-4-(pyrrolidin-1-ylcarbonyl)phenyl]-N-propyl-3H-1-benzazepine-4-carboxamide Step 1.

Di-tert-butyl {4-[(2-amino-2-oxoethyl)(propyl)carbamoyl]-7-bromo-3H-1-benzazepin-2-yl}imidodicarbonate (379 mg, 0.654 mmol), 1-[3-methyl-4-(4,4,5,5-tetramethyl-1,3,2-dioxaborolan-2-yl)benzoyl]pyrrolidine (250 mg, 0.793 mmol), and cesium carbonate (335 mg, 1.03 mmol) were combined and slurried in toluene (10 mL), ethanol (1 mL), and water (3 mL). The mixture was degassed with $N_2$ and then treated with tetrakis(triphenylphosphine)palladium (0) (78 mg, 0.068 mmol). After further degassing, the mixture was heated in an oil bath held at 80° C. overnight. The reaction gave one new product with the desired mass. Crude was isolated using EtOAc and aq. $NaHCO_3$, then purified on a silica gel column eluting with 40-60% acetone in DCM to recover 320 mg (71%) of di-tert-butyl {4-[(2-amino-2-oxoethyl)(propyl)carbamoyl]-7-[2-methyl-4-(pyrrolidin-1-ylcarbonyl)phenyl]-3H-1-benzazepin-2-yl}imidodicarbonate.

Step 2.

Di-tert-butyl {4-[(2-amino-2-oxoethyl)(propyl)carbamoyl]-7-[2-methyl-4-(pyrrolidin-1-ylcarbonyl)phenyl]-3H-1-benzazepin-2-yl}imidodicarbonate (320 mg, 0.46 mmol) was dissolved in DCM (10 mL) and treated with TFA (3 mL). After 2 hours the reaction was complete. The volatiles were removed and the product (as the TFA salt) was redissolved in about 100 mL 10% acetone/DCM and treated with three consecutive portions of aq. $NaHCO_3$. The organic phase was separated, dried, and concentrated to give a final yield of 220 mg (97%) of the desired product. MS (ESI+) consistent for $C_{28}H_{33}N_5O_3$ (M+H)$^+$: m/z 488.2, and MS (ESI−) consistent for $C_{28}H_{33}N_5O_3$ (M−H)$^-$: m/z 486.3.

Example 2

HEK/TLR Assays

The activity of the compounds of this invention may be determined by the following assays.

The HEK-293 hTLR transfectant assay employs HEK293 cells stably transfected with various hTLRs and transiently co-transfected with a plasmid containing an NF-κB driven secreted embryonic alkaline phosphate (SEAP) reporter gene. Stimulation of TLRs activates their downstream signaling pathways and induces nuclear translocation of the transcription factor NF-κB. Reporter gene activity is then measured using a spectrophotometric assay.

To measure antagonist activity, human embryonic kidney (HEK) cells (e.g., 293XL-hTLR8 cells available from InvivoGen, San Diego, Calif.) are prepared according to supplier's instructions and incubated with various concentrations of test compound overnight. The amount of induced luciferase is measured by reading the absorbance at 650 nm. The compounds of the invention have an $MC_{50}$ of 25 μM or less, wherein $MC_{50}$ is defined as the concentration at which 50% of maximum induction is seen.

For the TLR8 antagonist assays, cells are transiently transfected with the reporter gene on Day 1 per the supplier's instructions. Antagonist compounds are added to the cultures on Day 2 followed by addition of a TLR8 agonist approximately 2 hours later. Cultures are incubated overnight and SEAP activity is measured on Day 3.

In a typical assay, 50,000 HEK239 hTLR8 cells are seeded per culture well and transiently transfected with the SEAP reporter gene. Antagonists are added to cultures in culture medium and >1% DMSO over a concentration range of 0.1 nanomolar to 10 micromolar. TLR8 agonists are added to cultures 2 hours later at a fixed concentration (e.g., 1 micromolar or 10 micromolar of Compound A) and cultures are then incubated for 16-24 hrs at 37° C. in a humidified CO incubator. Antagonists are also evaluated for activity in the absence of agonist.

TLR8 agonist Compound A (also described herein as VTX-378) has the structure:

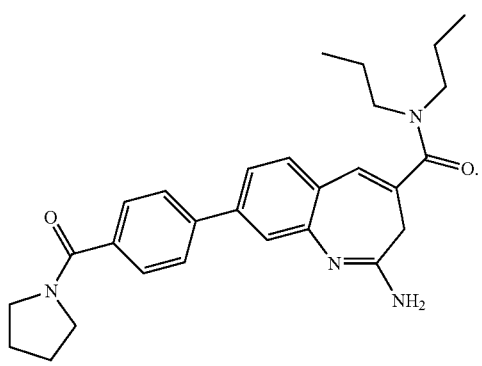 [SMILES: CCCN(CCC)C(=O)C1=Cc2ccc(-c3ccc(C(=O)N4CCCC4)cc3)cc2N=C(N)C1]

See WO 2007/024612.

3M002 (described herein) has the structure:

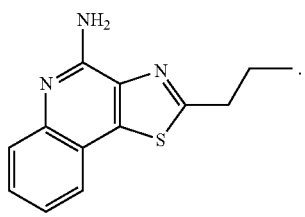 [SMILES: CCCc1nc2c(N)nc3ccccc3c2s1]

TLR8 antagonist activity was measured in a hTLR8 assay format, measuring $IC_{50}$ values. Compounds were incubated with hTLR8 reporter cells for two hours, then 1 μM Compound A was added to induce TLR8 overnight. $IC_{50}$s were then calculated.

$IC_{50}$ Results are shown below in Table 2, where + indicates an $IC_{50}$ (nM) of greater than or equal to 10,000, ++ indicates a value of 1,000-10,000, +++ indicates a value of less than 1,000.

TABLE 2

| Compound No. | IC50, nM, vs. | | | | |
|---|---|---|---|---|---|
| | VTX-378 | | | 3M002 | |
| | 0.5 μM | 1 μM | 10 μM | 1 μM | 10 μM |
| 3009 | | ++ | + | | |
| 3058 | | ++ | + | | |
| 2937 | | +++ | + | | |
| 3096 | | ++ | + | | |
| 3141 | +++ | ++ | | | |
| 3272 | ++ | ++ | | +++ | ++ |
| 3162 | ++ | ++ | | | |
| 3264 | +++ | +++ | | | +++ |
| 3267 | ++ | ++ | | | ++ |
| 3098 | ++ | + | | | ++ |
| 3127 | +++ | +++ | | +++ | ++ |
| 3155 | ++ | + | | | |
| 3294 | ++ | ++ | | | |
| 3386 | +++ | +++ | | | |
| 3126 | +++ | ++ | | +++ | ++ |
| 3059 | | ++ | + | | + |
| 3101 | ++ | + | | | + |
| 3055 | | ++ | + | | |
| 3119 | +++ | +++ | | | +++ |
| 3322 | +++ | +++ | | | +++ |
| 3190 | +++ | ++ | | | |
| 3199 | +++ | +++ | | | |
| 3261 | +++ | +++ | | | +++ |
| 3300 | +++ | +++ | | +++ | +++ |
| 3387 | +++ | +++ | | | +++ |
| 3290 | +++ | ++ | | +++ | ++ |
| 3343 | +++ | +++ | | | |
| 3342 | +++ | +++ | | | +++ |
| 3336 | +++ | ++ | | +++ | ++ |
| 2946 | | ++ | + | | |
| 3128 | +++ | ++ | | +++ | ++ |
| 3125 | ++ | ++ | | ++ | + |
| 3046 | | ++ | + | | ++ |
| 3093 | | + | + | | + |
| 3197 | | ++ | ++ | | |
| 3202 | | +++ | +++ | | |
| 3254 | ++ | ++ | | | |
| 2968 | ++ | ++ | + | | |
| 2930 | | + | + | | |
| 3097 | +++ | ++ | | | ++ |
| 3448 | +++ | +++ | | | |
| 3444 | +++ | +++ | | | |
| 3173 | +++ | +++ | | | |
| 3348 | +++ | +++ | | | +++ |
| 3260 | +++ | +++ | | | +++ |
| 2931 | | +++ | ++ | | |
| 2984 | | +++ | ++ | | |
| 2986 | | +++ | + | | |
| 2987 | | +++ | ++ | | |
| 2919 | | + | + | | |
| 2922 | | ++ | + | | |
| 2926 | | ++ | + | | |

Example 3

Human PBMCs Assays

The antagonist activity of the compounds of this invention was further demonstrated using human peripheral blood mononuclear cells (PBMCs). PBMCs contain a mixture of cells including monocytes and myeloid dendritic cells (mDCs) that express TLR8. When stimulated with the small molecule TLR8 agonists, PBMCs produce increased levels of IL-8. The ability of TLR8 antagonists to inhibit TLR8 production in human PBMCs was evaluated. Dose depending inhibition was observed when cells with stimulated with CL075, a structurally distinct thiazoquinoline TLR8 agonist. FIG. 1 shows dose-dependent inhibition of IL-8 production in human PBMC stimulated with CL075. Data shown in FIG. 1 are a representative experiment from one donor evaluated in duplicate culture wells. Increasing concentrations (from 3 to 1000 nM) of Compounds 3348, 2987, 3261, 3387, and 3448 (labeled as VTX-3348, VTX-2987, VTX-3261, VTX-3387, VTX-3448 in FIG. 1) were added to human PBMCs (50,000 cells/well in RPMI) and incubated for 2 hours in a 37° C. humidified $CO_2$ incubator. CL075 (Invivogen) was added to a final concentration of 100 ng/ML (400 nM) and cell were incubated overnight. At the end of the incubation, cells were centrifuged and cell culture supernatants were analyzed for IL-8 by ELISA (eBiosciene kit) per the manufacturer's instructions. The absorbance (OD 450 nM) representative of IL-8 levels is shown on the y-axis of FIG. 1. In the absence of any TLR8 agonists or antagonists (NS) the OD was 0.417 and addition of CL075 increased OD to 1.3777 (first two bars at the left of FIG. 1). As demonstrated in FIG. 1, in the presence of increasing concentrations of TLR8 antagonists, IL-8 levels were reduced in a dose dependent fashion.

Figure 2:
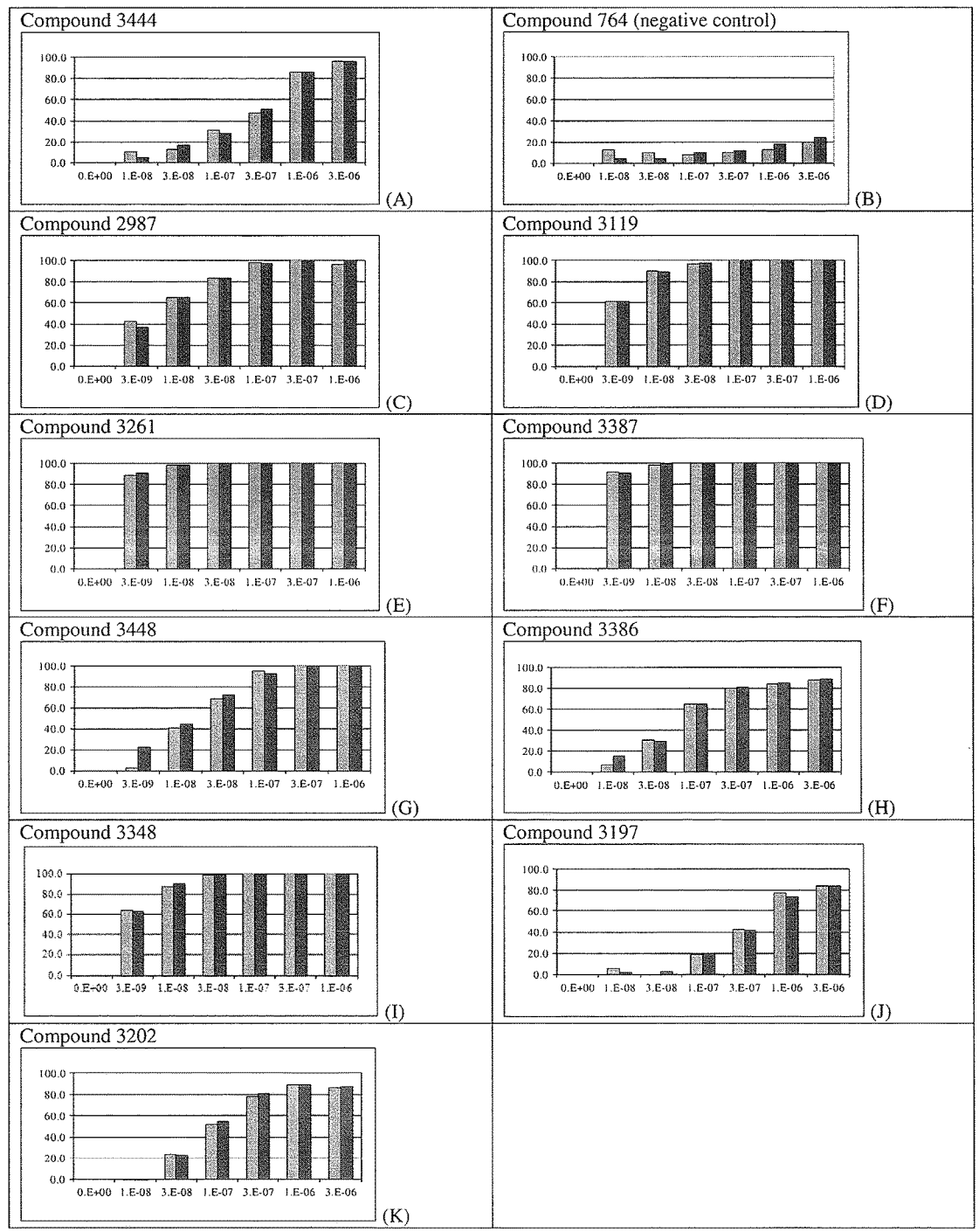
FIG. 2 is eleven graphs depicting the dose-dependent inhibition of IL-8 production in human PBMC stimulated with CL075 following administration of certain compounds described herein.

The experiment shown in FIG. 1 was repeated in multiple donors and with additional TLR8 antagonist molecules (see FIG. 2). Cells were stimulated with CL075 (100 ng/mL) and inhibition of IL-8 production was measured as described in FIG. 1. Percent inhibition is shown on the y-axis and concentrations of TLR8 antagonists (3-1000 nM) are shown on the x-axis in FIG. 2.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound having the formula I:

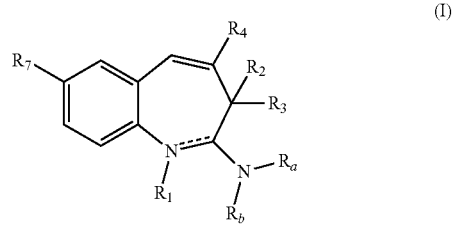

or a pharmaceutically acceptable salt thereof, wherein
= = = = = = is a double bond or a single bond;
$R_2$ and $R_3$ are independently selected from H and unsubstituted or substituted $C_1$-$C_6$ alkyl, or $R_2$ and $R_3$, together with the carbon atom to which they are attached, form a saturated carbocycle having from 3 to 7 members, or $R_3$ and one of $R_a$ or $R_b$, together with the atoms to which they are attached, form a 5-7 member heterocyclic ring;
$R_7$ is selected from the group consisting of:

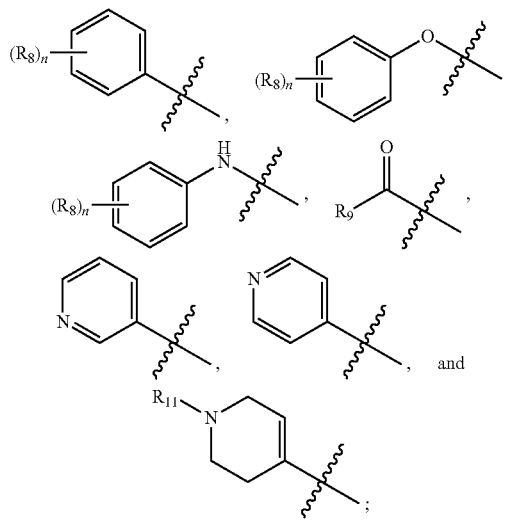

n is 0, 1, 2 or 3;
each $R_8$ is, independently, selected from unsubstituted or substituted $C_1$-$C_6$ alkyl, unsubstituted or substituted $C_1$-$C_6$ alkoxy, halogen, trihalomethyl, unsubstituted or substituted $C_1$-$C_6$ alkoxycarbonyl, nitro, unsubstituted or substituted carbonylamino, unsubstituted or substituted sulfonamide, unsubstituted or substituted heterocycle comprising 1 or 2, 5- or 6-member rings and 1-4 heteroatoms selected from N, O and S, and

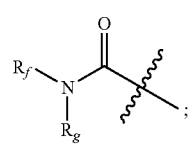

$R_9$ is unsubstituted or substituted $C_1$-$C_6$ alkyl, unsubstituted or substituted $C_1$-$C_6$ alkoxy, or —$NR_hR_j$;

$R_f$ and $R_g$ are each, independently, H, unsubstituted or substituted $C_1$-$C_6$ alkyl or $R_f$ and $R_g$, together with the nitrogen atom to which they are attached, form a heterocycle comprising 1 or 2, 5- or 6-member rings and optionally 1-3 additional heteroatoms selected from N, O and S;

$R_h$ and $R_j$ are each, independently, H, unsubstituted or substituted $C_1$-$C_6$ alkyl, unsubstituted or substituted $C_6$-$C_{10}$ aryl or $R_h$ and $R_j$, together with the nitrogen atom to which they are attached, form a heterocycle comprising 1 or 2, 5- or 6-member rings and optionally 1-3 additional heteroatoms selected from N, O and S;

$R_{11}$ is H, unsubstituted or substituted $C_1$-$C_6$ alkylcarbonyl, unsubstituted or substituted $C_1$-$C_6$ alkoxycarbonyl, 3-7 member carbocycle substituted carbonyl, or 5-7 member heterocyclyl substituted carbonyl;

$R_4$ is H, halogen, unsubstituted $C_1$-$C_6$ alkyl, or —C(O)NR$_c$R$_d$, or —C(O)OR$_{10}$;

$R_c$ and $R_d$ are independently selected from H and unsubstituted or substituted $C_1$-$C_6$ alkyl, where the $C_1$-$C_6$ alkyl is optionally substituted with aminocarbonyl or hydroxyl;

$R_{10}$ is selected from H and $C_1$-$C_6$ alkyl, where the alkyl is optionally substituted with one or more —OH;

$R_a$ and $R_b$ are independently selected from H, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ alkoxy, $C_1$-$C_6$ alkoxycarbonyl substituted amino, and $R_e$, wherein the $C_1$-$C_6$ alkyl is optionally substituted with one or more —OR$_{10}$ or R$_e$, or $R_3$ and one of $R_a$ and $R_b$ together with the atoms to which they are attached, form a 5-7 member heterocyclic ring;

$R_e$ is selected from —NH$_2$, —NH(C$_1$-C$_6$ alkyl), and —N(C$_1$-C$_6$ alkyl)$_2$; and $R_1$ is absent when ====== is a double bond, or when ====== is a single bond, $R_1$ is H, or $R_1$ and one of $R_a$ or $R_b$ are connected to form a saturated, partially unsaturated, or unsaturated heterocycle having 5-7 ring members and the other of $R_a$ or $R_b$ may be hydrogen or absent as necessary to accommodate ring unsaturation;

with the proviso that:
when $R_7$ is

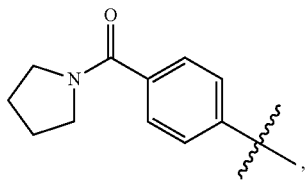 [SMILES: *c1ccc(C(=O)N2CCCC2)cc1]

then $R_4$ is not —COOR$_{10}$ where $R_{10}$ is $C_1$-$C_6$ alkyl, or —CONR$_c$R$_d$ where both $R_c$ and $R_d$ are unsubstituted $C_1$-$C_6$ alkyl, and $R_a$ and $R_b$ are not both selected from H, unsubstituted $C_1$-$C_6$ alkyl and $R_e$.

2. The compound of claim 1, wherein the compound is of formula II

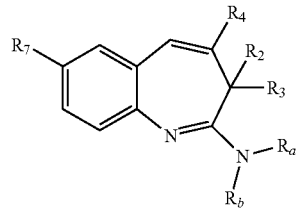

or a pharmaceutically acceptable salt thereof, wherein $R_7$ is selected from the group consisting of:

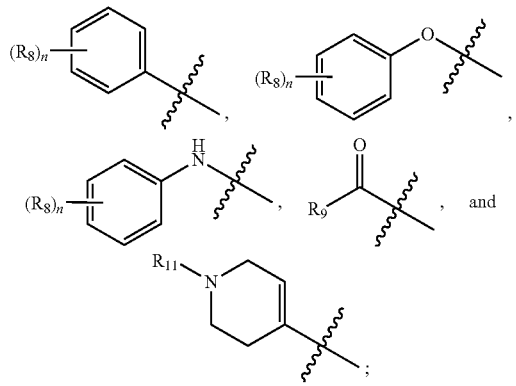

n is 0, 1, 2 or 3;

each $R_8$ is, independently, selected from unsubstituted or substituted $C_1$-$C_6$ alkyl, unsubstituted or substituted $C_1$-$C_6$ alkoxy, halogen, trihalomethyl, unsubstituted or substituted $C_1$-$C_6$ alkoxycarbonyl, unsubstituted or substituted carbonylamino, unsubstituted or substituted sulfonamide, unsubstituted or substituted heterocycle comprising 1 or 2, 5- or 6-member rings and 1-4 heteroatoms selected from N, O and S, and

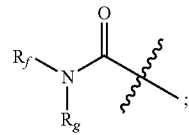

$R_9$ is unsubstituted or substituted $C_1$-$C_6$ alkyl, unsubstituted or substituted $C_1$-$C_6$ alkoxy or —NR$_h$R$_j$;

$R_f$ and $R_g$ are each, independently, H, unsubstituted or substituted $C_1$-$C_6$ alkyl or $R_f$ and $R_g$, together with the nitrogen atom to which they are attached, form a heterocycle comprising 1 or 2, 5- or 6-member rings and optionally 1-3 additional heteroatoms selected from N, O and S;

$R_h$ and $R_j$ are each, independently, H, unsubstituted or substituted $C_1$-$C_6$ alkyl or $R_h$ and $R_j$, together with the nitrogen atom to which they are attached, form a heterocycle comprising 1 or 2, 5- or 6-member rings and optionally 1-3 additional heteroatoms selected from N, O and S;

$R_{11}$ is H, unsubstituted or substituted $C_1$-$C_6$ alkylcarbonyl, unsubstituted or substituted $C_1$-$C_6$ alkoxycarbonyl, 3-7 member carbocycle substituted carbonyl, or 5-7 member heterocyclyl substituted carbonyl;

$R_4$ is selected from H, —C(O)NR$_c$R$_d$, —C(O)OR$_{10}$, halogen, and unsubstituted $C_1$-$C_6$ alkyl;

$R_c$ and $R_d$ are independently selected from H and unsubstituted or substituted $C_1$-$C_6$ alkyl, where the $C_1$-$C_6$ alkyl is optionally substituted with aminocarbonyl or hydroxyl;

$R_{10}$ is $C_1$-$C_6$ alkyl optionally substituted with one or more —OH;

$R_a$ and $R_b$ are independently selected from H, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ alkoxy, $C_1$-$C_6$ alkoxycarbonyl substituted amino, and $R_e$, wherein the $C_1$-$C_6$ alkyl is optionally substituted with one or more —OH, —OR$_{10}$ or R$_e$, or $R_3$ and one of $R_a$ or $R_b$ together with the atoms to which they are attached, form a 5-7 member heterocyclic ring;

$R_e$ is selected from —NH$_2$, —NH($C_1$-$C_6$ alkyl), and —N($C_1$-$C_6$ alkyl)$_2$.

3. The compound of claim 1, wherein $R_4$ is H, halogen, unsubstituted $C_1$-$C_6$ alkyl, —C(O)OR$_{10}$, or —C(O)NR$_c$R$_d$, where both $R_c$ and $R_d$ are unsubstituted or substituted $C_1$-$C_6$ alkyl.

4. The compound of claim 1, wherein $R_4$ is —C(O)OR$_{10}$, where $R_{10}$ is $C_1$-$C_6$ alkyl.

5. The compound of claim 1, wherein $R_4$ is —C(O)NR$_c$R$_d$ in which both $R_c$ and $R_d$ are propyl or at least one of $R_c$ or $R_d$ is $C_1$-$C_6$ alkyl substituted with one —OH.

6. The compound of claim 5, wherein one of $R_c$ and $R_d$ is

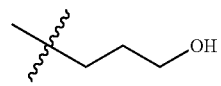 [SMILES: *CCCO]

and the other is propyl.

7. The compound of claim 1, $R_4$ is Br, methyl or ethyl.

8. The compound of claim 1, wherein $R_7$ is

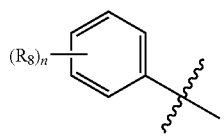

and n is 1, 2 or 3.

9. The compound of claim 8, wherein $R_7$ is not 3-methylphenyl nor 3,4-dichlorophenyl.

10. The compound of claim 1, $R_7$ is

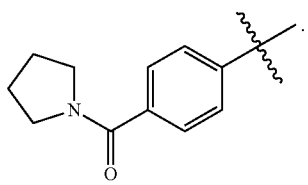 [SMILES: *c1ccc(C(=O)N2CCCC2)cc1]

11. The compound of claim 1, wherein at least one of $R_a$ and $R_b$ is not hydrogen, or one of $R_a$ and $R_b$ is unsubstituted or substituted $C_1$-$C_6$ alkyl and the other is hydrogen, or one or more of $R_a$ and $R_b$ is $C_1$-$C_6$ alkyl substituted with $R_e$, or both $R_a$ and $R_b$ are unsubstituted or substituted $C_1$-$C_6$ alkyl.

12. The compound of claim 1, wherein one of $R_a$ and $R_b$ is $R_e$ and the other of $R_a$ and $R_b$ is hydrogen.

13. The compound of claim 1, wherein at least one of $R_2$ and $R_3$ is not hydrogen, or $R_2$ and $R_3$ are connected to form a saturated carbocycle.

14. The compound of claim 1 wherein the compound is of the formula III:

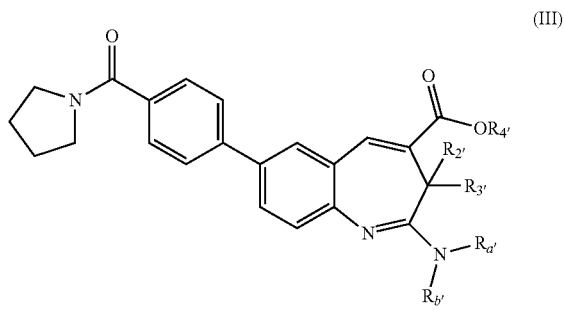

or a salt thereof, wherein $R_{2'}$ and $R_{3'}$ are independently selected from H and unsubstituted or substituted $C_1$-$C_6$ alkyl, or $R_{2'}$ and $R_{3'}$, together with the carbon atom to which they are attached, form a saturated carbocycle having from 3 to 7 members, or $R_{3'}$ and one of $R_{a'}$ or $R_{b'}$, together with the atoms to which they are attached, form a 5-7 member heterocyclic ring;

$R_{4'}$ is $C_1$-$C_6$ alkyl substituted with one or more —OH; and $R_{a'}$ and $R_{b'}$ are independently selected from H and unsubstituted or substituted $C_1$-$C_6$ alkyl, wherein the alkyl is optionally substituted with one or more —OH, or $R_{3'}$ and one of $R_{a'}$ or $R_{b'}$, together with the atoms to which they are attached, form a 5-7 member heterocyclic ring.

15. The compound of claim 14, wherein $R_{2'}$ and $R_{3'}$ are each H or both $R_{2'}$ and $R_{3'}$ are each methyl.

16. The compound of claim 14, wherein $R_{2'}$ or $R_{3'}$ is unsubstituted or substituted $C_1$-$C_6$ alkyl.

17. The compound of claim 14, wherein $R_{2'}$ and $R_{3'}$, together with the carbon atom to which they are attached, form a saturated carbocycle having from 3 to 7 members.

18. A pharmaceutical composition comprising the compound of claim 1 or a pharmaceutically acceptable salt thereof and a pharmaceutically acceptable carrier.

19. A compound selected from one of those with the following formula

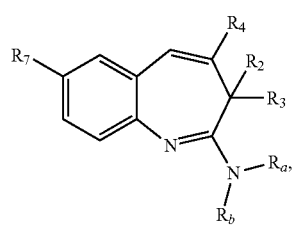

wherein $R_7$, $R_4$, $R_2$, $R_3$, $R_a$ and $R_b$ are as shown in Table 1:

| Compound No. | $R_7$ | $R_4$ | $R_2$, $R_3$ | $R_a$ | $R_b$ |
|---|---|---|---|---|---|
| 3010 | 4-(pyrrolidin-1-ylcarbonyl)phenyl | COOH | H, H | H | H |
| 3009 | 4-(pyrrolidin-1-ylcarbonyl)phenyl | CONH-i-Pr | H, H | H | H |
| 3058 | 3-(N,N-dimethylcarbamoyl)phenyl | COOEt | H, H | H | H |
| 2937 | 4-(N,N-dimethylcarbamoyl)phenyl | COOEt | H, H | H | H |
| 2882 | phenyl | COOEt | H, H | H | H |
| 3096 | 2-methylphenyl | COOEt | H, H | H | H |
| 3141 | 2-i-Pr-phenyl | COOEt | H, H | H | H |
| 3287 | 3-methylphenyl | COOEt | H, H | H | H |
| 3272 | 4-methylphenyl | COOEt | H, H | H | H |
| 3162 | 2,6-dimethylphenyl | COOEt | H, H | H | H |
| 3264 | 2-methoxyphenyl | COOEt | H, H | H | H |
| 3267 | 3-methoxyphenyl | COOEt | H, H | H | H |
| 3098 | 4-methoxyphenyl | COOEt | H, H | H | H |
| 3127 | 2-chlorophenyl | COOEt | H, H | H | H |
| 3155 | 2,3-dichlorophenyl | COOEt | H, H | H | H |
| 3102 | 3,4-dichlorophenyl | COOEt | H, H | H | H |
| 3294 | 2-chloro-3-methylphenyl | COOEt | H, H | H | H |
| 3386 | 2-chloro-3-methoxyphenyl | COOEt | H, H | H | H |
| 3126 | 2-trifluoromethylphenyl | COOEt | H, H | H | H |
| 3059 | 3-trifluoromethylphenyl | COOEt | H, H | H | H |
| 3101 | 4-ethoxycarbonylphenyl | COOEt | H, H | H | H |
| 3156 | 4-nitro | COOEt | H, H | H | H |
| 3055 | 4-(N,N-dimethylsulfamoyl)phenyl | COOEt | H, H | H | H |

-continued

| Compound No. | R_7 | R_4 | R_2, R_3 | R_a | R_b |
|---|---|---|---|---|---|
| 3119 | | COOEt | H, H | H | H |
| 3322 | | COOEt | H, H | H | H |
| 3190 | | COOEt | H, H | H | H |
| 3198 | | COOEt | H, H | H | H |
| 3199 | | COOEt | H, H | H | H |
| 3261 | | COOEt | H, H | H | H |
| 3300 | | COOEt | H, H | H | H |

-continued

| Compound No. | R₇ | R₄ | R₂, R₃ | Rₐ | R_b |
|---|---|---|---|---|---|
| 3387 | (oxazolidinone-N-phenyl-Cl) | COOEt | H, H | H | H |
| 3290 | (dimethylurea-phenyl) | COOEt | H, H | H | H |
| 3343 | (pyrrolidinyl-carbonyl-methyl-phenyl) | (N-propyl-CH₂C(O)NH₂ amide) | H, H | H | H |
| 3342 | (pyrrolidinyl-carbonyl-Cl-phenyl) | (N-propyl-CH₂C(O)NH₂ amide) | H, H | H | H |
| 3336 | (ethoxycarbonylamino-Cl-phenyl) | (N-propyl-CH₂C(O)NH₂ amide) | H, H | H | H |
| 2946 | (phenoxy) | COOEt | H, H | H | H |
| 3128 | (2-methylphenoxy) | COOEt | H, H | H | H |
| 3125 | (4-methoxyphenoxy) | COOEt | H, H | H | H |
| 3046 | (3-trifluoromethylphenoxy) | COOEt | H, H | H | H |

-continued
| Compound No. | R$_7$ | R$_4$ | R$_2$, R$_3$ | R$_a$ | R$_b$ |
|---|---|---|---|---|---|
| 3093 | | COOEt | H, H | H | H |
| 3057 | | COOEt | H, H | H | H |
| 3197 | | COOEt | H, H | H | H |
| 3094 | | COOEt | H, H | H | H |
| 3095 | | COOEt | H, H | H | H, |
or selected from those in Table 1A:
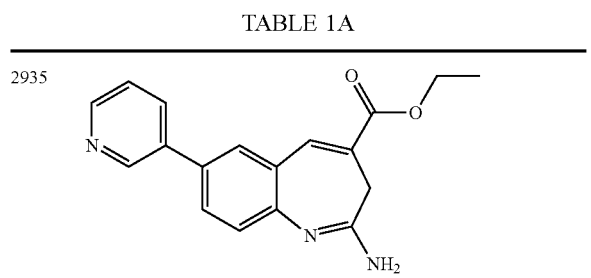
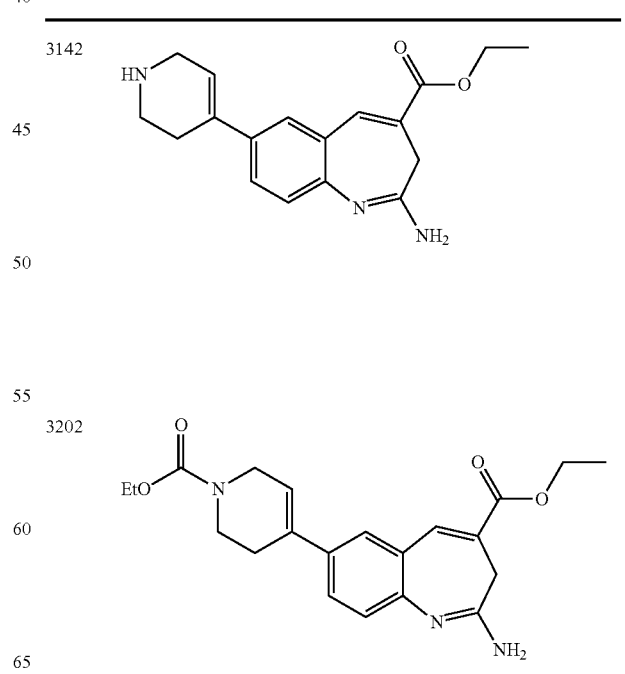

TABLE 1A-continued
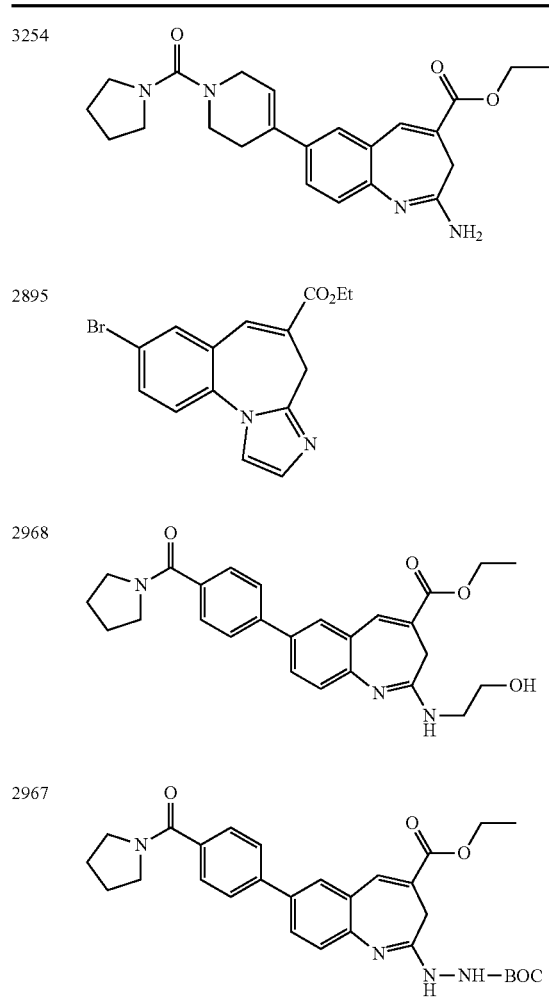
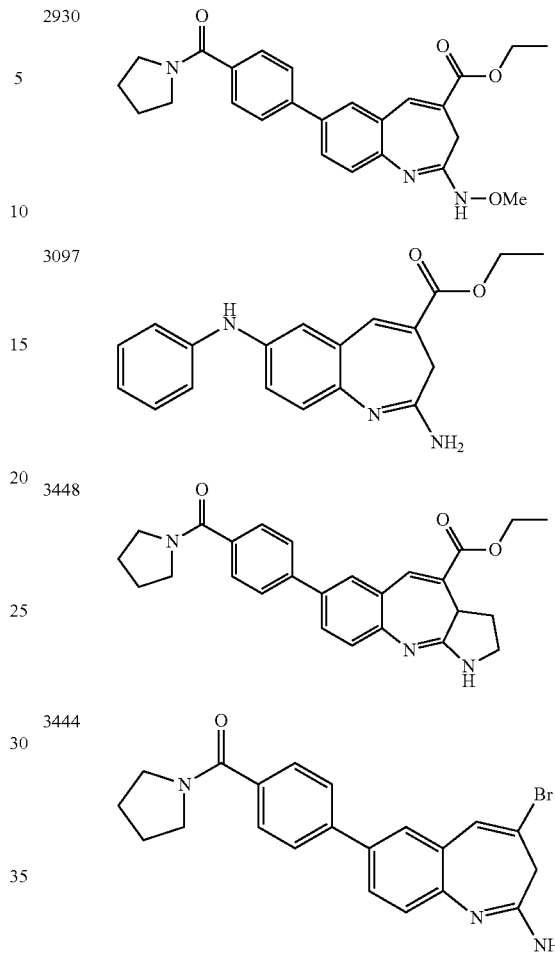
and a pharmaceutically acceptable salt thereof.
* * * * *